United States Patent
Borodina et al.

(10) Patent No.: US 9,868,966 B2
(45) Date of Patent: Jan. 16, 2018

(54) GENETICALLY ENGINEERED YEAST

(71) Applicant: TECHNICAL UNIVERSITY OF DENMARK, Kgs. Lyngby (DK)

(72) Inventors: Irina Borodina, Kgs. Lyngby (DK); Kanchana Rueksomtawin Kildegaard, Kgs. Lyngby (DK); Jochen Förster, Kgs. Lyngby (DK); Fredrik Öberg, Kgs. Lyngby (DK)

(73) Assignee: TECHNICAL UNIVERSITY OF DENMARK, Kgs. Lyngby (DK)

( * ) Notice: Subject to any disclaimer, the term of this patent is extended or adjusted under 35 U.S.C. 154(b) by 185 days.

(21) Appl. No.: 14/435,111

(22) PCT Filed: Oct. 10, 2013

(86) PCT No.: PCT/EP2013/071163
§ 371 (c)(1),
(2) Date: Apr. 10, 2015

(87) PCT Pub. No.: WO2014/057036
PCT Pub. Date: Apr. 17, 2014

(65) Prior Publication Data
US 2015/0267228 A1    Sep. 24, 2015

(30) Foreign Application Priority Data
Oct. 11, 2012  (EP) .................................... 12188198

(51) Int. Cl.
| | | |
|---|---|---|
| *C12N 5/04* | (2006.01) | |
| *C12N 9/10* | (2006.01) | |
| *A01H 1/00* | (2006.01) | |
| *C12P 7/64* | (2006.01) | |
| *C12P 21/06* | (2006.01) | |
| *C12P 7/42* | (2006.01) | |
| *C12P 7/52* | (2006.01) | |
| *C12N 9/04* | (2006.01) | |
| *C12N 9/88* | (2006.01) | |
| *C12N 9/00* | (2006.01) | |

(52) U.S. Cl.
CPC .............. *C12P 7/42* (2013.01); *C12N 9/0006* (2013.01); *C12N 9/1096* (2013.01); *C12N 9/88* (2013.01); *C12N 9/93* (2013.01); *C12P 7/52* (2013.01); *C12Y 101/01031* (2013.01); *C12Y 101/01059* (2013.01); *C12Y 206/01001* (2013.01); *C12Y 401/01011* (2013.01); *C12Y 401/01015* (2013.01); *C12Y 604/01001* (2013.01)

(58) Field of Classification Search
CPC .... C12P 7/64; C12P 7/62; C12P 21/06; A01H 1/00; C12N 5/04; C12N 1/21; C12N 9/10
See application file for complete search history.

(56) References Cited

U.S. PATENT DOCUMENTS

| 6,852,517 | B1 | 2/2005 | Suthers et al. | |
|---|---|---|---|---|
| 2007/0107080 | A1* | 5/2007 | Liao .................... | C12N 9/1096 800/281 |
| 2010/0136638 | A1 | 6/2010 | Liao et al. | |
| 2012/0135481 | A1 | 5/2012 | Jessen et al. | |

FOREIGN PATENT DOCUMENTS

| WO | 2005/118719 | 12/2005 |
|---|---|---|
| WO | 2010/031083 | 3/2010 |

OTHER PUBLICATIONS

International Search Report dated Nov. 18, 2013 in International Patent Application No. PCT/EP2013/071163.
Author Unknown, "Uncharacterized Aminotransferase yhxA," XP002692141, Retrieved from EBI accession No. UNIPROT:C2ZAL1, (7 pages).
Author Unknown, "Aspartate 1-decarboxylase; EC=4.1.1.11," XP002715871, Retrieved from EBI accession No. UNIPROT:A7U8C7, (7 pages).
Author Unknown, "yhxA—Uncharacterized aminotransferase YhxA—Bacillus subtillis (strain 168)," UniProtKB—P33189 (YHXA_BACSU), http://www.uniprot.org/uniprot/P33189, pp. 1-8 (Jul. 8, 2015).

* cited by examiner

*Primary Examiner* — Maryam Monshipouri
(74) *Attorney, Agent, or Firm* — Pillsbury Winthrop Shaw Pittman LLP

(57) ABSTRACT

A genetically modified *Saccharomyces cerevisiae* including an active fermentation pathway producing 3-HP expresses an exogenous gene expressing the aminotransferase YhxA from *Bacillus cereus* AH1272 catalyzing a transamination reaction between beta-alanine and pyruvate to produce malonate semialdehyde. The yeast may also express a 3-hydroxyisobutyrate dehydrogenase (HIBADH) and a 3-hydroxypropanoate dehydrogenase (3-HPDH) and aspartate 1-decarboxylase. Additionally the yeast may express pyruvate carboxylase and aspartate aminotransferase.

8 Claims, 3 Drawing Sheets

| Cultivation medium | Mineral minimal medium (batch) | | | |
|---|---|---|---|---|
| Overexpression of biosynthetic genes/Overexpression of precursor supply | - | AAT2↑ | PYC1↑ PYC2↑ | AAT2↑ PYC1↑ PYC2↑ |
| BcBAPAT↑ EcYdfG↑ TgPanD↑ | 0,4 | 0,3 | 0,5 | 0,4 |
| BcBAPAT↑↑ EcYdfG↑↑ TgPanD↑ | 0,6 | 0,7 | 0,6 | 0,7 |
| BcBAPAT↑ EcYdfG↑ TgPanD↑↑ | 1,0 | 1,6 | 1,0 | 1,3 |
| Cultivation medium | Feed-in-time medium (fed-batch) | | | |
| Overexpression of biosynthetic genes/Overexpression of precursor supply | - | AAT2↑ | PYC1↑ PYC2↑ | AAT2↑ PYC1↑ PYC2↑ |
| BcBAPAT↑ EcYdfG↑ TgPanD↑ | 1,9 | 1,9 | 2,8 | 2,0 |
| BcBAPAT↑↑ EcYdfG↑↑ TgPanD↑ | 3,7 | 2,2 | 3,0 | 3,6 |
| BcBAPAT↑ EcYdfG↑ TgPanD↑↑ | 5,6 | 5,7 | 7,0 | 8,5 |

Figure 3

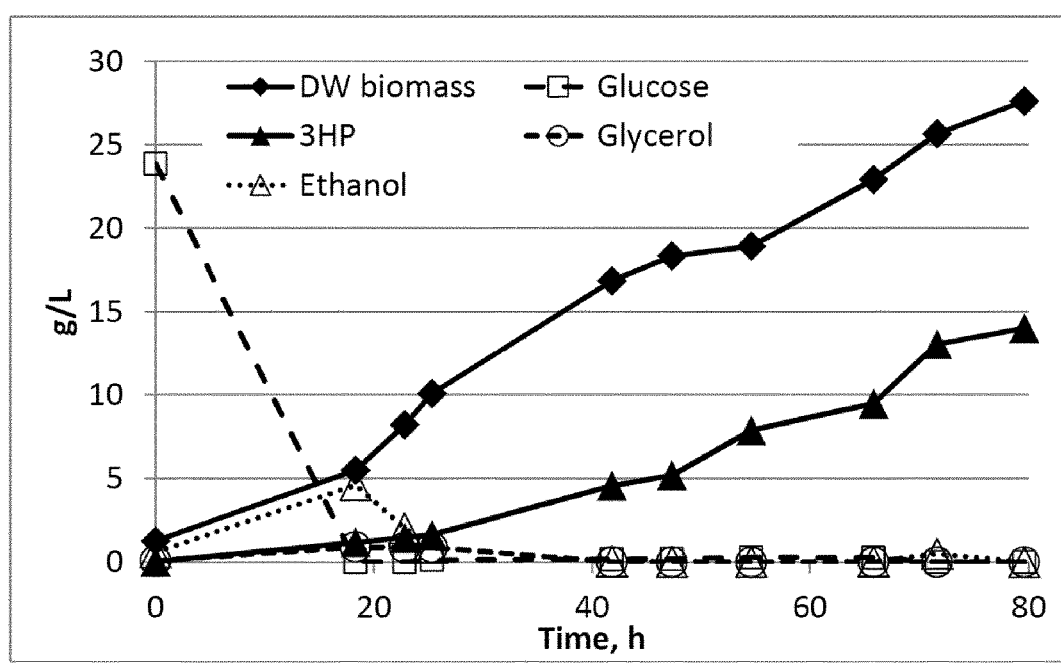

Figure 4

```
                       SEQUENCE LISTING

<160> NUMBER OF SEQ ID NOS: 89

<210> SEQ ID NO 1
<211> LENGTH: 451
<212> TYPE: PRT
<213> ORGANISM: Bacillus cereus
<220> FEATURE:
<221> NAME/KEY: SOURCE
<222> LOCATION: 1..451
<223> OTHER INFORMATION: /mol_type="protein"
      /organism="Bacillus cereus"

<400> SEQUENCE: 1

Met Glu Leu Met Ile Val Gln Val Thr Glu Gln Thr Gln Ser Leu Lys
1               5                   10                  15

Lys Thr Asp Glu Lys Tyr Leu Trp His Ala Met Arg Gly Ala Ala Pro
            20                  25                  30

Ser Pro Thr Asn Leu Ile Ile Thr Lys Ala Glu Gly Ala Trp Val Thr
        35                  40                  45

Asp Ile Asp Gly Asn Arg Tyr Leu Asp Gly Met Ser Gly Leu Trp Cys
    50                  55                  60
```

Val Asn Val Gly Tyr Gly Arg Lys Glu Leu Ala Arg Ala Ala Phe Glu
 65                  70                  75                  80

Gln Leu Glu Glu Met Pro Tyr Phe Pro Leu Thr Gln Ser His Val Pro
                 85                  90                  95

Ala Ile Lys Leu Ala Glu Lys Leu Asn Glu Trp Leu Asp Asp Glu Tyr
            100                 105                 110

Val Ile Phe Phe Ser Asn Ser Gly Ser Glu Ala Asn Glu Thr Ala Phe
        115                 120                 125

Lys Ile Ala Arg Gln Tyr His Gln Gln Lys Gly Asp His Gly Arg Tyr
    130                 135                 140

Lys Phe Ile Ser Arg Tyr Arg Ala Tyr His Gly Asn Ser Met Gly Ala
145                 150                 155                 160

Leu Ala Ala Thr Gly Gln Ala Gln Arg Lys Tyr Lys Tyr Glu Pro Leu
                165                 170                 175

Gly Gln Gly Phe Leu His Val Ala Pro Pro Asp Thr Tyr Arg Asn Pro
            180                 185                 190

Glu Asp Val His Thr Leu Ala Ser Ala Glu Glu Ile Asp Arg Val Met
        195                 200                 205

Thr Trp Glu Leu Ser Gln Thr Val Ala Gly Val Ile Met Glu Pro Ile
210                 215                 220

Ile Thr Gly Gly Gly Ile Leu Met Pro Pro Asp Gly Tyr Met Glu Lys
225                 230                 235                 240

Val Lys Glu Ile Cys Glu Lys His Gly Ala Leu Leu Ile Cys Asp Glu
                245                 250                 255

Val Ile Cys Gly Phe Gly Arg Thr Gly Lys Pro Phe Gly Phe Met Asn
            260                 265                 270

Tyr Gly Val Lys Pro Asp Ile Ile Thr Met Ala Lys Gly Ile Thr Ser
        275                 280                 285

Ala Tyr Leu Pro Leu Ser Ala Thr Ala Val Arg Arg Glu Val Tyr Glu
    290                 295                 300

Ala Phe Val Gly Ser Asp Asp Tyr Asp Arg Phe Arg His Val Asn Thr
305                 310                 315                 320

Phe Gly Gly Asn Pro Ala Ala Cys Ala Leu Ala Leu Lys Asn Leu Glu
                325                 330                 335

Ile Met Glu Asn Glu Lys Leu Ile Glu Arg Ser Lys Glu Leu Gly Glu
            340                 345                 350

Arg Leu Leu Tyr Glu Leu Glu Asp Val Lys Glu His Pro Asn Val Gly
        355                 360                 365

Asp Val Arg Gly Lys Gly Leu Leu Leu Gly Ile Glu Leu Val Glu Asp
    370                 375                 380

Lys Gln Thr Lys Glu Pro Ala Ser Ile Glu Lys Met Asn Lys Val Ile
385                 390                 395                 400

Asn Ala Cys Lys Glu Lys Gly Leu Ile Ile Gly Lys Asn Gly Asp Thr
                405                 410                 415

Val Ala Gly Tyr Asn Asn Ile Leu Gln Leu Ala Pro Pro Leu Ser Ile
            420                 425                 430

Thr Glu Glu Asp Phe Thr Phe Ile Val Lys Thr Met Lys Glu Cys Leu
        435                 440                 445

Ala Gln Leu
    450

<210> SEQ ID NO 2
<211> LENGTH: 1356
<212> TYPE: DNA

<213> ORGANISM: Artificial Sequence
<220> FEATURE:
<221> NAME/KEY: source
<222> LOCATION: 1..1356
<223> OTHER INFORMATION: /mol_type="DNA"
    /note="Synthetic DNA"
    /organism="Artificial Sequence"
<220> FEATURE:
<221> NAME/KEY: misc_feature
<222> LOCATION: 1..1356
<223> OTHER INFORMATION: /note="Codon optimised for S. cerevisiae"

<400> SEQUENCE: 2

```
atggaattga tgatcgttca agtcaccgaa caaacccaat ctttgaaaaa gactgacgaa      60
aagtacttgt ggcatgctat gagaggtgct gctccatctc caactaattt gattattact     120
aaggctgaag tgcctgggt tactgatatt gatggtaata gatacttgga dggtatgtct     180
ggtttgtggt gtgttaatgt tggttacggt agaaaagaat tggctagagc tgctttcgaa     240
caattggaag aaatgccata cttcccattg acccaatctc atgttccagc tattaagttg     300
gctgaaaagt tgaacgaatg gttggatgat gaatacgtca tcttcttctc taactctggt     360
tctgaagcta cgaaaccgc ttttaagatt gctagacaat accaccaaca aaagggtgat     420
catggtagat acaagttcat ctctagatac agagcttacc acggtaattc tatgggtgct     480
ttggctgcta ctggtcaagc tcaaagaaag tacaaatatg aacctttggg tcaaggtttc     540
ttgcatgttg ctccaccaga tacttataga aacccagaag atgttcatac tttggcctct     600
gctgaagaaa tcgatagagt tatgacttgg gaattgtctc aaactgttgc cggtgttatt     660
atggaaccta ttattactgg tggtggtatc ttgatgccac cagatggtta tatggaaaag     720
gtcaaagaaa tctgcgaaaa acatggtgcc ttgttgatct gtgatgaagt tatttgtggt     780
tttggtagaa ccggtaagcc atttggtttt atgaattacg tgttaagcc agacattatc     840
actatggcta agggtattac ttctgcctat ttgccattgt ctgctactgc tgttagaaga     900
gaagtttacg aagctttcgt tggttccgat gattacgata gattcagaca tgttaacacc     960
tttggtggta atccagctgc ttgtgcttta gctttgaaga acttggaaat catggaaaac    1020
gaaaaattga tcgaaagatc caagaattga ggtgaaagat tgttgtacga attagaagat    1080
gtcaaagaac acccaaacgt tggtgatgtt agaggtaaag gtttgttgtt gggtatcgaa    1140
ttggtcgaag ataagcaaac aaaagaacca gcctccatcg aaaagatgaa caaggttatt    1200
aacgcctgca agaaaaggg tttgatcatt ggtaagaacg tgatactgt tgctggttac    1260
aacaacatat tgcaattggc tccaccattg tccattaccg aagaagattt taccttcatc    1320
gtcaagacca tgaaggaatg tttggctcaa ttgtga                              1356
```

<210> SEQ ID NO 3
<211> LENGTH: 448
<212> TYPE: PRT
<213> ORGANISM: Pseudomonas putida
<220> FEATURE:
<221> NAME/KEY: SOURCE
<222> LOCATION: 1..448
<223> OTHER INFORMATION: /mol_type="protein"
    /organism="Pseudomonas putida"

<400> SEQUENCE: 3

```
Met Asn Met Pro Glu Thr Gly Pro Ala Gly Ile Ala Ser Gln Leu Lys
1               5                   10                  15

Leu Asp Ala His Trp Met Pro Tyr Thr Ala Asn Arg Asn Phe Gln Arg
            20                  25                  30
```

```
Asp Pro Arg Leu Ile Val Ala Ala Glu Gly Asn Tyr Leu Val Asp Asp
         35                  40                  45

His Gly Arg Lys Ile Phe Asp Ala Leu Ser Gly Leu Trp Thr Cys Gly
 50                  55                  60

Ala Gly His Thr Arg Lys Glu Ile Ala Asp Ala Val Thr Arg Gln Leu
 65                  70                  75                  80

Ser Thr Leu Asp Tyr Ser Pro Ala Phe Gln Phe Gly His Pro Leu Ser
                 85                  90                  95

Phe Gln Leu Ala Glu Lys Ile Ala Glu Leu Val Pro Gly Asn Leu Asn
            100                 105                 110

His Val Phe Tyr Thr Asn Ser Gly Ser Glu Cys Ala Asp Thr Ala Leu
            115                 120                 125

Lys Met Val Arg Ala Tyr Trp Arg Leu Lys Gly Gln Ala Thr Lys Thr
130                 135                 140

Lys Ile Ile Gly Arg Ala Arg Gly Tyr His Gly Val Asn Ile Ala Gly
145                 150                 155                 160

Thr Ser Leu Gly Gly Val Asn Gly Asn Arg Lys Met Phe Gly Gln Leu
                165                 170                 175

Leu Asp Val Asp His Leu Pro His Thr Val Leu Pro Val Asn Ala Phe
            180                 185                 190

Ser Lys Gly Leu Pro Glu Gly Gly Ile Ala Leu Ala Asp Glu Met
            195                 200                 205

Leu Lys Leu Ile Glu Leu His Asp Ala Ser Asn Ile Ala Ala Val Ile
            210                 215                 220

Val Glu Pro Leu Ala Gly Ser Ala Gly Val Leu Pro Pro Lys Gly
225                 230                 235                 240

Tyr Leu Lys Arg Leu Arg Glu Ile Cys Thr Gln His Asn Ile Leu Leu
                245                 250                 255

Ile Phe Asp Glu Val Ile Thr Gly Phe Gly Arg Met Gly Ala Met Thr
            260                 265                 270

Gly Ser Glu Ala Phe Gly Val Thr Pro Asp Leu Met Cys Ile Ala Lys
            275                 280                 285

Gln Val Thr Asn Gly Ala Ile Pro Met Gly Ala Val Ile Ala Ser Ser
290                 295                 300

Glu Ile Tyr Gln Thr Phe Met Asn Gln Pro Thr Pro Glu Tyr Ala Val
305                 310                 315                 320

Glu Phe Pro His Gly Tyr Thr Tyr Ser Ala His Pro Val Ala Cys Ala
                325                 330                 335

Ala Gly Leu Ala Ala Leu Asp Leu Leu Gln Lys Glu Asn Leu Val Gln
            340                 345                 350

Ser Ala Ala Glu Leu Ala Pro His Phe Glu Lys Leu Leu His Gly Val
            355                 360                 365

Lys Gly Thr Lys Asn Ile Val Asp Ile Arg Asn Tyr Gly Leu Ala Gly
370                 375                 380

Ala Ile Gln Ile Ala Ala Arg Asp Gly Asp Ala Ile Val Arg Pro Tyr
385                 390                 395                 400

Glu Ala Ala Met Lys Leu Trp Lys Ala Gly Phe Tyr Val Arg Phe Gly
                405                 410                 415

Gly Asp Thr Leu Gln Phe Gly Pro Thr Phe Asn Thr Lys Pro Gln Glu
            420                 425                 430

Leu Asp Arg Leu Phe Asp Ala Val Gly Glu Thr Leu Asn Leu Ile Asp
            435                 440                 445
```

```
<210> SEQ ID NO 4
<211> LENGTH: 1347
<212> TYPE: DNA
<213> ORGANISM: Artificial Sequence
<220> FEATURE:
<221> NAME/KEY: source
<222> LOCATION: 1..1347
<223> OTHER INFORMATION: /mol_type="DNA"
      /note="Synthetic DNA"
      /organism="Artificial Sequence"
<220> FEATURE:
<221> NAME/KEY: misc_feature
<222> LOCATION: 1..1347
<223> OTHER INFORMATION: /note="Codon optimised for S. cerevisiae"

<400> SEQUENCE: 4
atgaacatgc cagaaactgg tccagctggt attgcttctc aattgaaatt ggatgctcat      60
tggatgccat acactgctaa tagaaacttc aaagagatc caagattgat cgttgctgct     120
gaaggtaatt acttggttga tgatcatggt agaaagatct tcgatgcttt gtctggttg     180 tggacttgtg gtgctggtca tacaagaaaa gaaattgctg atgctgtcac cagacaattg     240
agtactttgg attattctcc agccttccaa tttggtcatc cattgtcttt tcaattggcc     300
gaaaagattg ctgaattggt tccaggtaat ttgaaccacg ttttctacac taactctggt     360
tctgaatgtg ctgatactgc tttgaaaatg gttagagcct attggagatt gaaaggtcaa     420
gctactaaga ccaagattat tggtagagct agaggttacc acggtgttaa tattgctggt     480
acttctttgg gtggtgttaa cggtaataga agatgtttg gtcaattatt ggacgttgat     540
catttgccac ataccgtttt gccagttaat gcttttcta agggtttgcc tgaagaaggt     600
ggtattgcat tggctgacga aatgttgaag ttgatcgaat gcatgacgc ttctaacatt     660 gctgctgtta tagttgaacc attggctggt tctgctggtg ttttgccacc accaaaaggt     720
tacttgaaga gattgagaga aatctgcacc caacacaaca tcttgttgat ttcgatgaa     780 gtcattaccg gtttcggtag aatgggtgct atgacaggtt ctgaagcttt tggtgttact     840
ccagatttga tgtgcattgc taagcaagtt accaatggtg ctattccaat gggtgcagtt     900
attgcttcat ctgaaatcta ccaaaccttc atgaatcaac ctactccaga atacgctgtt     960
gaatttccac atggttatac ctattctgct catccagttg cttgtgctgc aggtttggct    1020
gctttggatt tgttgcaaaa agaaaacttg gtccaatctg ctgcagaatt ggctccacat    1080
tttgaaaagt tgttgcatgg tgtcaaggg actaagaaca tcgttgatat tagaaactat    1140
ggtttggccg gtgccattca aattgctgct agagatggtg atgctatcgt tagaccatat    1200
gaagctgcta tgaagttgtg gaaagctggt ttttacgtta gattcggtgg tgatactta    1260 caattcggtc aacttttaa caccaagcca caagaattgg acagattatt tgatgctgtt    1320
ggtgaaacct tgaacttgat tgactga                                         1347

<210> SEQ ID NO 5
<211> LENGTH: 298
<212> TYPE: PRT
<213> ORGANISM: Pseudomonas aeruginosa
<220> FEATURE:
<221> NAME/KEY: SOURCE
<222> LOCATION: 1..298
<223> OTHER INFORMATION: /mol_type="protein"
      /organism="Pseudomonas aeruginosa"

<400> SEQUENCE: 5

Met Thr Asp Ile Ala Phe Leu Gly Leu Gly Asn Met Gly Gly Pro Met
1               5                   10                  15
```

Ala Ala Asn Leu Leu Lys Ala Gly His Arg Val Asn Val Phe Asp Leu
            20                  25                  30

Gln Pro Lys Ala Val Leu Gly Leu Val Glu Gln Gly Ala Gln Gly Ala
        35                  40                  45

Asp Ser Ala Leu Gln Cys Cys Glu Gly Ala Glu Val Val Ile Ser Met
    50                  55                  60

Leu Pro Ala Gly Gln His Val Glu Ser Leu Tyr Leu Gly Asp Asp Gly
65                  70                  75                  80

Leu Leu Ala Arg Val Ala Gly Lys Pro Leu Ile Asp Cys Ser Thr
                85                  90                  95

Ile Ala Pro Glu Thr Ala Arg Lys Val Ala Glu Ala Ala Ala Lys
            100                 105                 110

Gly Leu Thr Leu Leu Asp Ala Pro Val Ser Gly Val Gly Gly Ala
        115                 120                 125

Arg Ala Gly Thr Leu Ser Phe Ile Val Gly Gly Pro Ala Glu Gly Phe
    130                 135                 140

Ala Arg Ala Arg Pro Val Leu Glu Asn Met Gly Arg Asn Ile Phe His
145                 150                 155                 160

Ala Gly Asp His Gly Ala Gly Gln Val Ala Lys Ile Cys Asn Asn Met
                165                 170                 175

Leu Leu Gly Ile Leu Met Ala Gly Thr Ala Glu Ala Leu Ala Leu Gly
            180                 185                 190

Val Lys Asn Gly Leu Asp Pro Ala Val Leu Ser Glu Val Met Lys Gln
        195                 200                 205

Ser Ser Gly Gly Asn Trp Ala Leu Asn Leu Tyr Asn Pro Trp Pro Gly
    210                 215                 220

Val Met Pro Gln Ala Pro Ala Ser Asn Gly Tyr Ala Gly Gly Phe Gln
225                 230                 235                 240

Val Arg Leu Met Asn Lys Asp Leu Gly Leu Ala Leu Ala Asn Ala Gln
                245                 250                 255

Ala Val Gln Ala Ser Thr Pro Leu Gly Ala Leu Ala Arg Asn Leu Phe
            260                 265                 270

Ser Leu His Ala Gln Ala Asp Ala Glu His Glu Gly Leu Asp Phe Ser
        275                 280                 285

Ser Ile Gln Lys Leu Tyr Arg Gly Lys Asp
    290                 295

<210> SEQ ID NO 6
<211> LENGTH: 897
<212> TYPE: DNA
<213> ORGANISM: Pseudomonas aeruginosa
<220> FEATURE:
<221> NAME/KEY: source
<222> LOCATION: 1..897
<223> OTHER INFORMATION: /mol_type="DNA"
      /organism="Pseudomonas aeruginosa"
<220> FEATURE:
<221> NAME/KEY: misc_feature
<222> LOCATION: 1..897
<223> OTHER INFORMATION: /note="Codon optimised for S. cerevisiae"

<400> SEQUENCE: 6
atgacagaca tcgcattctt gggtttgggt aatatgggtg gtcctatggc tgctaatttg      60
ttgaaggctg gtcacagagt aaacgtattt gatttgcaac caaaagctgt attgggttta     120
gttgaacaag gtgctcaagg tgcagactcc gccttacaat gttgcgaagg tgcagaagtt     180
gtcatttcca tgttgcctgc cggtcaacat gtcgaaagtt tgtatttggg tgacgacggt     240

```
ttgttagcta gagtagcagg taaaccattg ttgatagatt gttctactat agccctgaa      300 acagctagaa aagttgcaga agctgcagcc gctaagggtt tgaccttgtt agacgctcca      360
gtctctggtg gtgtaggtgg tgcaagagcc ggtactttat cttttattgt aggtggtcca      420
gcagaaggtt tcgctagagc aagacctgtt ttggaaaaca tgggtagaaa catattccat      480
gctggtgacc acggtgccgg tcaagttgct aagatctgca caacatgtt gttgggtatt       540 ttaatggctg gtacagccga agctttggca ttaggtgtta aaatggttt agacccagca       600 gttttgtctg aagtcatgaa gcaatcttca ggtggtaact gggctttgaa tttgtataac      660
ccatggcctg tgttatgcc acaagcccct gcttcaaatg ttacgcagg tggtttccaa       720 gtcagattga tgaataagga tttgggttta gcattggcca acgctcaagc agttcaagct      780 tccaccccctt taggtgcctt ggctagaaat ttgttttctt tgcacgcaca agccgacgca     840
gaacacgaag gtttagattt cagtagtatc caaaagttgt atagaggtaa agattga         897
```

<210> SEQ ID NO 7
<211> LENGTH: 346
<212> TYPE: PRT
<213> ORGANISM: Candida albicans
<220> FEATURE:
<221> NAME/KEY: SOURCE
<222> LOCATION: 1..346
<223> OTHER INFORMATION: /mol_type="protein"
      /organism="Candida albicans"

<400> SEQUENCE: 7

Met Ser Thr Gln Pro Arg Leu Ser Thr Asn Tyr Gly Phe Ile Gly Leu
1               5                   10                  15

Gly Leu Met Gly Gln His Met Ala Arg His Val Tyr Asn Gln Leu Glu
            20                  25                  30

Pro Ser Asp Lys Leu Tyr Val Tyr Asp Val Asp Pro Lys His Thr Thr
        35                  40                  45

Gln Phe Leu Thr Glu Val Thr Ser Gln Thr Pro Gln Asn Ala Pro Leu
    50                  55                  60

Leu Thr Pro Leu Asn Ser Leu Lys Asp Phe Thr Thr Glu Val Asp Ser
65                  70                  75                  80

Gln Leu Asp Phe Ile Val Thr Met Val Pro Glu Gly Lys His Val Lys
                85                  90                  95

Ser Val Val Ser Glu Leu Val Gly His Tyr Lys Ser Thr Gly Asn Tyr
            100                 105                 110

Asp Pro Ser Ile Lys Thr Thr Phe Leu Asp Ser Ser Thr Ile Asp Ile
        115                 120                 125

Pro Thr Ser Arg Asp Val His Gln Leu Val Lys Ser Ser Ile Pro Glu
    130                 135                 140

Phe Asp Phe Ile Asp Thr Pro Val Ser Gly Gly Val Ala Gly Ala Arg
145                 150                 155                 160

Lys Gly Thr Leu Ser Phe Met Leu Ser Arg Glu Thr His Asp Asp Ile
                165                 170                 175

Asp Pro Ser Leu Thr Ala Leu Leu Ser Lys Met Gly Ile Asn Ile Phe
            180                 185                 190

Pro Cys Gly Ala Thr His Gly Thr Gly Leu Ala Ala Lys Leu Ala Asn
        195                 200                 205

Asn Tyr Leu Leu Ala Ile Thr Asn Ile Ala Ala Asp Ser Phe Gln
    210                 215                 220

Leu Ala Lys Ser Phe Gly Leu Asn Leu Gln Asn Tyr Ala Lys Leu Val
225                 230                 235                 240

Ala Val Ser Thr Gly Lys Ser Trp Ala Ser Val Asp Asn Cys Pro Ile
            245                 250                 255

Pro Gly Val Tyr Pro Asp Asn Asn Leu Pro Ser Asp Val Asn Tyr Glu
            260                 265                 270

Gly Gly Phe Ile Thr Lys Leu Thr Arg Lys Asp Val Val Leu Ala Thr
            275                 280                 285

Glu Ser Ala Lys Phe Asn Asn Arg Phe Leu Met Leu Gly Asp Ile Gly
            290                 295                 300

Arg His Trp Tyr Asp Lys Ala Cys Glu Arg Glu Asp Ile Ala Asn Arg
305                 310                 315                 320

Asp Leu Ser Val Leu Phe Glu Trp Leu Gly Asp Leu Lys Gln Asn Glu
            325                 330                 335

Lys Gly Asp Val Ile Asp Val Lys Arg Lys
            340                 345

<210> SEQ ID NO 8
<211> LENGTH: 1041
<212> TYPE: DNA
<213> ORGANISM: Candida albicans
<220> FEATURE:
<221> NAME/KEY: source
<222> LOCATION: 1..1041
<223> OTHER INFORMATION: /mol_type="DNA"
      /organism="Candida albicans"
<220> FEATURE:
<221> NAME/KEY: misc_feature
<222> LOCATION: 1..1041
<223> OTHER INFORMATION: /note="Codon optimised for S. cerevisiae"

<400> SEQUENCE: 8
atgtctactc aacctagatt gtctaccaac tacggtttta ttggtttggg tttgatgggt      60
caacatatgg ctagacacgt ttacaatcaa ttggaaccat ccgataagtt gtacgtttac     120
gatgttgatc aaagcacac tactcaattc ttgactgaag ttacttctca aaccccacaa     180
aacgctccat tattgactcc attgaattcc ttgaaggatt caccaccga agttgattct     240 caattggatt tcatcgttac catggtccct gaaggtaaac atgttaagtc tgttgtttcc     300
gaattggtcg gtcattacaa gtctactggt aattacgatc catccatcaa gaccactttc     360
ttggattctt ccaccattga tattccaacc tccagagatg ttcatcaatt ggtcaaatcc     420
tccatcccag aattcgattt cattgatact ccagtttctg gtggtgttgc tggtgctaga     480
aaaggtactt tgtctttcat gttgtccaga gaaacccacg atgatattga tccatctttg     540
actgctttgt tgtccaagat gggtattaac attttccat gtggtgctac tcatggtact     600
ggtttggctg ctaaattggc taacaattac ttgttggcca ttaccaatat tgctgctgct     660 gattctttc aattggccaa gtcttttggt ttgaacttgc aaaactacgc taagttggtt     720
gctgtttcta caggtaaatc ttgggcttct gttgataact gtccaattcc aggtgtttac     780
ccagataaca atttgccatc tgatgtcaat tacgaaggtg gtttcattac aagttgacc     840 agaaaggatg ttgttttggc tactgaatct gccaagttca caacagatt tttgatgttg     900 ggtgacatcg gtagacattg gtatgataag gcttgtgaaa gagaagatat cgccaacaga     960
gatttgtccg ttttgtttga atggttgggt gatttgaagc aaaacgaaaa gggtgatgtt    1020
atcgacgtca agagaaagtg a                                               1041

<210> SEQ ID NO 9
<211> LENGTH: 295
<212> TYPE: PRT

<213> ORGANISM: Pseudomonas putida
<220> FEATURE:
<221> NAME/KEY: SOURCE
<222> LOCATION: 1..295
<223> OTHER INFORMATION: /mol_type="protein"
    /organism="Pseudomonas putida"

<400> SEQUENCE: 9

Met Arg Ile Ala Phe Ile Gly Leu Gly Asn Met Gly Ala Pro Met Ala
1               5                   10                  15

Arg Asn Leu Ile Lys Ala Gly His Gln Leu Asn Leu Phe Asp Leu Asn
            20                  25                  30

Lys Ala Val Leu Ala Glu Leu Ala Glu Leu Gly Gly Gln Ile Ser Pro
        35                  40                  45

Ser Pro Lys Asp Ala Ala Asn Ser Glu Leu Val Ile Thr Met Leu
50                  55                  60

Pro Ala Ala His Val Arg Ser Val Tyr Leu Asn Glu Asp Gly Val
65                  70                  75                  80

Leu Ala Gly Ile Arg Pro Gly Thr Pro Thr Val Asp Cys Ser Thr Ile
                85                  90                  95

Asp Pro Gln Thr Ala Arg Asp Val Ser Lys Ala Ala Ala Lys Gly
            100                 105                 110

Val Asp Met Gly Asp Ala Pro Val Ser Gly Thr Gly Gly Ala Ala
        115                 120                 125

Ala Gly Thr Leu Thr Phe Met Val Gly Ala Ser Thr Glu Leu Phe Ala
130                 135                 140

Ser Leu Lys Pro Val Leu Glu Gln Met Gly Arg Asn Ile Val His Cys
145                 150                 155                 160

Gly Glu Val Gly Thr Gly Gln Ile Ala Lys Ile Cys Asn Asn Leu Leu
                165                 170                 175

Leu Gly Ile Ser Met Ile Gly Val Ser Glu Ala Met Ala Leu Gly Asn
            180                 185                 190

Ala Leu Gly Ile Asp Thr Lys Val Leu Ala Gly Ile Ile Asn Ser Ser
        195                 200                 205

Thr Gly Arg Cys Trp Ser Ser Asp Thr Tyr Asn Pro Trp Pro Gly Ile
210                 215                 220

Ile Glu Thr Ala Pro Ala Ser Arg Gly Tyr Thr Gly Gly Phe Gly Ala
225                 230                 235                 240

Glu Leu Met Leu Lys Asp Leu Gly Leu Ala Thr Glu Ala Ala Arg Gln
                245                 250                 255

Ala His Gln Pro Val Ile Leu Gly Ala Val Ala Gln Gln Leu Tyr Gln
            260                 265                 270

Ala Met Ser Leu Arg Gly Glu Gly Gly Lys Asp Phe Ser Ala Ile Val
        275                 280                 285

Glu Gly Tyr Arg Lys Lys Asp
290                 295

<210> SEQ ID NO 10
<211> LENGTH: 888
<212> TYPE: DNA
<213> ORGANISM: Pseudomonas putida
<220> FEATURE:
<221> NAME/KEY: source
<222> LOCATION: 1..888
<223> OTHER INFORMATION: /mol_type="DNA"
    /organism="Pseudomonas putida"
<220> FEATURE:
<221> NAME/KEY: misc_feature
<222> LOCATION: 1..888

-continued

<223> OTHER INFORMATION: /note="Codon optimised for S. cerevisiae"

<400> SEQUENCE: 10

```
atgagaattg ccttcattgg tttgggtaat atgggtgctc caatggctag aaatttgatt      60
aaggctggtc accaattgaa cttgttcgat ttgaacaaag ctgtcttggc tgaattagct     120
gaattgggtg gtcaaatttc accatctcca aaagatgctg ctgctaactc tgaattggtt     180
attactatgt tgccagctgc tgctcatgtt agatctgttt acttgaatga agatggtgtt     240
ttggccggta ttagaccagg tactccaact gttgattgct ctactattga tccacaaacc     300
gctagagatg tttctaaagc tgctgcagct aaaggtgttg atatgggtga tgctccagtt     360
tctggtggta ctggtggtgc agctgctggt actttgactt ttatggttgg tgcttctacc     420
gaattattcg cttctttgaa accagttttg gaacaaatgg gtagaaacat tgtccattgt     480
ggtgaagttg gtacaggtca aattgctaag atctgcaaca atttgttgtt gggtatctcc     540
atgatcggtg tttctgaagc tatggcttta ggtaatgctt tgggtattga taccaaagtc     600
ttggcaggta tcattaactc ttctactggt agatgttggt cctctgatac ttataatcca     660
tggccaggta ttattgaaac tgctccagct tctagaggtt acactggtgg ttttggtgct     720
gaattgatgt tgaaagattt gggtttggct actgaagctg ctagacaagc tcatcaacca     780
gttattttgg gtgctgttgc tcaacaatta taccaagcta tgtctttgag aggtgaaggt     840
ggtaaagatt tctctgctat cgttgaaggt tacagaaaga aggactga                  888
```

<210> SEQ ID NO 11
<211> LENGTH: 296
<212> TYPE: PRT
<213> ORGANISM: Bacillus cereus
<220> FEATURE:
<221> NAME/KEY: SOURCE
<222> LOCATION: 1..296
<223> OTHER INFORMATION: /mol_type="protein"
/organism="Bacillus cereus"

<400> SEQUENCE: 11

```
Met Lys Lys Ile Gly Phe Ile Gly Leu Gly Asn Met Gly Leu Pro Met
1               5                   10                  15

Ser Lys Asn Leu Val Lys Ser Gly Tyr Thr Val Tyr Gly Val Asp Leu
            20                  25                  30

Asn Lys Glu Ala Glu Ala Ser Phe Glu Lys Glu Gly Gly Ile Ile Gly
        35                  40                  45

Leu Ser Ile Ser Lys Leu Ala Glu Thr Cys Asp Val Val Phe Thr Ser
    50                  55                  60

Leu Pro Ser Pro Arg Ala Val Glu Ala Val Tyr Phe Gly Ala Glu Gly
65                  70                  75                  80

Leu Phe Glu Asn Gly His Ser Asn Val Val Phe Ile Asp Thr Ser Thr
                85                  90                  95

Val Ser Pro Gln Leu Asn Lys Gln Leu Glu Glu Ala Ala Lys Glu Lys
            100                 105                 110

Lys Val Asp Phe Leu Ala Ala Pro Val Ser Gly Gly Val Ile Gly Ala
        115                 120                 125

Glu Asn Arg Thr Leu Thr Phe Met Val Gly Gly Ser Lys Asp Val Tyr
    130                 135                 140

Glu Lys Thr Glu Ser Ile Met Gly Val Leu Gly Ala Asn Ile Phe His
145                 150                 155                 160

Val Ser Glu Gln Ile Asp Ser Gly Thr Thr Val Lys Leu Ile Asn Asn
                165                 170                 175
```

-continued

```
Leu Leu Ile Gly Phe Tyr Thr Ala Gly Val Ser Glu Ala Leu Thr Leu
            180                 185                 190

Ala Lys Lys Asn Asn Met Asp Leu Asp Lys Met Phe Asp Ile Leu Asn
        195                 200                 205

Val Ser Tyr Gly Gln Ser Arg Ile Tyr Glu Arg Asn Tyr Lys Ser Phe
    210                 215                 220

Ile Ala Pro Glu Asn Tyr Glu Pro Gly Phe Thr Val Asn Leu Leu Lys
225                 230                 235                 240

Lys Asp Leu Gly Phe Ala Val Asp Leu Ala Lys Glu Ser Glu Leu His
                245                 250                 255

Leu Pro Val Ser Glu Met Leu Leu Asn Val Tyr Asp Glu Ala Ser Gln
            260                 265                 270

Ala Gly Tyr Gly Glu Asn Asp Met Ala Ala Leu Tyr Lys Lys Val Ser
        275                 280                 285

Glu Gln Leu Ile Ser Asn Gln Lys
    290                 295
```

<210> SEQ ID NO 12
<211> LENGTH: 891
<212> TYPE: DNA
<213> ORGANISM: Bacillus cereus
<220> FEATURE:
<221> NAME/KEY: source
<222> LOCATION: 1..891
<223> OTHER INFORMATION: /mol_type="DNA"
/organism="Bacillus cereus"
<220> FEATURE:
<221> NAME/KEY: misc_feature
<222> LOCATION: 1..891
<223> OTHER INFORMATION: /note="Codon optimised for S. cerevisiae"

<400> SEQUENCE: 12

```
atgaagaaga tcggtttcat tggtttgggt aatatgggtt tgccaatgtc taagaacttg     60
gtcaaatctg gttacaccgt ttacggtgtt gacttgaaca aagaagcaga agcctctttc    120
gaaaaagaag gtggtattat cggtttgtcc atttccaaat tggctgaaac ctgtgatgtt    180
gttttcacct ctttgccatc tccaagagct gttgaagctg tttattttgg tgctgaaggt    240
ttgttcgaaa acggtcattc taacgtcgtt ttcattgata cctctaccgt ttctccacaa    300
ttgaacaagc aattggaaga agctgccaaa gaaaaaaagg ttgatttttt ggctgctcca    360
gtttccggtg gtgttattgg tgcagaaaac agaactttga ctttcatggt tggtggttcc    420
aaggatgttt acgaaaagac cgaatctatc atgggtgttt tgggtgctaa catcttccat    480
gtttccgaac aaattgattc tggtactacc gtcaagttga ttaacaattt gttgattggt    540
ttctacaccg ccggtgtttc tgaagcttta actttggcta aaaagaacaa catggacttg    600
gacaagatgt tcgatatctt gaacgtttcc tacggtcaat ccagaatcta cgaaagaaac    660
tacaagtcct tcattgcccc agaaaattac gaaccaggtt tcactgttaa cttgttgaag    720
aaggatttgg gtttcgctgt cgatttggca aaagaatctg aattgcattt gccagtttct    780
gaaatgttgt tgaacgtcta cgatgaagct tctcaagctg gttatggtga aaatgatatg    840
gctgccttgt acaaaaaggt tagtgaacaa ttgatctcca atcaaaaatg a             891
```

<210> SEQ ID NO 13
<211> LENGTH: 314
<212> TYPE: PRT
<213> ORGANISM: Metallosphaera sedula
<220> FEATURE:
<221> NAME/KEY: SOURCE
<222> LOCATION: 1..314
<223> OTHER INFORMATION: /mol_type="protein"
      /organism="Metallosphaera sedula"

<400> SEQUENCE: 13

```
Met Thr Glu Lys Val Ser Val Gly Ala Gly Val Ile Gly Val Gly
1               5                   10                  15

Trp Ala Thr Leu Phe Ala Ser Lys Gly Tyr Ser Val Ser Leu Tyr Thr
                20                  25                  30

Glu Lys Lys Glu Thr Leu Asp Lys Gly Ile Glu Lys Leu Arg Asn Tyr
                35                  40                  45

Val Gln Val Met Lys Asn Asn Ser Gln Ile Thr Glu Asp Val Asn Thr
50                  55                  60

Val Ile Ser Arg Val Ser Pro Thr Thr Asn Leu Asp Glu Ala Val Arg
65                  70                  75                  80

Gly Ala Asn Phe Val Ile Glu Ala Val Ile Glu Asp Tyr Asp Ala Lys
                85                  90                  95

Lys Lys Ile Phe Gly Tyr Leu Asp Ser Val Leu Asp Lys Glu Val Ile
                100                 105                 110

Leu Ala Ser Ser Thr Ser Gly Leu Leu Ile Thr Glu Val Gln Lys Ala
                115                 120                 125

Met Ser Lys His Pro Glu Arg Ala Val Ile Ala His Pro Trp Asn Pro
130                 135                 140

Pro His Leu Leu Pro Leu Val Glu Ile Val Pro Gly Glu Lys Thr Ser
145                 150                 155                 160

Met Glu Val Val Glu Arg Thr Lys Ser Leu Met Glu Lys Leu Asp Arg
                165                 170                 175

Ile Val Val Leu Lys Lys Glu Ile Pro Gly Phe Ile Gly Asn Arg
                180                 185                 190

Leu Ala Phe Ala Leu Phe Arg Glu Ala Val Tyr Leu Val Asp Glu Gly
                195                 200                 205

Val Ala Thr Val Glu Asp Ile Asp Lys Val Met Thr Ala Ala Ile Gly
                210                 215                 220

Leu Arg Trp Ala Phe Met Gly Pro Phe Leu Thr Tyr His Leu Gly Gly
225                 230                 235                 240

Gly Glu Gly Gly Leu Glu Tyr Phe Phe Asn Arg Gly Phe Gly Tyr Gly
                245                 250                 255

Ala Asn Glu Trp Met His Thr Leu Ala Lys Tyr Asp Lys Phe Pro Tyr
                260                 265                 270

Thr Gly Val Thr Lys Ala Ile Gln Gln Met Lys Glu Tyr Ser Phe Ile
                275                 280                 285

Lys Gly Lys Thr Phe Gln Glu Ile Ser Lys Trp Arg Asp Glu Lys Leu
                290                 295                 300

Leu Lys Val Tyr Lys Leu Val Trp Glu Lys
305                 310
```

<210> SEQ ID NO 14
<211> LENGTH: 945
<212> TYPE: DNA
<213> ORGANISM: Metallosphaera sedula
<220> FEATURE:
<221> NAME/KEY: source
<222> LOCATION: 1..945
<223> OTHER INFORMATION: /mol_type="DNA"
      /organism="Metallosphaera sedula"
<220> FEATURE:
<221> NAME/KEY: misc_feature
<222> LOCATION: 1..945

<223> OTHER INFORMATION: /note="Codon optimised for S. cerevisiae"

<400> SEQUENCE: 14

```
atgactgaaa aggtatctgt cgtcggtgct ggtgttattg gtgtcggttg ggctacatta      60
ttcgcatcta aaggttattc cgtctcattg tatacagaaa agaaagaaac cttggataag     120
ggtatcgaaa agttaagaaa ttacgtacaa gttatgaaaa ataactctca ataactgaa     180
gatgtcaaca cagtaatctc cagagtcagt ccaactacaa atttggacga agctgttaga     240
ggtgcaaact ttgttattga agccgtcata gaagattacg acgctaaaaa gaaaattttc     300
ggttacttgg attcagtatt ggacaaggaa gttatattgg cctcttcaac ctccggtttg     360
ttaatcactg aagttcaaaa ggcaatgagt aaacatccag aaagagcagt tattgcccat     420
ccttggaatc cacctcactt gttaccattg gttgaaatag tccctggtga aaagacttct     480
atggaagttg tcgaaagaac caagtcattg atggaaaagt tggatagaat agtagttgtc     540
ttaaagaaag aaatccctgg ttttattggt aacagattgg cctttgcttt attcagagaa     600
gctgtatatt tggttgacga aggtgtcgct actgtagaag atattgacaa agttatgaca     660
gctgcaatag gtttaagatg ggcttttatg ggtccattct tgacctacca tttgggtggt     720
ggtgaaggtg gtttggaata tttctttaac agaggttttg gttacggtgc aaacgaatgg     780
atgcacacat tagccaagta tgataaattc ccttacaccg tgttactaa ggctatccaa     840
caaatgaaag aatattcttt tattaagggt aaaactttcc aagaaatcag taagtggaga     900
gatgaaaagt tattgaaggt ctacaagtta gtctgggaaa agtga                     945
```

<210> SEQ ID NO 15
<211> LENGTH: 318
<212> TYPE: PRT
<213> ORGANISM: Sulfolobus tokadaii
<220> FEATURE:
<221> NAME/KEY: SOURCE
<222> LOCATION: 1..318
<223> OTHER INFORMATION: /mol_type="protein"
     /organism="Sulfolobus tokadaii"

<400> SEQUENCE: 15

Met Arg Gln Ile Lys Thr Val Ser Val Ile Gly Ala Gly Val Ile Gly
1               5                   10                  15

Ala Gly Trp Ser Thr Leu Leu Ala Leu Lys Gly Tyr Glu Asn Trp Phe
            20                  25                  30

Tyr Thr Glu Lys Lys Glu Thr Leu Asp Lys Gly Leu Ala Lys Ile Lys
        35                  40                  45

Gly Tyr Leu Asn Val Leu Tyr Glu Tyr Lys Leu Ile Asp Lys Glu Pro
    50                  55                  60

Asp Tyr Tyr Met Gln Arg Ile His Pro Thr Thr Lys Leu Asp Glu Ala
65                  70                  75                  80

Ile Ser Asn Thr Asp Phe Val Leu Glu Ala Ile Val Glu Glu Tyr Gly
                85                  90                  95

Ala Lys Lys Ala Leu Phe Lys Gln Leu Asp Glu Lys Leu Asp Lys Asp
            100                 105                 110

Val Ile Leu Ala Ser Ser Thr Ser Gly Leu Leu Met Thr Glu Ile Gln
        115                 120                 125

Lys Ala Met Thr Lys Tyr Pro Glu Arg Gly Ile Ile Ala His Pro Trp
    130                 135                 140

Asn Pro Pro His Leu Leu Pro Leu Val Glu Ile Val Pro Gly Glu Lys
145                 150                 155                 160

```
Thr Ser Gln Asp Thr Ile Tyr Ala Thr Lys Asp Phe Met Glu Asn Lys
                165                 170                 175
Leu Glu Arg Val Val Val Leu Lys Lys Glu Ile Ser Gly Phe Ile
            180                 185                 190
Gly Asn Arg Leu Ala Phe Ala Leu Phe Arg Glu Ala Val Tyr Leu Val
            195                 200                 205
Asp Glu Gly Ile Ala Thr Val Glu Asp Ile Asp Lys Val Met Thr Ala
        210                 215                 220
Ala Ile Gly Leu Arg Trp Ala Phe Met Gly Pro Phe Leu Thr Tyr His
225                 230                 235                 240
Leu Gly Gly Gly Glu Gly Gly Leu Glu Tyr Phe Phe Ser Arg Gly Phe
                245                 250                 255
Gly Tyr Gly Ala Asn Glu Trp Met His Thr Leu Ala Lys Tyr Asp Lys
            260                 265                 270
Phe Pro Tyr Thr Gly Val Val Lys Ser Val Gln Gln Met Lys Glu Tyr
            275                 280                 285
Glu Phe Val Lys Ser Lys Thr Phe Gln Glu Leu Ser Arg Trp Arg Asp
        290                 295                 300
Glu Lys Leu Ile Ser Leu Ile Lys Leu Leu Arg Gly Lys Ile
305                 310                 315
```

<210> SEQ ID NO 16
<211> LENGTH: 957
<212> TYPE: DNA
<213> ORGANISM: Sulfolobus tokadaii
<220> FEATURE:
<221> NAME/KEY: source
<222> LOCATION: 1..957
<223> OTHER INFORMATION: /mol_type="DNA"
      /organism="Sulfolobus tokadaii"
<220> FEATURE:
<221> NAME/KEY: misc_feature
<222> LOCATION: 1..957
<223> OTHER INFORMATION: /note="Codon optimised for S. cerevisiae"

<400> SEQUENCE: 16

```
atgagacaaa tcaagaccgt ttccgttata ggtgctggtg ttattggtgc aggttggtct    60
actttgttgg ctttgaaagg ttacgaaaac tggttctaca ccgaaaagaa agaaaccttg   120
gataagggtt tggccaagat taagggttac ttgaatgtct tgtacgaata caagttgatc   180
gacaaagaac cagactacta catgcaaaga attcatccaa ctaccaagtt ggacgaagct   240
atttctaaca ccgatttcgt tttggaagcc atcgttgaag aatacggtgc taaaaaggct   300
ttgttcaagc aattggacga aaagttggac aaggatgtta ttttggcttc ttctacctct   360
ggtttgttga tgaccgaaat tcaaaaggct atgaccaagt atccagaaag aggtattatt   420
gctcatccat ggaatccacc acatttgttg ccattggttg aaatagttcc aggtgaaaag   480
acttcccaag atacaatcta tgctaccaag gacttcatgg aaaacaagtt ggaaagagtt   540
gttgtcgtct tgaaaaaaga aatctccggt ttcatcggta acagattggc ttttgctttg   600
tttagagaag ccgtttactt ggttgatgaa ggtattgcta ccgttgaaga tatcgataag   660
gttatgactg ctgctattgg tttgagatgg gcttttatgg gtccattctt gacttatcat   720
ttgggtggtg gtgaaggtgg tttggaatac tttttttagta gaggttttgg ttacggtgcc   780
aacgaatgga tgcatacttt ggctaaatac gacaagtttc catacactgg tgttgtcaag   840
tctgtccaac aaatgaagga atacgaattt gttaagtcca agaccttcca agaattgtcc   900
agatggagag atgaaaagtt gatctccttg attaagttgt tgagaggtaa aatttga     957
```

<210> SEQ ID NO 17
<211> LENGTH: 428
<212> TYPE: PRT
<213> ORGANISM: Clostridium acetobutylicum
<220> FEATURE:
<221> NAME/KEY: SOURCE
<222> LOCATION: 1..428
<223> OTHER INFORMATION: /mol_type="protein"
      /organism="Clostridium acetobutylicum"

<400> SEQUENCE: 17

```
Met Lys Met Ser Ser Leu Tyr Glu Arg Ser Leu Lys Val Ile Pro Pro
1               5                   10                  15

Val Ala Gly Arg Ala Thr Lys Leu Gly Val Val Arg Gly Glu Gly Ala
            20                  25                  30

Tyr Leu Tyr Thr Glu Asp Gly Arg Lys Val Leu Asp Phe Ala Ser Gly
        35                  40                  45

Val Ala Val Cys Asn Leu Gly His Asn Asn Pro Ala Val Ile Lys Ala
    50                  55                  60

Ala Lys Glu Gln Met Asp Lys Leu Ile His Gly His Asn Val Val
65                  70                  75                  80

Tyr Tyr Glu Ser Tyr Val Lys Leu Ala Glu Lys Ile Val Glu Leu Thr
                85                  90                  95

Gly Asn Lys Thr Met Val Tyr Phe Ser Asn Ser Gly Ala Glu Ala Asn
            100                 105                 110

Glu Gly Ala Ile Lys Leu Ala Lys Tyr Ile Thr Lys Arg Gln Ala Ile
        115                 120                 125

Ile Ser Phe Lys Gly Ser Phe His Gly Arg Thr Leu Ala Thr Thr Ser
130                 135                 140

Ile Thr Gly Ser Ser Lys Tyr Arg Lys Asn Tyr Glu Gly Leu Leu
145                 150                 155                 160

Pro Ser Val Tyr Phe Ala Glu Tyr Pro Tyr Cys Phe Arg Cys Pro Tyr
                165                 170                 175

Lys Gln Asn Lys Glu Ser Cys Asn Met Glu Cys Ile Ser Gln Phe Glu
            180                 185                 190

Asp Met Phe Lys Lys Leu Ile Glu Pro Glu Ser Val Ala Ala Ile Ile
        195                 200                 205

Met Glu Pro Val Gln Gly Glu Gly Gly Tyr Ile Val Pro Pro Lys Lys
    210                 215                 220

Phe Leu Lys Ala Val Arg Glu Ile Cys Asp Lys Tyr Gly Ile Cys Leu
225                 230                 235                 240

Ile Phe Asp Glu Val Gln Cys Gly Phe Gly Arg Thr Gly Lys Ile Phe
                245                 250                 255

Ala His Glu Asn Phe Glu Val Leu Pro Asp Ile Phe Thr Cys Ala Lys
            260                 265                 270

Ala Ile Ala Ser Gly Phe Pro Leu Ser Ala Val Ile Gly Lys Lys Glu
        275                 280                 285

Leu Met Glu Lys Trp Pro Gly Ala His Gly Gly Thr Phe Gly Gly
    290                 295                 300

Asn Pro Val Ala Cys Ala Ala Ser Leu Ala Thr Ile Lys Glu Leu Glu
305                 310                 315                 320

Ser Gly Val Leu Asp Asn Ala Asn Asn Met Gly Asn Tyr Leu Lys Glu
                325                 330                 335

Glu Leu Leu Lys Leu Lys Asp Lys Tyr Ala Cys Ile Gly Asp Ile Arg
            340                 345                 350
```

```
Gly Ile Gly Leu Met Ile Gly Met Glu Phe Cys Lys Glu Asn Asn Asn
            355                 360                 365

Pro Asp Gly Asp Ile Val Thr Phe Ile Arg Glu Val Ala Val Asn Asn
370                 375                 380

Asn Leu Ile Leu Leu Gly Cys Gly Thr Glu His Asn Val Leu Arg Phe
385                 390                 395                 400

Ile Ala Pro Leu Thr Val Glu Lys Ser Glu Ile Asp Met Ala Ile Ser
                405                 410                 415

Ile Val Glu Lys Gly Ile Val Glu Tyr Leu Asn Lys
                420                 425

<210> SEQ ID NO 18
<211> LENGTH: 1287
<212> TYPE: DNA
<213> ORGANISM: Clostridium acetobutylicum
<220> FEATURE:
<221> NAME/KEY: source
<222> LOCATION: 1..1287
<223> OTHER INFORMATION: /mol_type="DNA"
      /organism="Clostridium acetobutylicum"
<220> FEATURE:
<221> NAME/KEY: misc_feature
<222> LOCATION: 1..1287
<223> OTHER INFORMATION: /note="Codon optimised for S. cerevisiae"

<400> SEQUENCE: 18
atgaagatgt cctccttgta cgaaagatcc ttgaaagtta ttccaccagt tgctggtaga      60
gctacaaaat gggtgttgt tagaggtgaa ggtgcttact tgtatactga gatggtaga      120 aaggttttgg atttcgcttc tggtgttgct gtatgtaatt tgggtcataa caatccagct      180
gttattaagg ctgccaaaga acaaatggat aagttgattc atggtggtca acgtcgtt      240 tactatgaat cttatgttaa gttggccgaa agatcgttg aattgactgg taacaagacc      300
atggtttact ctctctaattc tggtgctgaa gctaatgaag gtgcaatcaa attggctaag      360
tacatcacta agagacaagc catcatttcc ttcaagggtt cttttcatgg tagaactttg      420
gctactactt ccattactgg ttcctcatct aagtacagaa agaactacga aggtttgttg      480
ccatctgttt actttgctga ataccatac tgtttcagat gcccatacaa gcaaaacaaa      540
gaatcctgta acatggaatg catctcccaa ttcgaagata tgttcaagaa gttgatcgaa      600
ccagaatctg ttgccgccat tattatgaa ccagttcaag gtgaaggtgg ttatatcgtt      660
ccaccaaaga aattcttgaa ggccgttaga gaaatctgcg ataagtacgg tatttgcttg      720
atcttcgatg aagttcaatg tggttttggt agaaccggta agatttttgc tcacgaaaat      780
ttcgaagtcg aacctgatat tttcacctgt gctaaagcta ttgcttctgg ttttccattg      840
tctgccgtta tcggtaagaa agaattgatg gaaaaatggc cagctggtgc acatggtggt      900
acttttggtg gtaatccagt tgcttgtgct gcttctttag ctaccatcaa agaattggaa      960
tccggtgttt tggataacgc taacaatatg gtaactact tgaaagaaga attattgaag      1020
ttgaaggaca agtacgcctg cattggtgat attagaggta ttggtttgat gatcggtatg      1080
gaattctgca agaaaacaa caacccagat ggtgatatcg tcactttcat aagagaagtt      1140
gccgtcaaca caacttgat tttgttgggt tgtggtactg aacacaacgt cttgagattc      1200
attgctccat tgactgtcga aaagtccgaa attgatatgg ccatctctat cgttgaaaag      1260
ggtattgtcg aatacttgaa caaatga                                          1287

<210> SEQ ID NO 19
<211> LENGTH: 196
```

<212> TYPE: PRT
<213> ORGANISM: Escherichia coli
<220> FEATURE:
<221> NAME/KEY: SOURCE
<222> LOCATION: 1..196
<223> OTHER INFORMATION: /mol_type="protein"
/organism="Escherichia coli"

<400> SEQUENCE: 19

Met Asn Glu Ala Val Ser Pro Gly Ala Leu Ser Thr Leu Phe Thr Asp
1               5                   10                  15

Ala Arg Thr His Asn Gly Trp Arg Glu Thr Pro Val Ser Asp Glu Thr
            20                  25                  30

Leu Arg Glu Ile Tyr Ala Leu Met Lys Trp Pro Thr Ser Ala Asn
        35                  40                  45

Cys Ser Pro Ala Arg Ile Val Phe Thr Arg Thr Ala Glu Gly Lys Glu
    50                  55                  60

Arg Leu Arg Pro Ala Leu Ser Ser Gly Asn Leu Gln Lys Thr Leu Thr
65                  70                  75                  80

Ala Pro Val Thr Ala Ile Val Ala Trp Asp Ser Glu Phe Tyr Glu Arg
                85                  90                  95

Leu Pro Leu Leu Phe Pro His Gly Asp Ala Arg Ser Trp Phe Thr Ser
            100                 105                 110

Ser Pro Gln Leu Ala Glu Glu Thr Ala Phe Arg Asn Ser Ser Met Gln
        115                 120                 125

Ala Ala Tyr Leu Ile Val Ala Cys Arg Ala Leu Gly Leu Asp Thr Gly
    130                 135                 140

Pro Met Ser Gly Phe Asp Arg Gln His Val Asp Asp Ala Phe Phe Thr
145                 150                 155                 160

Gly Ser Thr Leu Lys Ser Asn Leu Leu Ile Asn Ile Gly Tyr Gly Asp
                165                 170                 175

Ser Ser Lys Leu Tyr Ala Arg Leu Pro Arg Leu Ser Phe Glu Glu Ala
            180                 185                 190

Cys Gly Leu Leu
        195

<210> SEQ ID NO 20
<211> LENGTH: 591
<212> TYPE: DNA
<213> ORGANISM: Escherichia coli
<220> FEATURE:
<221> NAME/KEY: source
<222> LOCATION: 1..591
<223> OTHER INFORMATION: /mol_type="DNA"
/organism="Escherichia coli"

<400> SEQUENCE: 20
atgaacgaag ccgttagccc aggtgcgctt agcaccctgt tcaccgatgc ccgcactcac      60
aacggctggc gggagacacc cgtcagcgat gagacgttac gggagattta tgccctgatg     120 aaatggggc cgacatcagc taactgttct ccggcacgga tcgtgtttac ccgcacggca     180
gaaggaaaag aacgtctgcg cccggcactt tccagcggca atctgcaaaa aaccctgacc     240
gcgcccgtca ccgctatcgt cgcctgggac agtgaatttt atgaacggtt accactactg     300
tttccccacg gtgatgcccg cagttggttt acctccagcc cacaacttgc cgaagaaaca     360
gcgtttcgca acagttccat gcaggcggcc tatctgatcg tcgcctgccg ggcgctggga     420
ctggataccg gccgatgtc gggctttgac cgtcaacacg tggacgacgc cttttttacg     480
ggcagcacgc tgaagagcaa tctgctgatt aatatcggct atggcgatag cagcaagctt     540
tatgcgcgcc tgccacgtct gtcctttgaa gaagcctgcg ggctgttgta a           591

<210> SEQ ID NO 21
<211> LENGTH: 248
<212> TYPE: PRT
<213> ORGANISM: Escherichia coli
<220> FEATURE:
<221> NAME/KEY: SOURCE
<222> LOCATION: 1..248
<223> OTHER INFORMATION: /mol_type="protein"
      /organism="Escherichia coli"

<400> SEQUENCE: 21

Met Ile Val Leu Val Thr Gly Ala Thr Ala Gly Phe Gly Glu Cys Ile
1               5                   10                  15

Thr Arg Arg Phe Ile Gln Gln Gly His Lys Val Ile Ala Thr Gly Arg
            20                  25                  30

Arg Gln Glu Arg Leu Gln Glu Leu Lys Asp Glu Leu Gly Asp Asn Leu
        35                  40                  45

Tyr Ile Ala Gln Leu Asp Val Arg Asn Arg Ala Ala Ile Glu Glu Met
    50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                85                  90                  95

Glu Asp Trp Glu Thr Met Ile Asp Thr Asn Asn Lys Gly Leu Val Tyr
            100                 105                 110

Met Thr Arg Ala Val Leu Pro Gly Met Val Glu Arg Asn His Gly His
        115                 120                 125

Ile Ile Asn Ile Gly Ser Thr Ala Gly Ser Trp Pro Tyr Ala Gly Gly
    130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
        195                 200                 205

Pro Glu Asp Val Ser Glu Ala Val Trp Trp Val Ser Thr Leu Pro Ala
    210                 215                 220

His Val Asn Ile Asn Thr Leu Glu Met Met Pro Val Thr Gln Ser Tyr
225                 230                 235                 240

Ala Gly Leu Asn Val His Arg Gln
                245

<210> SEQ ID NO 22
<211> LENGTH: 747
<212> TYPE: DNA
<213> ORGANISM: Escherichia coli
<220> FEATURE:
<221> NAME/KEY: source
<222> LOCATION: 1..747
<223> OTHER INFORMATION: /mol_type="DNA"
      /organism="Escherichia coli"

<400> SEQUENCE: 22
atgatcgttt tagtaactgg agcaacggca ggttttggtg aatgcattac tcgtcgtttt      60

```
attcaacaag ggcataaagt tatcgccact ggccgtcgcc aggaacggtt gcaggagtta    120
aaagacgaac tgggagataa tctgtatatc gcccaactgg acgttcgcaa ccgcgccgct    180
attgaagaga tgctggcatc gcttcctgcc gagtggtgca atattgatat cctggtaaat    240
aatgccggcc tggcgttggg catggagcct gcgcataaag ccagcgttga agactgggaa    300
acgatgattg ataccaacaa caaaggcctg gtatatatga cgcgcgccgt cttaccgggt    360
atggttgaac gtaatcatgg tcatattatt aacattggct caacggcagg tagctggccg    420
tatgccggtg gtaacgttta cggtgcgacg aaagcgtttg ttcgtcagtt tagcctgaat    480
ctgcgtacgg atctgcatgg tacgcgcggtg cgcgtcaccg acatcgaacc gggtctggtg    540
```

```
ggtggtaccg agttttccaa tgtccgcttt aaaggcgatg acggtaaagc agaaaaaacc    600
tatcaaaata ccgttgcatt gacgccagaa gatgtcagcg aagccgtctg gtgggtgtca    660
acgctgcctg ctcacgtcaa tatcaatacc ctggaaatga tgccggttac ccaaagctat    720
gccggactga atgtccaccg tcagtaa                                         747
```

<210> SEQ ID NO 23
<211> LENGTH: 471
<212> TYPE: PRT
<213> ORGANISM: Saccharomyces cerevisiae
<220> FEATURE:
<221> NAME/KEY: SOURCE
<222> LOCATION: 1..471
<223> OTHER INFORMATION: /mol_type="protein"
      /organism="Saccharomyces cerevisiae"

<400> SEQUENCE: 23

```
Met Ser Ile Cys Glu Gln Tyr Tyr Pro Glu Pro Thr Lys Pro Thr
 1               5                  10                  15

Val Lys Thr Glu Ser Ile Pro Gly Pro Glu Ser Gln Lys Gln Leu Lys
                20                  25                  30

Glu Leu Gly Glu Val Phe Asp Thr Arg Pro Ala Tyr Phe Leu Ala Asp
            35                  40                  45

Tyr Glu Lys Ser Leu Gly Asn Tyr Ile Thr Asp Val Asp Gly Asn Thr
 50                  55                  60

Tyr Leu Asp Leu Tyr Ala Gln Ile Ser Ser Ile Ala Leu Gly Tyr Asn
65                  70                  75                  80

Asn Pro Ala Leu Ile Lys Ala Ala Gln Ser Pro Glu Met Ile Arg Ala
                85                  90                  95

Leu Val Asp Arg Pro Ala Leu Gly Asn Phe Pro Ser Lys Asp Leu Asp
            100                 105                 110

Lys Ile Leu Lys Gln Ile Leu Lys Ser Ala Pro Lys Gly Gln Asp His
        115                 120                 125

Val Trp Ser Gly Leu Ser Gly Ala Asp Ala Asn Glu Leu Ala Phe Lys
    130                 135                 140

Ala Ala Phe Ile Tyr Tyr Arg Ala Lys Gln Arg Gly Tyr Asp Ala Asp
145                 150                 155                 160

Phe Ser Glu Lys Glu Asn Leu Ser Val Met Asp Asn Asp Ala Pro Gly
                165                 170                 175

Ala Pro His Leu Ala Val Leu Ser Phe Lys Arg Ala Phe His Gly Arg
            180                 185                 190

Leu Phe Ala Ser Gly Ser Thr Thr Cys Ser Lys Pro Ile His Lys Leu
        195                 200                 205

Asp Phe Pro Ala Phe His Trp Pro His Ala Glu Tyr Pro Ser Tyr Gln
    210                 215                 220
```

Tyr Pro Leu Asp Glu Asn Ser Asp Ala Asn Arg Lys Glu Asp His
225                 230                 235                 240

Cys Leu Ala Ile Val Glu Glu Leu Ile Lys Thr Trp Ser Ile Pro Val
            245                 250                 255

Ala Ala Leu Ile Ile Glu Pro Ile Gln Ser Glu Gly Gly Asp Asn His
        260                 265                 270

Ala Ser Lys Tyr Phe Leu Gln Lys Leu Arg Asp Ile Thr Leu Lys Tyr
    275                 280                 285

Asn Val Val Tyr Ile Ile Asp Glu Val Gln Thr Gly Val Gly Ala Thr
290                 295                 300

Gly Lys Leu Trp Cys His Glu Tyr Ala Asp Ile Gln Pro Pro Val Asp
305                 310                 315                 320

Leu Val Thr Phe Ser Lys Lys Phe Gln Ser Ala Gly Tyr Phe Phe His
                325                 330                 335

Asp Pro Lys Phe Ile Pro Asn Lys Pro Tyr Arg Gln Phe Asn Thr Trp
            340                 345                 350

Cys Gly Glu Pro Ala Arg Met Ile Ile Ala Gly Ala Ile Gly Gln Glu
        355                 360                 365

Ile Ser Asp Lys Lys Leu Thr Glu Gln Cys Ser Arg Val Gly Asp Tyr
370                 375                 380

Leu Phe Lys Lys Leu Glu Gly Leu Gln Lys Lys Tyr Pro Glu Asn Phe
385                 390                 395                 400

Gln Asn Leu Arg Gly Lys Gly Arg Gly Thr Phe Ile Ala Trp Asp Leu
                405                 410                 415

Pro Thr Gly Glu Lys Arg Asp Leu Leu Leu Lys Leu Lys Leu Asn
            420                 425                 430

Gly Cys Asn Val Gly Gly Cys Ala Val His Ala Val Arg Leu Arg Pro
        435                 440                 445

Ser Leu Thr Phe Glu Glu Lys His Ala Asp Ile Phe Ile Glu Ala Leu
    450                 455                 460

Ala Lys Ser Val Asn Glu Leu
465                 470

<210> SEQ ID NO 24
<211> LENGTH: 1416
<212> TYPE: DNA
<213> ORGANISM: Saccharomyces cerevisiae
<220> FEATURE:
<221> NAME/KEY: source
<222> LOCATION: 1..1416
<223> OTHER INFORMATION: /mol_type="DNA"
      /organism="Saccharomyces cerevisiae"

<400> SEQUENCE: 24
atgtctattt gtgaacaata ctacccagaa gagccaacca aaccaactgt taagaccgag    60
tccattcctg gtcctgaatc ccagaagcag ttaaaggaac tgggtgaagt ttttgacaca   120
agaccagcat atttttggc tgattatgag aaatctttag gtaactatat cactgatgtg   180
gatgggaaca catatttgga tttgtatgcc caaatctctt caattgcact tggttataac   240
aaccctgctt tgatcaaggc agcacaatca ccagaaatga tccgtgcttt ggtcgaccgt   300
cctgccttag gtaacttccc atctaaggat ttagacaaga tattgaagca atattgaaa   360 tctgcgccaa agggtcaaga tcacgtctgg tcagggcttt ccggtgcaga tgccaatgaa   420
ttagcgttca aggctgcctt tatttattac cgtgccaaac aaaggggcta tgatgccgat   480
ttttctgaaa aggaaaactt gtctgtcatg gacaatgacg cccctggcgc ccctcatctt   540

```
gccgtactat cgttcaagag agcgttccac ggtagattgt ttgcctccgg ttccacaact    600
tgttctaaac caattcacaa gttggatttc ccagccttcc actggcctca tgctgagtat    660
ccatcttacc aatacccatt agatgaaaat tctgatgcaa accgtaaaga ggatgaccat    720
tgcttggcca ttgttgaaga attaatcaaa acctggtcta ttccagttgc tgccttaatc    780
atcgaaccaa ttcaatctga gggaggtgat aaccacgctt ctaagtattt cttacaaaag    840
ctaagagaca ttaccttgaa gtataacgtt gtctacatca tagatgaagt gcaaacaggt    900
gtcggagcca ccggtaagct atggtgtcat gagtacgccg atattcaacc acctgtggat    960
ttagtgacct tttccaagaa attccaaagt gcaggatatt tcttccacga ccctaaattc   1020
attccaaaca aaccatacag acaattcaac acatggtgtg gtgaacctgc aagaatgatc   1080
attgcaggtg ccattggaca ggaaatctcc gacaagaagt tgactgaaca atgttcaaga   1140
gtaggtgatt atttgttcaa gaaattggag ggtttgcaga gaaatacccc tgaaaacttt   1200
caaaacttga gaggtaaagg aagaggcaca ttcattgcct gggatttgcc tactggtgag   1260
aagagagact tactattgaa gaaattgaag ttgaatggtt gcaacgttgg tggatgtgca   1320
gtccatgcag tgagattaag accttcatta acattcgagg agaagcatgc tgatatcttt   1380
attgaagcat tagccaaatc agttaatgaa ttatga                             1416

<210> SEQ ID NO 25
<211> LENGTH: 420
<212> TYPE: DNA
<213> ORGANISM: Saccharomyces cerevisiae
<220> FEATURE:
<221> NAME/KEY: source
<222> LOCATION: 1..420
<223> OTHER INFORMATION: /mol_type="DNA"
      /organism="Saccharomyces cerevisiae"

<400> SEQUENCE: 25
gcacacacca tagcttcaaa atgtttctac tccttttta ctcttccaga ttttctcgga     60
ctccgcgcat cgccgtacca cttcaaaaca cccaagcaca gcatactaaa tttccctct   120 ttcttcctct agggtgtcgt taattacccg tactaaaggt ttggaaaaga aaaagagac   180 cgcctcgttt cttttctcc gtcgaaaaag gcaataaaaa tttttatcac gtttcttttt   240
cttgaaaatt ttttttttg attttttct ctttcgatga cctcccattg atatttaagt   300
taataaacgg tcttcaattt ctcaagtttc agtttcattt ttcttgttct attacaactt   360
tttttacttc ttgctcatta gaaagaaagc atagcaatct aatctaagtt taattacaa   420

<210> SEQ ID NO 26
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="DNA"
      /note="synthetic primer"
      /organism="Artificial Sequence"
<220> FEATURE:
<221> NAME/KEY: misc_RNA
<222> LOCATION: 9..9
<223> OTHER INFORMATION: /note="uracil"

<400> SEQUENCE: 26
agtgcaggtg gtaccaaaac aatg                                           24

<210> SEQ ID NO 27
```

```
<211> LENGTH: 17
<212> TYPE: DNA
<213> ORGANISM: Artificial Sequence
<220> FEATURE:
<221> NAME/KEY: source
<222> LOCATION: 1..17
<223> OTHER INFORMATION: /mol_type="DNA"
      /note="synthetic primer"
      /organism="Artificial Sequence"
<220> FEATURE:
<221> NAME/KEY: misc_RNA
<222> LOCATION: 8..8

<400> SEQUENCE: 27
cgtgcgatgt cgactca                                                17

<210> SEQ ID NO 28
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="DNA"
      /note="synthetic primer"
      /organism="Artificial Sequence"
<220> FEATURE:
<221> NAME/KEY: misc_RNA
<222> LOCATION: 9..9
<223> OTHER INFORMATION: /note="uracil"

<400> SEQUENCE: 28
agtgcaggta aaacaatgaa cgaagccgtt ag                               32

<210> SEQ ID NO 29
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="DNA"
      /note="Synthetic primer"
      /organism="Artificial Sequence"
<220> FEATURE:
<221> NAME/KEY: misc_RNA
<222> LOCATION: 8..8
<223> OTHER INFORMATION: /note="uracil"

<400> SEQUENCE: 29
cgtgcgattt acaacagccc gcag                                        24

<210> SEQ ID NO 30
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Synthetic primer"
      /organism="Artificial Sequence"
<220> FEATURE:
<221> NAME/KEY: misc_RNA
<222> LOCATION: 9..9
<223> OTHER INFORMATION: /note="uracil"

<400> SEQUENCE: 30
agtgcaggta aaacaatgat cgttttagta actgg                            35

<210> SEQ ID NO 31
```

```
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="DNA"
      /note="Synthetic primer"
      /organism="Artificial Sequence"
<220> FEATURE:
<221> NAME/KEY: misc_RNA
<222> LOCATION: 8..8
<223> OTHER INFORMATION: /note="uracil"

<400> SEQUENCE: 31
cgtgcgattt actgacggtg gacattc                                          27

<210> SEQ ID NO 32
<211> LENGTH: 39
<212> TYPE: DNA
<213> ORGANISM: Artificial Sequence
<220> FEATURE:
<221> NAME/KEY: source
<222> LOCATION: 1..39
<223> OTHER INFORMATION: /mol_type="DNA"
      /note="Synthetic primer"
      /organism="Artificial Sequence"
<220> FEATURE:
<221> NAME/KEY: misc_RNA
<222> LOCATION: 9..9
<223> OTHER INFORMATION: /note="uracil"

<400> SEQUENCE: 32
agtgcaggta aaacaatgtc tatttgtgaa caatactac                             39

<210> SEQ ID NO 33
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="DNA"
      /note="Synthetic primer"
      /organism="Artificial Sequence"
<220> FEATURE:
<221> NAME/KEY: misc_RNA
<222> LOCATION: 8..8
<223> OTHER INFORMATION: /note="uracil"

<400> SEQUENCE: 33
cgtgcgattc ataattcatt aactgatttg g                                     31

<210> SEQ ID NO 34
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="DNA"
      /note="Synthetic primer"
      /organism="Artificial Sequence"
<220> FEATURE:
<221> NAME/KEY: misc_RNA
<222> LOCATION: 9..9
<223> OTHER INFORMATION: /note="uracil"

<400> SEQUENCE: 34
agtgcaggtg catggtacca aaacaatg                                         28
```

```
<210> SEQ ID NO 35
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="DNA"
      /note="Synthetic primer"
      /organism="Artificial Sequence"
<220> FEATURE:
<221> NAME/KEY: misc_RNA
<222> LOCATION: 8..8
<223> OTHER INFORMATION: /note="uracil"

<400> SEQUENCE: 35
cgtgcgatat gaggcccagg tcgac                                       25

<210> SEQ ID NO 36
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="DNA"
      /note="synthetic primer"
      /organism="Artificial Sequence"
<220> FEATURE:
<221> NAME/KEY: misc_RNA
<222> LOCATION: 9..9
<223> OTHER INFORMATION: /note="uracil"

<400> SEQUENCE: 36
acctgcactt tgtaattaaa acttag                                      26

<210> SEQ ID NO 37
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="DNA"
      /note="synthetic primer"
      /organism="Artificial Sequence"
<220> FEATURE:
<221> NAME/KEY: mRNA
<222> LOCATION: 8..8
<223> OTHER INFORMATION: /note="uracil"

<400> SEQUENCE: 37
cacgcgatgc acacaccata gcttc                                       25

<210> SEQ ID NO 38
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="DNA"
      /note="synthetic primer"
      /organism="Artificial Sequence"

<400> SEQUENCE: 38
aaaaggtacc atgatcgttt tagtaactgg                                  30

<210> SEQ ID NO 39
<211> LENGTH: 31
<212> TYPE: DNA
```

```
<213> ORGANISM: Artificial Sequence
<220> FEATURE:
<221> NAME/KEY: source
<222> LOCATION: 1..31
<223> OTHER INFORMATION: /mol_type="DNA"
      /note="synthetic primer"
      /organism="Artificial Sequence"

<400> SEQUENCE: 39
aaaattaatt aattactgac ggtggacatt c                              31

<210> SEQ ID NO 40
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="DNA"
      /note="synthetic primer"
      /organism="Artificial Sequence"
<220> FEATURE:
<221> NAME/KEY: misc_RNA
<222> LOCATION: 9..9
<223> OTHER INFORMATION: /note="uracil"

<400> SEQUENCE: 40
agtgcaggta aaacaatgat cagaaccatg                                30

<210> SEQ ID NO 41
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="DNA"
      /note="synthetic primer"
      /organism="Artificial Sequence"
<220> FEATURE:
<221> NAME/KEY: misc_RNA
<222> LOCATION: 8..8
<223> OTHER INFORMATION: /note="uracil"

<400> SEQUENCE: 41
cgtgcgattc aagcaacttg aactgg                                    26

<210> SEQ ID NO 42
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="DNA"
      /note="synthetic primer"
      /organism="Artificial Sequence"
<220> FEATURE:
<221> NAME/KEY: misc_RNA
<222> LOCATION: 9..9
<223> OTHER INFORMATION: /note="uracil"

<400> SEQUENCE: 42
agtgcaggta aaacaatgtt gagaacc                                   27

<210> SEQ ID NO 43
<211> LENGTH: 27
<212> TYPE: DNA
<213> ORGANISM: Artificial Sequence
<220> FEATURE:
<221> NAME/KEY: source
```

```
<222> LOCATION: 1..27
<223> OTHER INFORMATION: /mol_type="DNA"
      /note="synthetic primer"
      /organism="Artificial Sequence"
<220> FEATURE:
<221> NAME/KEY: misc_RNA
<222> LOCATION: 8..8
<223> OTHER INFORMATION: /note="uracil"

<400> SEQUENCE: 43
cgtgcgattc aaatggatct agaagtc                                           27

<210> SEQ ID NO 44
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="DNA"
      /note="synthetic primer"
      /organism="Artificial Sequence"
<220> FEATURE:
<221> NAME/KEY: misc_RNA
<222> LOCATION: 9..9
<223> OTHER INFORMATION: /note="uracil"

<400> SEQUENCE: 44
agtgcaggta aaacaatggc ttcttctact c                                      31

<210> SEQ ID NO 45
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="DNA"
      /note="synthetic primer"
      /organism="Artificial Sequence"
<220> FEATURE:
<221> NAME/KEY: misc_RNA
<222> LOCATION: 8..8
<223> OTHER INFORMATION: /note="uracil"

<400> SEQUENCE: 45
cgtgcgattc acaaatcttg acccaatc                                          28

<210> SEQ ID NO 46
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="synthetic primer"
      /organism="Artificial Sequence"
<220> FEATURE:
<221> NAME/KEY: misc_RNA
<222> LOCATION: 8..8
<223> OTHER INFORMATION: /note="uracil"

<400> SEQUENCE: 46
gtgcaggtaa aacaatgtta cacaggcacg gttc                                   34

<210> SEQ ID NO 47
<211> LENGTH: 33
<212> TYPE: DNA
<213> ORGANISM: Artificial Sequence
<220> FEATURE:
```

<210> SEQ ID NO 47
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="DNA"
     /note="synthetic primer"
     /organism="Artificial Sequence"
<220> FEATURE:
<221> NAME/KEY: mRNA
<222> LOCATION: 8..8
<223> OTHER INFORMATION: /note="uracil"

<400> SEQUENCE: 47
cgtgcgattc aacatgttcc tctatagttt ctc                                    33

<210> SEQ ID NO 48
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
     /note="synthetic primer"
     /organism="Artificial Sequence"
<220> FEATURE:
<221> NAME/KEY: misc_RNA
<222> LOCATION: 9..9
<223> OTHER INFORMATION: /note="uracil"

<400> SEQUENCE: 48
agtgcaggta aaacaatgga ccagaagctg ttaac                                  35

<210> SEQ ID NO 49
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="DNA"
     /note="Synthetic primer"
     /organism="Artificial Sequence"
<220> FEATURE:
<221> NAME/KEY: misc_RNA
<222> LOCATION: 8..8
<223> OTHER INFORMATION: /note="uracil"

<400> SEQUENCE: 49
cgtgcgattc aggtgtgttt aaagctg                                           27

<210> SEQ ID NO 50
<211> LENGTH: 126
<212> TYPE: PRT
<213> ORGANISM: Escherichia coli
<220> FEATURE:
<221> NAME/KEY: SOURCE
<222> LOCATION: 1..126
<223> OTHER INFORMATION: /mol_type="protein"
     /organism="Escherichia coli"

<400> SEQUENCE: 50

Met Ile Arg Thr Met Leu Gln Gly Lys Leu His Arg Val Lys Val Thr
1               5                   10                  15

His Ala Asp Leu His Tyr Glu Gly Ser Cys Ala Ile Asp Gln Asp Phe
            20                  25                  30

Leu Asp Ala Ala Gly Ile Leu Glu Asn Glu Ala Ile Asp Ile Trp Asn
        35                  40                  45

Val Thr Asn Gly Lys Arg Phe Ser Thr Tyr Ala Ile Ala Ala Glu Arg
    50                  55                  60

-continued

Gly Ser Arg Ile Ile Ser Val Asn Gly Ala Ala Ala His Cys Ala Ser
65                  70                  75                  80

Val Gly Asp Ile Val Ile Ile Ala Ser Phe Val Thr Met Pro Asp Glu
                85                  90                  95

Glu Ala Arg Thr Trp Arg Pro Asn Val Ala Tyr Phe Glu Gly Asp Asn
            100                 105                 110

Glu Met Lys Arg Thr Ala Lys Ala Ile Pro Val Gln Val Ala
        115                 120                 125

<210> SEQ ID NO 51
<211> LENGTH: 381
<212> TYPE: DNA
<213> ORGANISM: Escherichia coli
<220> FEATURE:
<221> NAME/KEY: source
<222> LOCATION: 1..381
<223> OTHER INFORMATION: /mol_type="DNA"
      /organism="Escherichia coli"
<220> FEATURE:
<221> NAME/KEY: misc_feature
<222> LOCATION: 1..381
<223> OTHER INFORMATION: /note="Codon optimised for S. cerevisiae"

<400> SEQUENCE: 51
atgatcagaa ccatgttgca aggtaaattg cacagagtta aggttactca tgctgacttg    60
cattacgaag gttcttgtgc tattgatcaa gatttcttgg atgctgccgg tatcttggaa   120
aatgaagcta ttgatatttg aacgtcacc aacggtaaga gattttctac ttatgctatt    180
gctgccgaaa gaggttccag aattatttct gttaatggtg ctgctgctca ttgtgcttca   240
gttggtgata tagttattat cgcctctttc gttaccatgc cagatgaaga agctagaact   300
tggagaccaa atgttgctta ctttgaaggt gacaacgaaa tgaagagaac cgctaaagct   360
attccagttc aagttgcttg a                                             381

<210> SEQ ID NO 52
<211> LENGTH: 136
<212> TYPE: PRT
<213> ORGANISM: Corynebacterium glutamicum
<220> FEATURE:
<221> NAME/KEY: SOURCE
<222> LOCATION: 1..136
<223> OTHER INFORMATION: /mol_type="protein"
      /organism="Corynebacterium glutamicum"

<400> SEQUENCE: 52

Met Leu Arg Thr Ile Leu Gly Ser Lys Ile His Arg Ala Thr Val Thr
1               5                   10                  15

Gln Ala Asp Leu Asp Tyr Val Gly Ser Val Thr Ile Asp Ala Asp Leu
            20                  25                  30

Val His Ala Ala Gly Leu Ile Glu Gly Lys Val Ala Ile Val Asp
            35                  40                  45

Ile Thr Asn Gly Ala Arg Leu Glu Thr Tyr Val Ile Val Gly Asp Ala
        50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
130             135

<210> SEQ ID NO 53
<211> LENGTH: 411
<212> TYPE: DNA
<213> ORGANISM: Corynebacterium glutamicum
<220> FEATURE:
<221> NAME/KEY: source
<222> LOCATION: 1..411
<223> OTHER INFORMATION: /mol_type="DNA"
      /organism="Corynebacterium glutamicum"
<220> FEATURE:
<221> NAME/KEY: misc_feature
<222> LOCATION: 1..411
<223> OTHER INFORMATION: /note="Codon optimised for S. cerevisiae"

<400> SEQUENCE: 53
atgttgagaa ccatcttggg ttccaagatt catagagcta ctgttactca agccgatttg      60
gattatgttg ttccgttac tattgatgct gatttggttc atgctgccgg tttgattgaa     120
ggtgaaaaag ttgctatcgt tgacattacc aatggtgcta gattggaaac ctatgttata     180
gttggtgatg ctggtactgg taacatctgt attaacggtg ctgctgctca tttgattaac     240
ccaggtgatt tggtcatcat catgtcttac ttgcaagcta ctgatgctga agctaaagct     300
tacgaaccta agatcgttca tgttgatgcc gataatagaa tcgttgcttt gggtaatgat     360
ttggctgaag ctttgccagg ttctggtttg ttgacttcta gatccatttg a              411

<210> SEQ ID NO 54
<211> LENGTH: 585
<212> TYPE: PRT
<213> ORGANISM: Saccharomyces cerevisiae
<220> FEATURE:
<221> NAME/KEY: SOURCE
<222> LOCATION: 1..585
<223> OTHER INFORMATION: /mol_type="protein"
      /organism="Saccharomyces cerevisiae"

<400> SEQUENCE: 54

Met Leu His Arg His Gly Ser Lys Gln Lys Asn Phe Glu Asn Ile Ala
1               5                   10                  15

Gly Lys Val Val His Asp Leu Ala Gly Leu Gln Leu Leu Ser Asn Asp
                20                  25                  30

Val Gln Lys Ser Ala Val Gln Ser Gly His Gln Gly Ser Asn Asn Met
            35                  40                  45

Arg Asp Thr Ser Ser Gln Gly Met Ala Asn Lys Tyr Ser Val Pro Lys
        50                  55                  60

Lys Gly Leu Pro Ala Asp Leu Ser Tyr Gln Leu Ile His Asn Glu Leu
65                  70                  75                  80

Thr Leu Asp Gly Asn Pro His Leu Asn Leu Ala Ser Phe Val Asn Thr
                85                  90                  95

Phe Thr Thr Asp Gln Ala Arg Lys Leu Ile Asp Glu Asn Leu Thr Lys
            100                 105                 110

Asn Leu Ala Asp Asn Asp Glu Tyr Pro Gln Leu Ile Glu Leu Thr Gln
        115                 120                 125

Arg Cys Ile Ser Met Leu Ala Gln Leu Trp His Ala Asn Pro Asp Glu
    130                 135                 140

Glu Pro Ile Gly Cys Ala Thr Thr Gly Ser Ser Glu Ala Ile Met Leu
145                 150                 155                 160

Gly Gly Leu Ala Met Lys Lys Arg Trp Glu His Arg Met Lys Asn Ala

-continued

```
                165                 170                 175
Gly Lys Asp Ala Ser Lys Pro Asn Ile Ile Met Ser Ser Ala Cys Gln
            180                 185                 190

Val Ala Leu Glu Lys Phe Thr Arg Tyr Phe Glu Val Glu Cys Arg Leu
        195                 200                 205

Val Pro Val Ser His Arg Ser His His Met Leu Asp Pro Glu Ser Leu
    210                 215                 220

Trp Asp Tyr Val Asp Glu Asn Thr Ile Gly Cys Phe Val Ile Leu Gly
225                 230                 235                 240

Thr Thr Tyr Thr Gly His Leu Glu Asn Val Glu Lys Val Ala Asp Val
                245                 250                 255

Leu Ser Gln Ile Glu Ala Lys His Pro Asp Trp Ser Asn Thr Asp Ile
            260                 265                 270

Pro Ile His Ala Asp Gly Ala Ser Gly Gly Phe Ile Ile Pro Phe Gly
        275                 280                 285

Phe Glu Lys Glu His Met Lys Ala Tyr Gly Met Glu Arg Trp Gly Phe
    290                 295                 300

Asn His Pro Arg Val Val Ser Met Asn Thr Ser Gly His Lys Phe Gly
305                 310                 315                 320

Leu Thr Thr Pro Gly Leu Gly Trp Val Leu Trp Arg Asp Glu Ser Leu
                325                 330                 335

Leu Ala Asp Glu Leu Arg Phe Lys Leu Lys Tyr Leu Gly Gly Val Glu
            340                 345                 350

Glu Thr Phe Gly Leu Asn Phe Ser Arg Pro Gly Phe Gln Val Val His
        355                 360                 365

Gln Tyr Phe Asn Phe Val Ser Leu Gly His Ser Gly Tyr Arg Thr Gln
    370                 375                 380

Phe Gln Asn Ser Leu Phe Val Ala Arg Ala Phe Ser Phe Glu Leu Leu
385                 390                 395                 400

Asn Ser Ser Lys Leu Pro Gly Cys Phe Glu Ile Val Ser Ser Ile His
                405                 410                 415

Glu Ser Ile Glu Asn Asp Ser Ala Pro Lys Ser Val Lys Asp Tyr Trp
            420                 425                 430

Glu His Pro Gln Ala Tyr Lys Pro Gly Val Pro Leu Val Ala Phe Lys
        435                 440                 445

Leu Ser Lys Lys Phe His Glu Glu Tyr Pro Glu Val Pro Gln Ala Ile
    450                 455                 460

Leu Ser Ser Leu Leu Arg Gly Arg Gly Trp Ile Ile Pro Asn Tyr Pro
465                 470                 475                 480

Leu Pro Lys Ala Thr Asp Gly Ser Asp Glu Lys Glu Val Leu Arg Val
                485                 490                 495

Val Phe Arg Ser Glu Met Lys Leu Asp Leu Ala Gln Leu Leu Ile Val
            500                 505                 510

Asp Ile Glu Ser Ile Leu Thr Lys Leu Ile His Ser Tyr Glu Lys Val
        515                 520                 525

Cys His His Ile Glu Leu Ala Ser Glu Gln Thr Pro Glu Arg Lys Ser
    530                 535                 540

Ser Phe Ile Tyr Glu Met Leu Leu Ala Leu Ala Ser Pro Gln Asp Asp
545                 550                 555                 560

Ile Pro Thr Pro Asp Glu Ile Glu Lys Lys Asn Lys Leu Lys Glu Thr
                565                 570                 575

Thr Thr Arg Asn Tyr Arg Gly Thr Cys
            580                 585
```

<210> SEQ ID NO 55
<211> LENGTH: 1758
<212> TYPE: DNA
<213> ORGANISM: Saccharomyces cerevisiae
<220> FEATURE:
<221> NAME/KEY: source
<222> LOCATION: 1..1758
<223> OTHER INFORMATION: /mol_type="DNA"
      /organism="Saccharomyces cerevisiae"

<400> SEQUENCE: 55

```
atgttacaca ggcacggttc taagcagaag aacttcgaga atatcgctgg aaaagttgtc      60
cacgaccttg caggtctgca attgctttct aacgacgttc aaaaatccgc tgtccaaagt     120
ggtcatcaag gatcgaacaa tatgagagat acttcgtctc agggcatggc taataagtat     180
tcagttccaa aaagggact acctgctgat tgtcttacc aactgattca taatgaatta      240
acacttgatg gtaatccgca tttgaacctt gccagtttcg tgaacacttt taccactgat     300
caggcaagga aattgattga tgaaaatttg accaaaaatc ttgctgacaa tgatgaatat     360
ccgcaattaa ttgagctaac tcagcgttgt atttctatgc tagctcaatt atggcacgct     420
aatcccgatg aagaaccaat aggctgtgcc accacaggtt ctagtgaggc aatcatgttg     480
ggtggactcg ccatgaaaaa agatgggaa cacagaatga agaatgctgg taaagatgct     540
tccaagccga acattataat gtcttctgcg tgccaagtgg cattagagaa gtttacgaga     600
tattttgaag tggaatgccg attggttccg gtatcccaca gaagccatca tatgcttgac     660
ccagagtcgt tatgggatta tgtagatgag aacactattg gctgttttgt aattttagga     720
accacctaca ctggccattt ggaaaatgta gagaaagttg cagatgtctt gtcccaaatt     780
gaggccaagc atcctgattg gagcaatact gatattccaa tccatgcgga tggcgcttca     840
ggtgggttta ttatcccatt tggctttgaa aaagagcaca tgaaagctta tggcatggaa     900
cgttgggggt tcaaccatcc gcgtgtggtt agtatgaaca ctagtggtca taagtttggc     960
ttaaccactc ccggtctggg ttgggtgcta tggagagatg aatccttact ggctgatgaa    1020
ttgagattca aactaaagta cctcggtggc gtggaagaaa cttcggttt gaattttca     1080
agacctggat ttcaagttgt ccatcaatac ttcaattttg tttctctagg ccattcaggg    1140
tatagaacac aattccaaaa ttctctattt gttgcaagag cgttttcttt cgaattattg    1200
aattcgtcaa aattgcccgg atgctttgaa attgttagca gtatccatga aagcattgag    1260
aacgattccg cccctaagtc agttaaagac tattgggaac accccaggc ttacaaacca    1320
ggtgtaccgc tggtagcctt caaattgtcc aagaaattcc acgaagaata tccagaagtg    1380
ccacaagcaa tcctttcctc tttactgaga ggtagggggtt ggataatacc aaattaccca    1440
ctaccaaagg caacggatgg atccgatgag aaggaggtat taagagtggt tttcagatcg    1500
gagatgaagt tggatttagc acagttgttg atcgttgaca tcgagagtat cttgacaaag    1560
ttgattcata gttacgaaaa ggtttgtcat catatagaac ttgcctctga gcaaactcca    1620
gagcgcaaga gttcgttcat ctacgaaatg ttgctggcat tggcatctcc acaagatgac    1680
atcccaacgc cggatgaaat cgaaaagaaa aataagctaa aggaaacaac aacgagaaac    1740
tatagaggaa catgttga                                                 1758
```

<210> SEQ ID NO 56
<211> LENGTH: 466
<212> TYPE: PRT
<213> ORGANISM: Escherichia coli

```
<220> FEATURE:
<221> NAME/KEY: SOURCE
<222> LOCATION: 1..466
<223> OTHER INFORMATION: /mol_type="protein"
      /organism="Escherichia coli"

<400> SEQUENCE: 56
```

Met Asp Gln Lys Leu Leu Thr Asp Phe Arg Ser Glu Leu Leu Asp Ser
1               5                   10                  15

Arg Phe Gly Ala Lys Ala Ile Ser Thr Ile Ala Glu Ser Lys Arg Phe
            20                  25                  30

Pro Leu His Glu Met Arg Asp Asp Val Ala Phe Gln Ile Ile Asn Asp
        35                  40                  45

Glu Leu Tyr Leu Asp Gly Asn Ala Arg Gln Asn Leu Ala Thr Phe Cys
    50                  55                  60

Gln Thr Trp Asp Asp Glu Asn Val His Lys Leu Met Asp Leu Ser Ile
65                  70                  75                  80

Asn Lys Asn Trp Ile Asp Lys Glu Gly Tyr Pro Gln Ser Ala Ala Ile
                85                  90                  95

Asp Leu Arg Cys Val Asn Met Val Ala Asp Leu Trp His Ala Pro Ala
            100                 105                 110

Pro Lys Asn Gly Gln Ala Val Gly Thr Asn Thr Ile Gly Ser Ser Glu
        115                 120                 125

Ala Cys Met Leu Gly Gly Met Ala Met Lys Trp Arg Trp Arg Lys Arg
130                 135                 140

Met Glu Ala Ala Gly Lys Pro Thr Asp Lys Pro Asn Leu Val Cys Gly
145                 150                 155                 160

Pro Val Gln Ile Cys Trp His Lys Phe Ala Arg Tyr Trp Asp Val Glu
                165                 170                 175

Leu Arg Glu Ile Pro Met Arg Pro Gly Gln Leu Phe Met Asp Pro Lys
            180                 185                 190

Arg Met Ile Glu Ala Cys Asp Glu Asn Thr Ile Gly Val Val Pro Thr
        195                 200                 205

Phe Gly Val Thr Tyr Thr Gly Asn Tyr Glu Phe Pro Gln Pro Leu His
    210                 215                 220

Asp Ala Leu Asp Lys Phe Gln Ala Asp Thr Gly Ile Asp Ile Asp Met
225                 230                 235                 240

His Ile Asp Ala Ala Ser Gly Gly Phe Leu Ala Pro Phe Val Ala Pro
                245                 250                 255

Asp Ile Val Trp Asp Phe Arg Leu Pro Arg Val Lys Ser Ile Ser Ala
            260                 265                 270

Ser Gly His Lys Phe Gly Leu Ala Pro Leu Gly Cys Gly Trp Val Ile
        275                 280                 285

Trp Arg Asp Glu Glu Ala Leu Pro Gln Glu Leu Val Phe Asn Val Asp
    290                 295                 300

Tyr Leu Gly Gly Gln Ile Gly Thr Phe Ala Ile Asn Phe Ser Arg Pro
305                 310                 315                 320

Ala Gly Gln Val Ile Ala Gln Tyr Tyr Glu Phe Leu Arg Leu Gly Arg
                325                 330                 335

Glu Gly Tyr Thr Lys Val Gln Asn Ala Ser Tyr Gln Val Ala Ala Tyr
            340                 345                 350

Leu Ala Asp Glu Ile Ala Lys Leu Gly Pro Tyr Glu Phe Ile Cys Thr
        355                 360                 365

Gly Arg Pro Asp Glu Gly Ile Pro Ala Val Cys Phe Lys Leu Lys Asp
    370                 375                 380

```
Gly Glu Asp Pro Gly Tyr Thr Leu Tyr Asp Leu Ser Glu Arg Leu Arg
385                 390                 395                 400

Leu Arg Gly Trp Gln Val Pro Ala Phe Thr Leu Gly Gly Glu Ala Thr
            405                 410                 415

Asp Ile Val Val Met Arg Ile Met Cys Arg Arg Gly Phe Glu Met Asp
                420                 425                 430

Phe Ala Glu Leu Leu Leu Glu Asp Tyr Lys Ala Ser Leu Lys Tyr Leu
            435                 440                 445

Ser Asp His Pro Lys Leu Gln Gly Ile Ala Gln Gln Asn Ser Phe Lys
    450                 455                 460

His Thr
465

<210> SEQ ID NO 57
<211> LENGTH: 1401
<212> TYPE: DNA
<213> ORGANISM: Escherichia coli
<220> FEATURE:
<221> NAME/KEY: source
<222> LOCATION: 1..1401
<223> OTHER INFORMATION: /mol_type="DNA"
      /organism="Escherichia coli"

<400> SEQUENCE: 57
```

| | | | | | |
|---|---|---|---|---|---|
| atggaccaga | agctgttaac | ggatttccgc | tcagaactac | tcgattcacg | ttttggcgca | 60 |
| aaggccattt | ctactatcgc | ggagtcaaaa | cgatttccgc | tgcacgaaat | gcgcgatgat | 120 |
| gtcgcatttc | agattatcaa | tgatgaatta | tatcttgatg | caacgctcg | tcagaacctg | 180 |
| gccactttct | gccagacctg | ggacgacgaa | aacgtccata | aattgatgga | tttgtcgatc | 240 |
| aataaaaact | ggatcgacaa | agaagaatat | ccgcaatccg | cagccatcga | cctgcgttgc | 300 |
| gtaaatatgg | ttgccgatct | gtggcatgcg | cctgcgccga | aaatggtca | ggccgttggc | 360 |
| accaacacca | ttggttcttc | cgaggcctgt | atgctcggcg | gatggcgat | gaaatggcgt | 420 |
| tggcgcaagc | gtatggaagc | tgcaggcaaa | ccaacggata | aaccaaacct | ggtgtgcggt | 480 |
| ccggtacaaa | tctgctggca | taaattcgcc | cgctactggg | atgtggagct | gcgtgagatc | 540 |
| cctatgcgcc | ccggtcagtt | gtttatggac | ccgaaacgca | tgattgaagc | ctgtgacgaa | 600 |
| aacaccatcg | gcgtggtgcc | gactttcggc | gtgacctaca | ccgtaacta | tgagttccca | 660 |
| caaccgctgc | acgatgcgct | ggataaattc | caggccgaca | ccggtatcga | catcgacatg | 720 |
| cacatcgacg | ctgccagcgg | tggcttcctg | gcaccgttcg | tcgccccgga | tatcgtctgg | 780 |
| gacttccgcc | tgccgcgtgt | gaaatcgatc | agtgcttcag | gccataaatt | cggtctggct | 840 |
| ccgctgggct | gcggctgggt | tatctggcgt | gacgaagaag | cgctgccgca | ggaactggtg | 900 |
| ttcaacgttg | actacctggg | tggtcaaatt | ggtacttttg | ccatcaactt | ctcccgcccg | 960 |
| gcgggtcagg | taattgcaca | gtactatgaa | ttcctgcgcc | tcggtcgtga | aggctatacc | 1020 |
| aaagtacaga | acgcctctta | ccaggttgcc | gcttatctgg | cggatgaaat | cgccaaactg | 1080 |
| gggccgtatg | agttcatctg | tacgggtcgc | ccggacgaag | gcatcccggc | ggtttgcttc | 1140 |
| aaactgaaag | atggtgaaga | tccgggatac | accctgtacg | acctctctga | acgtctgcgt | 1200 |
| ctgcgcggct | ggcaggttcc | ggccttcact | ctcggcggtg | aagccaccga | catcgtggtg | 1260 |
| atgcgcatta | tgtgtcgtcg | cggcttcgaa | atggactttg | ctgaactgtt | gctggaagac | 1320 |
| tacaaagcct | ccctgaaata | tctcagcgat | caccgaaac | tgcagggtat | tgcccagcag | 1380 |
| aacagcttta | aacacacctg | a | | | | 1401 |

<210> SEQ ID NO 58
<211> LENGTH: 593
<212> TYPE: PRT
<213> ORGANISM: Rattus norvegicus
<220> FEATURE:
<221> NAME/KEY: SOURCE
<222> LOCATION: 1..593
<223> OTHER INFORMATION: /mol_type="protein"
      /organism="Rattus norvegicus"

<400> SEQUENCE: 58

```
Met Ala Ser Ser Thr Pro Ser Pro Ala Thr Ser Ser Asn Ala Gly Ala
1               5                   10                  15

Asp Pro Asn Thr Thr Asn Leu Arg Pro Thr Thr Tyr Asp Thr Trp Cys
            20                  25                  30

Gly Val Ala His Gly Cys Thr Arg Lys Leu Gly Leu Lys Ile Cys Gly
        35                  40                  45

Phe Leu Gln Arg Thr Asn Ser Leu Glu Glu Lys Ser Arg Leu Val Ser
    50                  55                  60

Ala Phe Arg Glu Arg Gln Ala Ser Lys Asn Leu Leu Ser Cys Glu Asn
65                  70                  75                  80

Ser Asp Pro Gly Ala Arg Phe Arg Arg Thr Glu Thr Asp Phe Ser Asn
                85                  90                  95

Leu Phe Ala Gln Asp Leu Leu Pro Ala Lys Asn Gly Glu Glu Gln Thr
            100                 105                 110

Val Gln Phe Leu Leu Glu Val Val Asp Ile Leu Leu Asn Tyr Val Arg
        115                 120                 125

Lys Thr Phe Asp Arg Ser Thr Lys Val Leu Asp Phe His His Pro His
    130                 135                 140

Gln Leu Leu Glu Gly Met Glu Gly Phe Asn Leu Glu Leu Ser Asp His
145                 150                 155                 160

Pro Glu Ser Leu Glu Gln Ile Leu Val Asp Cys Arg Asp Thr Leu Lys
                165                 170                 175

Tyr Gly Val Arg Thr Gly His Pro Arg Phe Phe Asn Gln Leu Ser Thr
            180                 185                 190

Gly Leu Asp Ile Ile Gly Leu Ala Gly Glu Trp Leu Thr Ser Thr Ala
        195                 200                 205

Asn Thr Asn Met Phe Thr Tyr Glu Ile Ala Pro Val Phe Val Leu Met
    210                 215                 220

Glu Gln Ile Thr Leu Lys Lys Met Arg Glu Ile Ile Gly Trp Ser Asn
225                 230                 235                 240

Lys Asp Gly Asp Gly Ile Phe Ser Pro Gly Gly Ala Ile Ser Asn Met
                245                 250                 255

Tyr Ser Ile Met Ala Ala Arg Tyr Lys Tyr Phe Pro Glu Val Lys Thr
            260                 265                 270

Lys Gly Met Ala Ala Val Pro Lys Leu Val Leu Phe Thr Ser Glu His
        275                 280                 285

Ser His Tyr Ser Ile Lys Lys Ala Gly Ala Ala Leu Gly Phe Gly Thr
    290                 295                 300

Asp Asn Val Ile Leu Ile Lys Cys Asn Glu Arg Gly Lys Ile Ile Pro
305                 310                 315                 320

Ala Asp Leu Glu Ala Lys Ile Leu Asp Ala Lys Gln Lys Gly Phe Val
                325                 330                 335

Pro Leu Tyr Val Asn Ala Thr Ala Gly Thr Thr Val Tyr Gly Ala Phe
            340                 345                 350
```

Asp Pro Ile Gln Glu Ile Ala Asp Ile Cys Glu Lys Tyr Asn Leu Trp
         355                 360                 365

Leu His Val Asp Ala Ala Trp Gly Gly Gly Leu Leu Met Ser Arg Lys
     370                 375                 380

His Arg His Lys Leu Ser Gly Ile Glu Arg Ala Asn Ser Val Thr Trp
385                 390                 395                 400

Asn Pro His Lys Met Met Gly Val Leu Leu Gln Cys Ser Ala Ile Leu
                 405                 410                 415

Val Lys Glu Lys Gly Ile Leu Gln Gly Cys Asn Gln Met Cys Ala Gly
             420                 425                 430

Tyr Leu Phe Gln Pro Asp Lys Gln Tyr Asp Val Ser Tyr Asp Thr Gly
         435                 440                 445

Asp Lys Ala Ile Gln Cys Gly Arg His Val Asp Ile Phe Lys Phe Trp
     450                 455                 460

Leu Met Trp Lys Ala Lys Gly Thr Val Gly Phe Glu Asn Gln Ile Asn
465                 470                 475                 480

Lys Cys Leu Glu Leu Ala Glu Tyr Leu Tyr Ala Lys Ile Lys Asn Arg
                 485                 490                 495

Glu Glu Phe Glu Met Val Phe Asn Gly Glu Pro Glu His Thr Asn Val
             500                 505                 510

Cys Phe Trp Tyr Ile Pro Gln Ser Leu Arg Gly Val Pro Asp Ser Pro
         515                 520                 525

Glu Arg Arg Glu Lys Leu His Arg Val Ala Pro Lys Ile Lys Ala Leu
     530                 535                 540

Met Met Glu Ser Gly Thr Thr Met Val Gly Tyr Gln Pro Gln Gly Asp
545                 550                 555                 560

Lys Ala Asn Phe Phe Arg Met Val Ile Ser Asn Pro Ala Ala Thr Gln
                 565                 570                 575

Ser Asp Ile Asp Phe Leu Ile Glu Glu Ile Glu Arg Leu Gly Gln Asp
             580                 585                 590

Leu

<210> SEQ ID NO 59
<211> LENGTH: 1782
<212> TYPE: DNA
<213> ORGANISM: Rattus norvegicus
<220> FEATURE:
<221> NAME/KEY: source
<222> LOCATION: 1..1782
<223> OTHER INFORMATION: /mol_type="DNA"
     /organism="Rattus norvegicus"
<220> FEATURE:
<221> NAME/KEY: misc_feature
<222> LOCATION: 1..1782
<223> OTHER INFORMATION: /note="Codon optimised for S. cerevisiae"

<400> SEQUENCE: 59
atggcttctt ctactccatc tccagctaca tcttctaatg ctggtgctga tccaaatacc      60
actaacttaa gaccaactac ttacgatact tggtgtggtg ttgctcatgg ttgtactaga     120
aaattgggtt tgaagatctg cggtttcttg caaagaacta actccttgga agaaaagtcc     180
agattggttt ctgctttcag agaaagacaa gcctctaaga acttgttgtc ttgcgaaaat     240
tctgatccag gtgctagatt cagaagaact gaaactgatt tctccaactt gttcgcccaa     300
gatttgttgc cagctaaaaa tggtgaagaa caaccgtccc aattcttgtt ggaagttgtt     360
gacatcttgt tgaactacgt cagaaagacc tttgacagat ctaccaaggt tttggatttc     420

```
catcatccac accaattatt ggaaggtatg gaaggtttca acttggaatt gtctgatcac    480
ccagaatcct tggaacaaat tttggttgat tgcagagaca ccttgaagta cggtgttaga    540
actggtcatc caagattctt caatcaattg tctaccggtt tggacattat tggtttggct    600
ggtgaatggt tgacttctac tgctaacact aacatgttca cctacgaaat tgctccagtt    660
ttcgtcttga tggaacaaat cactttgaag aagatgagag aaatcatcgg ttggtctaac    720
aaagatggtg atggtatttt ttcaccaggt ggtgctattt ccaacatgta ctctattatg    780
gctgccagat acaagtactt cccagaagtt aagacaaaag gtatggctgc tgttccaaag    840
ttggttttgt ttacctctga acactccccac tactccatta agaaagctgg tgcagctttg   900
ggtttcggta ctgataatgt tattttgatc aagtgcaacg aaagaggtaa gattattcca    960
gctgatttgg aagccaagat tttggacgct aaacaaaagg gtttcgtccc attatacgtt   1020
aatgctactg ctggtactac tgtttacggt gcttttgatc caattcaaga aattgccgat   1080
atctgcgaaa agtacaactt gtggttgcat gttgatgctg cttggggtgg tggtttgttg   1140
atgtctagaa aacatagaca caaattgtcc ggtatcgaaa gagctaattc tgttacttgg   1200
aacccacata agatgatggg tgttttgttg caatgctctg ccatttttggt caaagaaaag   1260 ggtatattgc aaggttgcaa tcaaatgtgt gctggttact tgtttcaacc agataagcaa   1320
tacgatgtct cctatgatac tggtgataag gctattcaat gcggtagaca tgttgatatc   1380
ttcaagttct ggttgatgtg gaaagctaaa ggtactgtcg gtttcgaaaa tcaaatcaac   1440
aagtgtttgg aattggccga atacttgtac gctaagatca agaacagaga agaattcgaa   1500
atggttttca acggtgaacc agaacatacc aatgtttgtt tctggtacat cccacaatct   1560
ttgagaggtg ttccagattc tccagaaaga agagaaaagt tgcatagagt tgccccaaag   1620
attaaggctt taatgatgga atctggtaca actatggtcg gttatcaacc tcaaggtgac   1680
aaggctaatt tcttcagaat ggttatttct aacccagctg ctacccaatc cgatattgat   1740
tttttgatcg aagaaatcga agattgggt caagatttgt ga                        1782
```

<210> SEQ ID NO 60
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="DNA"
      /note="synthetic primer"
      /organism="Artificial Sequence"
<220> FEATURE:
<221> NAME/KEY: misc_RNA
<222> LOCATION: 9..9
<223> OTHER INFORMATION: /note="uracil"

<400> SEQUENCE: 60
atctgtcatg gtaccaaaac aatg                                             24

<210> SEQ ID NO 61
<211> LENGTH: 17
<212> TYPE: DNA
<213> ORGANISM: Artificial Sequence
<220> FEATURE:
<221> NAME/KEY: source
<222> LOCATION: 1..17
<223> OTHER INFORMATION: /mol_type="DNA"
      /note="synthetic primer"
      /organism="Artificial Sequence"
<220> FEATURE:
<221> NAME/KEY: misc_RNA

```
<222> LOCATION: 8..8
<223> OTHER INFORMATION: /note="uracil"

<400> SEQUENCE: 61
cacgcgatgt cgactca                                                  17

<210> SEQ ID NO 62
<211> LENGTH: 37
<212> TYPE: DNA
<213> ORGANISM: Artificial Sequence
<220> FEATURE:
<221> NAME/KEY: source
<222> LOCATION: 1..37
<223> OTHER INFORMATION: /mol_type="DNA"
      /note="synthetic primer"
      /organism="Artificial Sequence"
<220> FEATURE:
<221> NAME/KEY: misc_RNA
<222> LOCATION: 9..9
<223> OTHER INFORMATION: /note="uracil"

<400> SEQUENCE: 62
atctgtcata aaacaatgat cgttttagta actggag                            37

<210> SEQ ID NO 63
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="DNA"
      /note="synthetic primer"
      /organism="Artificial Sequence"
<220> FEATURE:
<221> NAME/KEY: misc_RNA
<222> LOCATION: 8..8
<223> OTHER INFORMATION: /note="uracil"

<400> SEQUENCE: 63
cacgcgattt actgacggtg gacattc                                       27

<210> SEQ ID NO 64
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="DNA"
      /note="synthetic primer"
      /organism="Artificial Sequence"
<220> FEATURE:
<221> NAME/KEY: misc_RNA
<222> LOCATION: 9..9
<223> OTHER INFORMATION: /note="uracil"

<400> SEQUENCE: 64
acctgcactt tgtaattaaa acttag                                        26

<210> SEQ ID NO 65
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="DNA"
      /note="Synthetic primer"
      /organism="Artificial Sequence"
<220> FEATURE:
```

```
<221> NAME/KEY: misc_RNA
<222> LOCATION: 9..9
<223> OTHER INFORMATION: /note="uracil"

<400> SEQUENCE: 65
atgacagatt tgttttatat ttgttg                                          26

<210> SEQ ID NO 66
<211> LENGTH: 1404
<212> TYPE: DNA
<213> ORGANISM: Saccharomyces cerevisiae
<220> FEATURE:
<221> NAME/KEY: source
<222> LOCATION: 1..1404
<223> OTHER INFORMATION: /mol_type="DNA"
      /organism="Saccharomyces cerevisiae"

<400> SEQUENCE: 66
ttgtaattaa aacttagatt agattgctat gctttctttc taatgagcaa gaagtaaaaa      60
aagttgtaat agaacaagaa aaatgaaact gaaacttgag aaattgaaga ccgtttatta     120
acttaaatat caatgggagg tcatcgaaag agaaaaaaat caaaaaaaaa aattttcaag     180
aaaaagaaac gtgataaaaa ttttattgc cttttcgac gaagaaaag aaacgaggcg        240 gtctcttttt tcttttccaa acctttagta cgggtaatta acgacaccct agaggaagaa     300
agaggggaaa tttagtatgc tgtgcttggg tgttttgaag tggtacggcg atgcgcggag     360
tccgagaaaa tctggaagag taaaaaagga gtagaaacat tttgaagcta tggtgtgtgc     420
ggaagtacct tcaaagaatg gggtcttatc ttgttttgca agtaccactg agcaggataa     480
taatagaaat gataatatac tatagtagag ataacgtcga tgacttccca tactgtaatt     540
gcttttagtt gtgtattttt agtgtgcaag tttctgtaaa tcgattaatt tttttttctt     600
tcctcttttt attaaccta attttttattt tagattcctg acttcaactc aagacgcaca    660
gatattataa catctgcata ataggcattt gcaagaatta ctcgtgagta aggaaagagt     720
gaggaactat cgcatacctg catttaaaga tgccgatttg ggcgcgaatc ctttattttg     780
gcttcaccct catactatta tcagggccag aaaaaggaag tgtttccctc cttcttgaat     840
tgatgttacc ctcataaagc acgtggcctc ttatcgagaa agaaattacc gtcgctcgtg     900
atttgtttgc aaaaagaaca aaactgaaaa aacccagaca cgctcgactt cctgtcttcc     960
tattgattgc agcttccaat ttcgtcacac aacaaggtcc tagcgacggc tcacaggttt    1020
tgtaacaagc aatcgaaggt tctggaatgg cgggaagggg tttagtacca catgctatga    1080
tgcccactgt gatctccaga gcaaagttcg ttcgatcgta ctgttactct ctctctttca    1140
aacagaattg tccgaatcgt gtgacaacaa cagcctgttc tcacacactc ttttcttcta    1200
accaaggggg tggtttagtt tagtagaacc tcgtgaaact tacatttaca tatatataaa    1260
cttgcataaa ttggtcaatg caagaaatac atatttggtc ttttctaatt cgtagttttt    1320
caagttctta gatgctttct ttttctcttt tttacagatc atcaaggaag taattatcta    1380 cttttttacaa caaatataaa acaa                                           1404

<210> SEQ ID NO 67
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="DNA"
      /note="general formula for gene construct"
```

-continued

```
       /organism="Artificial Sequence"
<220>  FEATURE:
<221>  NAME/KEY: misc_structure
<222>  LOCATION: 16..19
<223>  OTHER INFORMATION: /note="variable number of variable nucleotide
       bases"
<220>  FEATURE:
<221>  NAME/KEY: misc_feature
<222>  LOCATION: 16..19
<223>  OTHER INFORMATION: /note="n is a, c, g, or t"
<220>  FEATURE:
<221>  NAME/KEY: gene
<222>  LOCATION: 16
<223>  OTHER INFORMATION: /gene="Gene encoding chosen protein"

<400>  SEQUENCE: 67 ggtaccaaaa caatgnnnnt gagtcgac                                            28

<210>  SEQ ID NO 68
<211>  LENGTH: 540
<212>  TYPE: PRT
<213>  ORGANISM: Tribolium castaneum
<220>  FEATURE:
<221>  NAME/KEY: SOURCE
<222>  LOCATION: 1..540
<223>  OTHER INFORMATION: /mol_type="protein"
       /organism="Tribolium castaneum"

<400>  SEQUENCE: 68
```

Met Pro Ala Thr Gly Glu Asp Gln Asp Leu Val Gln Asp Leu Ile Glu
1               5                   10                  15

Glu Pro Ala Thr Phe Ser Asp Ala Val Leu Ser Ser Asp Glu Glu Leu
            20                  25                  30

Phe His Gln Lys Cys Pro Lys Pro Ala Pro Ile Tyr Ser Pro Val Ser
        35                  40                  45

Lys Pro Val Ser Phe Glu Ser Leu Pro Asn Arg Arg Leu His Glu Glu
    50                  55                  60

Phe Leu Arg Ser Ser Val Asp Val Leu Leu Gln Glu Ala Val Phe Glu
65                  70                  75                  80

Gly Thr Asn Arg Lys Asn Arg Val Leu Gln Trp Arg Glu Pro Glu Glu
                85                  90                  95

Leu Arg Arg Leu Met Asp Phe Gly Val Arg Ser Ala Pro Ser Thr His
            100                 105                 110

Glu Glu Leu Leu Glu Val Leu Lys Lys Val Val Thr Tyr Ser Val Lys
        115                 120                 125

Thr Gly His Pro Tyr Phe Val Asn Gln Leu Phe Ser Ala Val Asp Pro
    130                 135                 140

Tyr Gly Leu Val Ala Gln Trp Ala Thr Asp Ala Leu Asn Pro Ser Val
145                 150                 155                 160

Tyr Thr Tyr Glu Val Ser Pro Val Phe Val Leu Met Glu Glu Val Val
                165                 170                 175

Leu Arg Glu Met Arg Ala Ile Val Gly Phe Glu Gly Gly Lys Gly Asp
            180                 185                 190

Gly Ile Phe Cys Pro Gly Gly Ser Ile Ala Asn Gly Tyr Ala Ile Ser
        195                 200                 205

Cys Ala Arg Tyr Arg Phe Met Pro Asp Ile Lys Lys Gly Leu His
    210                 215                 220

Ser Leu Pro Arg Leu Val Leu Phe Thr Ser Glu Asp Ala His Tyr Ser
225                 230                 235                 240

Ile Lys Lys Leu Ala Ser Phe Gln Gly Ile Gly Thr Asp Asn Val Tyr
                245                 250                 255

Leu Ile Arg Thr Asp Ala Arg Gly Arg Met Asp Val Ser His Leu Val
            260                 265                 270

Glu Glu Ile Glu Arg Ser Leu Arg Glu Gly Ala Ala Pro Phe Met Val
        275                 280                 285

Ser Ala Thr Ala Gly Thr Thr Val Ile Gly Ala Phe Asp Pro Ile Glu
        290                 295                 300

Lys Ile Ala Asp Val Cys Gln Lys Tyr Lys Leu Trp Leu His Val Asp
305                 310                 315                 320

Ala Ala Trp Gly Gly Gly Ala Leu Val Ser Ala Lys His Arg His Leu
                325                 330                 335

Leu Lys Gly Ile Glu Arg Ala Asp Ser Val Thr Trp Asn Pro His Lys
            340                 345                 350

Leu Leu Thr Ala Pro Gln Gln Cys Ser Thr Leu Leu Leu Arg His Glu
        355                 360                 365

Gly Val Leu Ala Glu Ala His Ser Thr Asn Ala Ala Tyr Leu Phe Gln
    370                 375                 380

Lys Asp Lys Phe Tyr Asp Thr Lys Tyr Asp Thr Gly Asp Lys His Ile
385                 390                 395                 400

Gln Cys Gly Arg Arg Ala Asp Val Leu Lys Phe Trp Phe Met Trp Lys
                405                 410                 415

Ala Lys Gly Thr Ser Gly Leu Glu Lys His Val Asp Lys Val Phe Glu
            420                 425                 430

Asn Ala Arg Phe Phe Thr Asp Cys Ile Lys Asn Arg Glu Gly Phe Glu
        435                 440                 445

Met Val Ile Ala Glu Pro Glu Tyr Thr Asn Ile Cys Phe Trp Tyr Val
    450                 455                 460

Pro Lys Ser Leu Arg Gly Arg Lys Asp Glu Ala Asp Tyr Lys Asp Lys
465                 470                 475                 480

Leu His Lys Val Ala Pro Arg Ile Lys Glu Arg Met Met Lys Glu Gly
                485                 490                 495

Ser Met Met Val Thr Tyr Gln Ala Gln Lys Gly His Pro Asn Phe Phe
            500                 505                 510

Arg Ile Val Phe Gln Asn Ser Gly Leu Asp Lys Ala Asp Met Val His
        515                 520                 525

Leu Val Glu Glu Ile Glu Arg Leu Gly Ser Asp Leu
    530                 535                 540

<210> SEQ ID NO 69
<211> LENGTH: 1623
<212> TYPE: DNA
<213> ORGANISM: Tribolium castaneum
<220> FEATURE:
<221> NAME/KEY: source
<222> LOCATION: 1..1623
<223> OTHER INFORMATION: /mol_type="DNA"
    /note="codon optimised for Saccharomyces cerevisiae"
    /organism="Tribolium castaneum"

<400> SEQUENCE: 69
atgccagcta ctggtgaaga tcaagatttg gttcaagact tgattgaaga accagctact    60
ttctccgatg ctgttttatc ttccgacgaa gaattattcc atcaaaagtg tccaaaacca   120
gccccaatct attctccagt tctaagcca gtttccttcg aatctttgcc aaatagaaga   180
ttgcatgaag aatttttgag atcctccgtt gacgtcttgt tgcaagaagc tgttttgaa   240 ggtacaaaca gaaagaacag agtcttgcaa tggagagaac cagaagaatt gagaagattg   300

```
atggatttcg tgttagatc tgctccatct acccatgaag aattattgga agttttgaag      360
aaggtcgtca cctactctgt taagactggt catccatact tcgtcaatca attattctct      420
gccgttgatc catatggttt ggttgctcaa tgggctactg atgctttgaa tccatctgtt      480
tacacctacg aagtttcccc agttttgtc ttgatggaag aagttgtctt gagagaaatg       540
agagctatcg ttggtttcga aggtggtaaa ggtgatggta ttttttgtcc aggtggttct      600
attgctaacg gttacgctat ttcttgtgcc agatatagat tcatgccaga cattaagaag      660
aagggtttac actcattgcc aagattggtt ttgttcacct ctgaagatgc tcactactct      720
atcaaaaagt tggcttcatt ccaaggtatc ggtactgata acgtttactt gattagaacc      780
gatgccagag gtagaatgga tgtttctcat ttggttgaag aaatcgaaag atcattgaga      840
gaaggtgctg ctcctttat ggtttctgct actgctggta ctactgttat tggtgctttt       900
gatccaattg aaaagatcgc cgatgtttgc caaaagtaca aattgtggtt gcatgttgat      960
gctgcttggg gtggtggtgc tttggtttca gctaaacata gacatttgtt gaagggtatc     1020
gaaagagctg attctgttac ttggaatcca cataagttgt tgactgctcc acaacaatgt     1080
tctaccttgt tgttgagaca tgaaggtgtt ttggctgaag ctcattctac taatgctgct     1140
tacttgttcc aaaaggacaa gttctacgat accaagtatg atactggtga caagcacatt     1200
caatgtggta agagagcaga tgttttgaag ttttggttta tgtggaaggc caaaggtact     1260
tccggtttgg aaaaacatgt tgacaaggtt tttgaaaacg ccagattctt caccgactgc     1320
atcaagaata gagaaggttt cgaaatggtt atcgccgaac cagaatacac caatatttgt     1380
ttctggtacg tcccaaagtc tttgagaggt agaaaagatg aagctgacta caaggataag     1440
ttgcataagg ttgctccaag aatcaaagaa agaatgatga aggaaggttc catgatggtt     1500
acttaccaag ctcaaaaagg tcacccaaat ttcttcagaa tcgttttcca aaactctggt     1560
ttggataagg ccgatatggt tcacttagtc gaagaaattg aaagattggg ttccgatttg     1620
tga                                                                   1623
```

<210> SEQ ID NO 70
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="DNA"
      /note="primer for PanD"
      /organism="Artificial Sequence"

<400> SEQUENCE: 70
agtgcaggta aaacaatgcc agctactggt g                                      31

<210> SEQ ID NO 71
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="DNA"
      /note="Primer for PanD"
      /organism="Artificial Sequence"

<400> SEQUENCE: 71
cgtgcgattc acaaatcgga acccaatc                                          28

```
<210> SEQ ID NO 72
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Primer"
      /organism="Artificial Sequence"

<400> SEQUENCE: 72
agtgcaggta aaacaatgtc gcaaagaaaa ttcg                                 34

<210> SEQ ID NO 73
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="DNA"
      /note="Primer"
      /organism="Artificial Sequence"

<400> SEQUENCE: 73
cgtgcgattc atgccttagt ttcaacag                                       28

<210> SEQ ID NO 74
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="DNA"
      /note="Primer"
      /organism="Artificial Sequence"

<400> SEQUENCE: 74
atctgtcata aaacaatgag cagtagcaag aaattg                              36

<210> SEQ ID NO 75
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="DNA"
      /note="Primer"
      /organism="Artificial Sequence"

<400> SEQUENCE: 75
cacgcgattt actttttttg ggatggg                                        27

<210> SEQ ID NO 76
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Primer"
      /organism="Artificial Sequence"

<400> SEQUENCE: 76
agtgcaggta aaacaatgtc tgccactctg ttca                                34
```

<210> SEQ ID NO 77
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="DNA"
    /note="Primer"
    /organism="Artificial Sequence"

<400> SEQUENCE: 77
cgtgcgattt acaatttagc ttcaatagta tag                        33

<210> SEQ ID NO 78
<211> LENGTH: 3537
<212> TYPE: DNA
<213> ORGANISM: Saccharomyces cerevisiae
<220> FEATURE:
<221> NAME/KEY: source
<222> LOCATION: 1..3537
<223> OTHER INFORMATION: /mol_type="DNA"
    /organism="Saccharomyces cerevisiae"

<400> SEQUENCE: 78
atgtcgcaaa gaaaattcgc cggcttgaga gataacttca atctcttggg tgaaaagaac      60
aaaatattgg tggctaatag aggagaaatt ccaatcagaa tttttcgtac cgctcatgaa     120
ctgtctatgc agacggtagc tatatattct catgaagatc gtctttcaac gcacaaacaa     180
aaggctgacg aagcatacgt cataggtgaa gtaggccaat ataccccgt cggcgcttat      240 ttggccattg acgaaatcat ttccattgcc caaaacacc aggtagattt catccatcca      300
ggttatgggt tcttgtctga aaattcggaa tttgccgaca agtagtgaa ggccggtatc      360 acttggattg cccctccagc tgaagttatt gactccgtgg gtgataaggt ctcagctaga     420
aacctggcag caaaagctaa tgtgcccacc gttcctggta caccaggtcc tatagaaact      480
gtagaggaag cacttgactt cgtcaatgaa tacggctacc cggtgatcat taaggccgcc     540
tttggtggtg gtggtagagg tatgagagtc gttagagaag gtgacgacgt ggcagatgcc     600
tttcaacgtg ctacctccga agcccgtact gccttcggta atggtacctg ctttgtggaa     660
agattcttgg acaagccaaa gcatattgaa gttcaattgt tggccgataa ccacggaaac      720
gtggttcatc ttttcgaaag agactgttcc gtgcagagaa gacaccaaaa ggttgtcgaa     780
gtggccccag caaagacttt accccgtgaa gtccgtgacg ccattttgac agatgcagtt     840
aaattggcca agagtgtgg ctacagaaat gcgggtactg ctgaattctt ggttgataac       900
caaaatagac actatttcat tgaaattaat ccaagaatcc aagtggaaca taccatcaca      960
gaagaaatta ccggtataga tattgtggcg gctcagatcc aaattgcggc aggtgcctct    1020 ctacccccagc tgggcctatt ccaggacaaa attacgactc gtggctttgc cattcagtgc    1080
cgtattacca cggaagaccc tgctaagaac ttccaaccag ataccggtag aatagaagtg    1140
taccgttctg caggtggtaa tggtgttaga ctggatggtg gtaacgccta tgcaggaaca    1200
ataatctcac tcattacga ctcaatgctg tcaaatgct catgctccgg ttccacctac     1260
gaaatcgttc gtagaaaaat gattcgtgca ttaatcgagt tcagaattag aggtgtcaag    1320
accaacattc ccttcctatt gactcttttg accaatccag tatttattga gggtacatac    1380
tggacgactt ttattgacga cacccacaa ctgttccaaa tggtttcatc acaaaacaga     1440
gcccaaaaac ttttacatta cctcgccgac gtggcagtca atggttcatc tatcaagggt    1500

| | |
|---|---|
| caaattggct tgccaaaatt aaaatcaaat ccaagtgtcc cccatttgca cgatgctcag | 1560 |
| ggcaatgtca tcaacgttac aaagtctgca ccaccatccg gatggaggca agtgctacta | 1620 |
| gaaaaggggc cagctgaatt tgccagacaa gttagacagt tcaatggtac tttattgatg | 1680 |
| gacaccacct ggagagacgc tcatcaatct ctacttgcaa caagagtcag aacccacgat | 1740 |
| ttggctacaa tcgctccaac aaccgcacat gcccttgcag gtcgtttcgc cttagaatgt | 1800 |
| tggggtggtg ccacattcga tgttgcaatg agattttttgc atgaggatcc atgggaacgt | 1860 |
| ttgagaaaat taagatctct ggtgcctaat attccattcc aaatgttatt gcgtggtgcc | 1920 |
| aatggtgtgg cttattcttc attgcctgac aatgctattg accatttcgt caagcaagcc | 1980 |
| aaggataatg gtgttgatat atttagagtc tttgatgcct taaatgactt ggaacaattg | 2040 |
| aaggtcggtg tagatgctgt gaagaaggca ggtggtgttg tagaagccac tgtttgtttc | 2100 |
| tctggggata tgcttcagcc aggcaagaaa tacaatttgg attactactt ggaaattgct | 2160 |
| gaaaaaattg tccaaatggg cactcatatc ctgggtatca agatatggc aggtaccatg | 2220 |
| aagccagcag ctgccaaaact actgattgga tctttgaggg ctaagtaccc tgatctccca | 2280 |
| atacatgttc acactcacga ttctgcaggt actgctgttg catcaatgac tgcgtgtgct | 2340 |
| ctggcgggcg ccgatgtcgt tgatgttgcc atcaactcaa tgtctggttt aacttcacaa | 2400 |
| ccatcaatca atgctctgtt ggcttcatta gaaggtaata ttgacactgg tattaacgtt | 2460 |
| gagcatgtcc gtgaactaga tgcatattgg gcagagatga gattgttata ctcttgtttc | 2520 |
| gaggctgact tgaagggccc agatccagaa gtttatcaac atgaaatccc aggtggtcaa | 2580 |
| ttgacaaact tgttgtttca gcccaacaa ttgggtcttg gagaacaatg ggccgaaaca | 2640 |
| aaaagagctt acagagaagc caattattta ttgggtgata ttgtcaaagt taccccaact | 2700 |
| tcgaaggtcg ttggtgatct ggcacaattt atggtctcca ataaattaac ttccgatgat | 2760 |
| gtgagacgcc tggctaattc ttttggatttc cctgactctg ttatggattt cttcgaaggc | 2820 |
| ttaatcggcc aaccatatgg tgggttccca gaaccattta gatcagacgt tttaaggaac | 2880 |
| aagagaagaa agttgacttg tcgtccaggc ctggaactag agccatttga tctcgaaaaa | 2940 |
| attagagaag acttgcagaa tagatttggt gatgttgatg agtgcgacgt tgcttcttat | 3000 |
| aacatgtacc caagagttta tgaagacttc caaaagatga gagaaacgta tggtgattta | 3060 |
| tctgtattgc caacaagaag ctttttttgtct ccactagaga ctgacgaaga aattgaagtt | 3120 |
| gtaatcgaac aaggtaaaac gctaattatc aagctacagg ctgtgggtga tttgaacaaa | 3180 |
| aagaccggtg aaagagaagt ttactttgat ttgaatggtg aaatgagaaa aattcgtgtt | 3240 |
| gctgacagat cacaaaaagt ggaaactgtt actaaatcca aagcagacat gcatgatcca | 3300 |
| ttacacattg gtgcaccaat ggcaggtgtc attgttgaag ttaaagttca taaaggatca | 3360 |
| ctaataaaga agggccaacc tgtagccgta ttaagcgcca tgaaaatgga aatgattata | 3420 |
| tcttctccat ccgatggaca agttaaagaa gtgtttgtct ctgatggtga aaatgtggac | 3480 |
| tcttctgatt tattagttct attagaagac caagttcctg ttgaaactaa ggcatga | 3537 |

<210> SEQ ID NO 79
<211> LENGTH: 3543
<212> TYPE: DNA
<213> ORGANISM: Saccharomyces cerevisiae
<220> FEATURE:
<221> NAME/KEY: source
<222> LOCATION: 1..3543
<223> OTHER INFORMATION: /mol_type="DNA"
      /organism="Saccharomyces cerevisiae"

<400> SEQUENCE: 79

```
atgagcagta gcaagaaatt ggccggtctt agggacaatt tcagtttgct cggcgaaaag      60
aataagatct tggtcgccaa tagaggtgaa attccgatta gaattttag atctgctcat      120
gagctgtcta tgagaaccat cgccatatac tcccatgagg accgtctttc aatgcacagg     180
ttgaaggcgg acgaagcgta tgttatcggg gaggagggcc agtatacacc tgtgggtgct     240
tacttggcaa tggacgagat catcgaaatt gcaagaagc ataaggtgga tttcatccat      300
ccaggttatg ggttcttgtc tgaaaattcg gaatttgccg acaaagtagt gaaggccggt     360
atcacttgga tcggccctcc agctgaagtt attgactctg tgggtgacaa agtctctgcc    420
agacacttgg cagcaagagc taacgttcct accgttcccg gtactccagg acctatcgaa    480
actgtgcaag aggcacttga cttcgttaat gaatacggct acccggtgat cattaaggcc    540
gcctttggtg gtggtggtag aggtatgaga gtcgttagag aaggtgacga cgtggcagat   600
gcctttcaac gtgctacctc cgaagcccgt actgccttcg gtaatggtac ctgctttgtg   660
gaaagattct tggacaagcc aaagcatatt gaagttcaat tgttggctga taaccacgga   720
aacgtggttc atcttttcga aagagactgt tctgtgcaaa gaagacacca aaaagttgtc   780
gaagtcgctc cagcaaagac tttgccccgt gaagttcgtg acgctatttt gacagatgct   840
gttaaattag ctaaggtatg tggttacaga aacgcaggta ccgccgaatt cttggttgac   900
aaccaaaaca gacactattt cattgaaatt aatccaagaa ttcaagtgga gcataccatc    960
actgaagaaa tcaccggtat tgacattgtt tctgcccaaa tccagattgc cgcaggtgcc   1020
actttgactc aactaggtct attacaggat aaaatcacca cccgtgggtt ttccatccaa   1080
tgtcgtatta ccactgaaga tccctctaag aatttccaac cggataccgg tcgcctggag   1140
gtctatcgtt ctgccggtgg taatggtgtg agattggacg tggtaacgc ttatgcaggt    1200
gctactatct cgcctcacta cgactcaatg ctggtcaaat gttcatgctc tggttctact   1260
tatgaaatcg tccgtaggaa gatgattcgt gccctgatcg aattcagaat cagaggtgtt   1320
aagaccaaca ttcccttcct attgactctt ttgaccaatc cagttttat tgagggtaca    1380
tactggacga cttttattga cgacaccca caactgttcc aaatggtatc gtcacaaaac   1440
agagcgcaaa aactgttaca ctatttggca gacttggcag ttaacggttc ttctattaag   1500
ggtcaaattg gcttgccaaa actaaaatca aatccaagtg tccccatttt gcacgatgct   1560
cagggcaatg tcatcaacgt tacaaagtct gcaccaccat ccggatggag acaagtgcta   1620
ctggaaaagg gaccatctga atttgccaag caagtcagac agttcaatgg tactctactg   1680
atggacacca cctggagaga cgctcatcaa tctctacttg caacaagagt cagaacccac   1740
gatttggcta caatcgctcc aacaaccgca catgcccttg caggtgcttt cgctttagaa   1800
tgttggggtg gtgctacatt cgacgttgca atgagattct tgcatgagga tccatgggaa   1860
cgtctgagaa aattaagatc tctggtgcct aatattccat tccaaatgtt attacgtggt   1920
gccaacggtg tggcttactc ttcattacct gacaatgcta ttgaccattt tgtcaagcaa   1980
gccaaggata atggtgttga tatatttaga gttttttgatg ccttgaatga tttagaacaa   2040
ttaaaagttg gtgtgaatgc tgtcaagaag gccggtggtg ttgtcgaagc tactgtttgt   2100
tactctggtg acatgcttca gccaggtaag aaatacaact tagactacta cctagaagtt   2160
gttgaaaaaa tagttcaaat gggtacacat atcttgggta ttaaggatat ggcaggtact   2220
atgaaaccgg ccgctgccaa attattaatt ggctccctaa gaaccagata tccggattta   2280
ccaattcatg ttcacagtca tgactccgca ggtactgctg ttgcgtctat gactgcatgt   2340
```

```
gccctagcag gtgctgatgt tgtcgatgta gctatcaatt caatgtcggg cttaacttcc    2400
caaccatcaa ttaatgcact gttggcttca ttagaaggta acattgatac tgggattaac    2460
gttgagcatg ttcgtgaatt agatgcatac tgggccgaaa tgagactgtt gtattcttgt    2520
ttcgaggccg acttgaaggg accagatcca gaagtttacc aacatgaaat cccaggtggt    2580
caattgacta acttgttatt ccaagctcaa caactgggtc ttggtgaaca atgggctgaa    2640
actaaaagag cttacagaga agccaattac ctactgggag atattgttaa agttacccca    2700
acttctaagg ttgtcggtga tttagctcaa ttcatggttt ctaacaaact gacttccgac    2760
gatattagac gtttagctaa ttctttggac tttcctgact ctgttatgga cttttttgaa    2820
ggtttaattg gtcaaccata cggtgggttc ccagaaccat aagatctga tgtattgaga    2880 aacaagagaa gaaagttgac gtgccgtcca ggtttagaat tagaaccatt tgatctcgaa    2940
aaaattagag aagacttgca gaacagattc ggtgatattg atgaatgcga tgttgcttct    3000
tacaatatgt atccaagggt ctatgaagat ttccaaaaga tcagagaaac atacggtgat    3060
ttatcagttc taccaaccaa aaatttccta gcaccagcag aacctgatga agaaatcgaa    3120
gtcaccatcg aacaaggtaa gactttgatt atcaaattgc aagctgttgg tgacttaaat    3180
aagaaaactg ggcaaagaga agtgtatttt gaattgaacg gtgaattaag aaagatcaga    3240
gttgcagaca agtcacaaaa catacaatct gttgctaaac caaaggctga tgtccacgat    3300
actcaccaaa tcggtgcacc aatggctggt gttatcatag aagttaaagt acataaaggg    3360
tctttggtga aaaagggcga atcgattgct gttttgagtg ccatgaaaat ggaaatggtt    3420
gtctcttcac cagcagatgg tcaagttaaa gacgttttca ttaaggatgg tgaaagtgtt    3480
gacgcatcag atttgttggt tgtcctagaa gaagaaaccc taccccatc ccaaaaaaag    3540 taa                                                                  3543
```

<210> SEQ ID NO 80
<211> LENGTH: 1257
<212> TYPE: DNA
<213> ORGANISM: Saccharomyces cerevisiae
<220> FEATURE:
<221> NAME/KEY: source
<222> LOCATION: 1..1257
<223> OTHER INFORMATION: /mol_type="DNA"
      /organism="Saccharomyces cerevisiae"

<400> SEQUENCE: 80

```
atgtctgcca ctctgttcaa taacatcgaa ttgctgcccc ctgatgccct ttttggtatt      60
aagcaaaggt acgggcaaga tcaacgtgct accaaggtcg acttgggtat cggggcctac     120
agagacgaca acggtaaacc atgggtcttg ccaagtgtta aagccgccga aaagctaatt     180
cataacgaca gctcctacaa ccatgaatac ctcggtatta ccggtctgcc aagtttgaca     240
tctaacgccg ccaagatcat cttcggtacg caatccgatg cctttcagga agacagagta     300
atctcagtac aatcactgtc tggtacgggt gctcttcata tatctgcgaa gttttttca     360 aaattcttcc cagataaact ggtctatttg tctaagccta cttgggccaa ccacatggcc     420 attttttgaga atcaaggctt gaaaacggcg acttaccctt actgggccaa cgaaactaag     480
tctttggacc taaacggctt tctaaatgct attcaaaaag ctccagaggg ctccattttc     540
gttctgcact cttgcgccca taacccaact ggtctggacc tactagtgaa caatggggtt     600
caaatcgttg atgctatcgc ctcaagaaac cacatcgcct atttgacac cgcctaccaa     660 gggtttgcca ctggagattt ggacaaggat gcctatgctg tgcgtctagg tgtggagaag     720
```

```
ctttcaacgg tctctcccgt ctttgtctgt cagtcctttg ccaagaacgc cggtatgtac    780
ggtgagcgtg taggttgttt ccatctagca cttacaaaac aagctcaaaa caaaactata    840
aagcctgctg ttacatctca attggccaaa atcattcgta gtgaagtgtc caacccaccc    900
gcctacggcg ctaagattgt cgctaaactg ttggaaacgc cagaattaac ggaacagtgg    960
cacaaggata tggttaccat gtcctccaga attacgaaaa tgaggcacgc attaagagac   1020
catttagtca agttgggcac tcctggcaac tgggatcata tagtaaatca atgcgggatg   1080
ttctccttta caggattgac tcctcaaatg gttaaacgac ttgaagaaac ccacgcagtt   1140
tacttggttg cctcaggtag agcttctatt gctggattga atcaaggaaa cgtggaatac   1200
gtggctaaag ccattgatga agtggtgcgc ttctatacta ttgaagctaa attgtaa     1257
```

<210> SEQ ID NO 81
<211> LENGTH: 6607
<212> TYPE: DNA
<213> ORGANISM: Artificial Sequence
<220> FEATURE:
<221> NAME/KEY: source
<222> LOCATION: 1..6607
<223> OTHER INFORMATION: /mol_type="DNA"
    /note="plasmid"
    /organism="Artificial Sequence"

<400> SEQUENCE: 81

```
tcgcgcgttt cggtgatgac ggtgaaaacc tctgacacat gcagctcccg gagacggtca     60
cagcttgtct gtaagcggat gccgggagca gacaagcccg tcaggcgcg tcagcgggtg    120 ttggcgggtg tcggggctgg cttaactatg cggcatcaga gcagattgta ctgagagtgc    180
accataccac agcttttcaa ttcaattcat cattttttt ttattctttt ttttgatttc    240
ggtttctttg aaattttttt gattcggtaa tctccgaaca aaggaagaa cgaaggaagg    300 agcacagact tagattggta tatatacgca tatgtagtgt tgaagaaaca tgaaattgcc    360
cagtattctt aacccaactg cacagaacaa aaacctgcag gaaacgaaga taaatcatgt    420
cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaaacacatg    600
tggatatctt gactgatttt tccatggagg gcacagttaa gccgctaaag gcattatccg    660
ccaagtacaa ttttttactc ttcgaagaca gaaaatttgc tgacattggt aatacagtca    720
aattgcagta ctctgcgggt gtatacagaa tagcagaatg gcagacatt acgaatgcac    780 acggtgtggt gggcccaggt attgttagcg gtttgaagca ggcggcagaa gaagtaacaa    840
aggaacctag aggccttttg atgttagcag aattgtcatg caagggctcc ctatctactg    900
gagaatatac taagggtact gttgacattg cgaagagcga caaagatttt gttatcggct    960
ttattgctca agagacatg gtggaagag atgaaggtta cgattggttg attatgacac    1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagaggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga ataccgcac    1320 agatgcgtaa ggagaaaata ccgcatcagg aaattgtaaa cgttaatatt ttgttaaaat   1380
```

-continued

```
tcgcgttaaa ttttgttaa atcagctcat ttttaacca ataggccgaa atcggcaaaa    1440
tcccttataa atcaaaagaa tagaccgaga tagggttgag tgttgttcca gtttggaaca    1500
agagtccact attaaagaac gtggactcca acgtcaaagg gcgaaaaacc gtctatcagg    1560
gcgatggccc actacgtgaa ccatcaccct aatcaagttt tttggggtcg aggtgccgta    1620
aagcactaaa tcggaaccct aaagggagcc cccgatttag agcttgacgg ggaaagccgg    1680
cgaacgtggc gagaaaggaa gggaagaaag cgaaaggagc gggcgctagg gcgctggcaa    1740
gtgtagcggt cacgctgcgc gtaaccacca cacccgccgc gcttaatgcg ccgctacagg    1800
gcgcgtccat tcgccattca ggctgcgcaa ctgttgggaa gggcgatcgg tgcgggcctc    1860
ttcgctatta cgccagctga attggagcga cctcatgcta tacctgagaa agcaacctga    1920
cctacaggaa agagttactc aagaataaga attttcgttt taaaacctaa gagtcacttt    1980
aaaatttgta tacacttatt tttttataa cttatttaat aataaaaatc ataaatcata     2040
agaaattcgc ttatttagaa gtgtcaacaa cgtatctacc aacgatttga ccctttttcca   2100 tctttttcgta aatttctggc aaggtagaca agccgacaac cttgattgga gacttgacca   2160
aacctctggc gaagaattgt taattaagag ctcagatctt atcgtcgtca tccttgtaat    2220
ccatcgatac tagtgcggcc gcccttttagt gagggttgaa ttcgaatttt caaaaattct    2280
tacttttttt ttggatggac gcaaagaagt ttaataatca tattacatgg cattaccacc    2340
atatacatat ccatatacat atccatatct aatcttactt atatgttgtg gaaatgtaaa    2400 gagcccccatt atcttagcct aaaaaaacct tctctttgga actttcagta atacgcttaa    2460
ctgctcattg ctatattgaa gtacggatta gaagccgccg agcgggtgac agccctccga    2520
aggaagactc tcctccgtgc gtcctcgtct tcaccggtcg cgttcctgaa acgcagatgt    2580
gcctcgcgcc gcactgctcc gaacaataaa gattctacaa tactagcttt tatggttatg    2640
aagaggaaaa attggcagta acctggcccc acaaaccttc aaatgaacga atcaaattaa    2700
caaccatagg atgataatgc gattagtttt ttagccttat ttctggggta attaatcagc    2760
gaagcgatga ttttgatct attaacagat atataaatgc aaaaactgca taaccacttt     2820
aactaatact ttcaacattt tcggtttgta ttacttctta ttcaaatgta ataaaagtat    2880
caacaaaaaa ttgttaatat acctctatac tttaacgtca aggagaaaaa accccggatc    2940
catgcatcac catcaccacc atagtgcagg tggtaccgta gcatcgtacg tcgacatcgc    3000
acggctagct aagatccgct ctaaccgaaa aggaaggagt tagacaacct gaagtctagg    3060 tccctatttta tttttttata gttatgttag tattaagaac gttatttata tttcaaattt    3120 ttctttttt tctgtacaga cgcgtgtacg catgtaacat tatactgaaa accttgcttg     3180
agaaggtttt gggacgctcg aagatccagc tgcattaatg aatcggccaa cgcgcgggga    3240
gaggcggttt gcgtattggg cgctcttccg cttcctcgct cactgactcg ctgcgctcgg    3300
tcgttcggct gcggcgagcg gtatcagctc actcaaaggc ggtaatacgg ttatccacag    3360
aatcagggga taacgcagga aagaacatgt gagcaaaagg ccagcaaaag gccaggaacc    3420
gtaaaaaggc cgcgttgctg gcgtttttcc ataggctccg ccccccctgac gagcatcaca    3480 aaaatcgacg ctcaagtcag aggtggcgaa acccgacagg actataaaga taccaggcgt    3540
ttccccctgg aagctccctc gtgcgctctc ctgttccgac cctgccgctt accggatacc    3600
tgtccgcctt tctcccttcg ggaagcgtgg cgctttctca tagctcacgc tgtaggtatc    3660
tcagttcggt gtaggtcgtt cgctccaagc tgggctgtgt gcacgaaccc cccgttcagc    3720
ccgaccgctg cgccttatcc ggtaactatc gtcttgagtc caacccggta agacacgact    3780
```

| | |
|---|---|
| tatcgccact ggcagcagcc actggtaaca ggattagcag agcgaggtat gtaggcggtg | 3840 |
| ctacagagtt cttgaagtgg tggcctaact acggctacac tagaaggaca gtatttggta | 3900 |
| tctgcgctct gctgaagcca gttaccttcg aaaaagagt tggtagctct tgatccggca | 3960 |
| aacaaaccac cgctggtagc ggtggttttt ttgtttgcaa gcagcagatt acgcgcagaa | 4020 |
| aaaaaggatc tcaagaagat cctttgatct tttctacggg gtctgacgct cagtggaacg | 4080 |
| aaaactcacg ttaagggatt ttggtcatga gattatcaaa aaggatcttc acctagatcc | 4140 |
| ttttaaatta aaaatgaagt tttaaatcaa tctaaagtat atatgagtaa acttggtctg | 4200 |
| acagttacca atgcttaatc agtgaggcac ctatctcagc gatctgtcta tttcgttcat | 4260 |
| ccatagttgc ctgactcccc gtcgtgtaga taactacgat acgggagggc ttaccatctg | 4320 |
| gccccagtgc tgcaatgata ccgcgagacc cacgctcacc ggctccagat ttatcagcaa | 4380 |
| taaaccagcc agccggaagg gccgagcgca gaagtggtcc tgcaacttta tccgcctcca | 4440 |
| tccagtctat taattgttgc cgggaagcta gagtaagtag ttcgccagtt aatagtttgc | 4500 |
| gcaacgttgt tgccattgct acaggcatcg tggtgtcacg ctcgtcgttt ggtatggctt | 4560 |
| cattcagctc cggttcccaa cgatcaaggc gagttacatg atcccccatg ttgtgcaaaa | 4620 |
| aagcggttag ctccttcggt cctccgatcg ttgtcagaag taagttggcc gcagtgttat | 4680 |
| cactcatggt tatggcagca ctgcataatt ctcttactgt catgccatcc gtaagatgct | 4740 |
| tttctgtgac tggtgagtac tcaaccaagt cattctgaga atagtgtatg cggcgaccga | 4800 |
| gttgctcttg cccggcgtca atacgggata ataccgcgcc acatagcaga actttaaaag | 4860 |
| tgctcatcat tggaaaacgt tcttcgggg gaaaactctc aaggatctta ccgctgttga | 4920 |
| gatccagttc gatgtaaccc actcgtgcac ccaactgatc ttcagcatct tttactttca | 4980 |
| ccagcgtttc tgggtgagca aaaacaggaa ggcaaaatgc cgcaaaaaag ggaataaggg | 5040 |
| cgacacggaa atgttgaata ctcatactct ccttttttca atattattga agcatttatc | 5100 |
| agggttattg tctcatgagc ggatacatat ttgaatgtat ttagaaaaat aaacaaatag | 5160 |
| gggttccgcg cacatttccc cgaaaagtgc cacctgaacg aagcatctgt gcttcatttt | 5220 |
| gtagaacaaa aatgcaacgc gagagcgcta atttttcaaa caagaatct gagctgcatt | 5280 |
| tttacagaac agaaatgcaa cgcgaaagcg ctattttacc aacgaagaat ctgtgcttca | 5340 |
| tttttgtaaa acaaaaatgc aacgcgagag cgctaatttt tcaaacaaag aatctgagct | 5400 |
| gcattttac agaacagaaa tgcaacgcga gagcgctatt ttaccaacaa agaatctata | 5460 |
| cttcttttt gttctacaaa aatgcatccc gagagcgcta tttttctaac aaagcatctt | 5520 |
| agattacttt ttttctcctt tgtgcgctct ataatgcagt ctcttgataa cttttgcac | 5580 |
| tgtaggtccg ttaaggttag aagaaggcta ctttggtgtc tattttctct tccataaaaa | 5640 |
| aagcctgact ccacttcccg cgtttactga ttactagcga agctgcgggt gcattttttc | 5700 |
| aagataaagg catccccgat tatattctat accgatgtgg attgcgcata ctttgtgaac | 5760 |
| agaaagtgat agcgttgatg attcttcatt ggtcagaaaa ttatgaacgg tttcttctat | 5820 |
| tttgtctcta tatactacgt ataggaaatg tttacatttt cgtattgttt tcgattcact | 5880 |
| ctatgaatag ttcttactac aattttttg tctaaagagt aatactagag ataaacataa | 5940 |
| aaaatgtaga ggtcgagttt agatgcaagt tcaaggagcg aaaggtggat gggtaggtta | 6000 |
| tatagggata tagcacagag atatatagca aagagatact tttgagcaat gtttgtggaa | 6060 |
| gcggtattcg caatatttta gtagctcgtt acagtccggt gcgtttttgg ttttttgaaa | 6120 |

```
gtgcgtcttc agagcgcttt tggttttcaa aagcgctctg aagttcctat actttctaga    6180
gaataggaac ttcggaatag gaacttcaaa gcgtttccga aaacgagcgc ttccgaaaat    6240
gcaacgcgag ctgcgcacat acagctcact gttcacgtcg cacctatatc tgcgtgttgc    6300
ctgtatatat atatacatga gaagaacggc atagtgcgtg tttatgctta aatgcgtact    6360
tatatgcgtc tatttatgta ggatgaaagg tagtctagta cctcctgtga tattatccca    6420
ttccatgcgg ggtatcgtat gcttccttca gcactaccct ttagctgttc tatatgctgc    6480
cactcctcaa ttggattagt ctcatccttc aatgctatca tttcctttga tattggatca    6540
tactaagaaa ccattattat catgacatta acctataaaa ataggcgtat cacgaggccc    6600
tttcgtc                                                              6607
```

<210> SEQ ID NO 82
<211> LENGTH: 6586
<212> TYPE: DNA
<213> ORGANISM: Artificial Sequence
<220> FEATURE:
<221> NAME/KEY: source
<222> LOCATION: 1..6586
<223> OTHER INFORMATION: /mol_type="DNA"
      /note="plasmid"
      /organism="Artificial Sequence"

<400> SEQUENCE: 82

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accataccac agcttttcaa ttcaattcat catttttttt ttattctttt ttttgatttc     240
ggtttctttg aaattttttt gattcggtaa tctccgaaca aaggaagaa cgaaggaagg     300 agcacagact tagattggta tatatacgca tatgtagtgt tgaagaaaca tgaaattgcc     360
cagtattctt aacccaactg cacagaacaa aaacctgcag gaaacgaaga taaatcatgt     420
cgaaagctac atataaggaa cgtgctgcta ctcatcctag tcctgttgct gccaagctat     480
ttaatatcat gcacgaaaag caaacaaact tgtgtgcttc attggatgtt cgtaccacca     540
aggaattact ggagttagtt gaagcattag gtcccaaaat ttgtttacta aaaacacatg     600
tggatatctt gactgatttt tccatggagg gcacagttaa gccgctaaag gcattatccg     660
ccaagtacaa ttttttactc ttcgaagaca gaaaatttgc tgacattggt aatacagtca     720
aattgcagta ctctgcgggt gtatacgaa tagcagaatg gcagacatt acgaatgcac     780 acggtgtggt gggcccaggt attgttagcg gtttgaagca ggcggcagaa gaagtaacaa     840
aggaacctag aggcctttttg atgttagcag aattgtcatg caagggctcc ctatctactg     900
gagaatatac taagggtact gttgacattg cgaagagcga caaagatttt gttatcggct     960
ttattgctca agagacatg ggtggaagag atgaaggtta cgattggttg attatgacac    1020
ccggtgtggg tttagatgac aagggagacg cattgggtca acagtataga accgtggatg    1080
atgtggtctc tacaggatct gacattatta ttgttggaag aggactattt gcaaagggaa    1140
gggatgctaa ggtagaggt gaacgttaca gaaaagcagg ctggaagca tatttgagaa    1200 gatgcggcca gcaaaactaa aaaactgtat tataagtaaa tgcatgtata ctaaactcac    1260
aaattagagc ttcaatttaa ttatatcagt tattacccta tgcggtgtga aataccgcac    1320
agatgcgtaa ggagaaaata ccgcatcagg aaattgtaaa cgttaatatt ttgttaaaat    1380
tcgcgttaaa tttttgttaa atcagctcat ttttttaacca ataggccgaa atcggcaaaa    1440
```

```
tcccttataa atcaaaagaa tagaccgaga tagggttgag tgttgttcca gtttggaaca    1500
agagtccact attaaagaac gtggactcca acgtcaaagg gcgaaaaacc gtctatcagg    1560
gcgatggccc actacgtgaa ccatcaccct aatcaagttt tttggggtcg aggtgccgta    1620
aagcactaaa tcggaaccct aaagggagcc cccgatttag agcttgacgg ggaaagccgg    1680
cgaacgtggc gagaaaggaa gggaagaaag cgaaaggagc gggcgctagg gcgctggcaa    1740
gtgtagcggt cacgctgcgc gtaaccacca cacccgccgc gcttaatgcg ccgctacagg    1800
gcgcgtccat cgccattca ggctgcgcaa ctgttgggaa gggcgatcgg tgcgggcctc     1860
ttcgctatta cgccagctga attggagcga cctcatgcta tacctgagaa agcaacctga    1920
cctacaggaa agagttactc aagaataaga attttcgttt taaaacctaa gagtcacttt    1980
aaaatttgta tacacttatt ttttttataa cttatttaat aataaaaatc ataaatcata    2040
agaaattcgc ttatttagaa gtgtcaacaa cgtatctacc aacgatttga ccctttttcca   2100 tcttttcgta aatttctggc aaggtagaca agccgacaac cttgattgga gacttgacca   2160
aacctctggc gaagaattgt taattaagag ctcagatctt atcgtcgtca tccttgtaat    2220
ccatcgatac tagtgcggcc gcccttagt gagggttgaa ttcgaatttt caaaaattct     2280
tacttttttt ttggatggac gcaaagaagt ttaataatca tattacatgg cattaccacc    2340
atatacatat ccatatacat atccatatct aatcttactt atatgttgtg gaaatgtaaa    2400
gagccccatt atcttagcct aaaaaaacct tctctttgga actttcagta atacgcttaa    2460
ctgctcattg ctatattgaa gtacggatta gaagccgccg agcgggtgac agccctccga    2520
aggaagactc tcctccgtgc gtcctcgtct tcaccggtcg cgttcctgaa acgcagatgt    2580
gcctcgcgcc gcactgctcc gaacaataaa gattctacaa tactagcttt tatggttatg    2640
aagaggaaaa attggcagta acctggcccc acaaaccttc aaatgaacga atcaaattaa    2700
caaccatagg atgataatgc gattagtttt ttagccttat ttctggggta attaatcagc    2760
gaagcgatga ttttgatct attaacagat atataaatgc aaaaactgca taaccacttt     2820
aactaatact ttcaacattt tcggtttgta ttacttctta ttcaaatgta ataaaagtat    2880
caacaaaaaa ttgttaatat acctctatac tttaacgtca aggagaaaaa accccggatc    2940
catctgtcat ggtaccgtag catcgtacgt cgacatcgcg tggctagcta agatccgctc    3000
taaccgaaaa ggaaggagtt agacaacctg aagtctaggt cccctatttat ttttttatag   3060 ttatgttagt attaagaacg ttatttatat ttcaaatttt tctttttttt ctgtacagac    3120
gcgtgtacgc atgtaacatt atactgaaaa ccttgcttga aaggttttg gacgctcga      3180 agatccagct gcattaatga atcggccaac gcgcggggag aggcggtttg cgtattgggc    3240
gctcttccgc ttcctcgctc actgactcgc tgcgctcggt cgttcggctg cggcgagcgg    3300
tatcagctca ctcaaaggcg gtaatacggt tatccacaga atcaggggat aacgcaggaa    3360
agaacatgtg agcaaaaggc cagcaaaagg ccaggaaccg taaaaaggcc gcgttgctgg    3420
cgttttccca taggctccgc cccctgacg agcatcacaa aaatcgacgc tcaagtcaga    3480
ggtggcgaaa cccgacagga ctataaagat accaggcgtt tccccctgga agctccctcg    3540
tgcgctctcc tgttccgacc ctgccgctta ccggatacct gtccgccttt ctcccttcgg    3600
gaagcgtggc gctttctcat agctcacgct gtaggtatct cagttcggtg taggtcgttc    3660
gctccaagct gggctgtgtg cacgaacccc ccgttcagcc cgaccgctgc gccttatccg    3720
gtaactatcg tcttgagtcc aacccggtaa gacacgactt atcgccactg gcagcagcca    3780
```

| | |
|---|---|
| ctggtaacag gattagcaga gcgaggtatg taggcggtgc tacagagttc ttgaagtggt | 3840 |
| ggcctaacta cggctacact agaaggacag tatttggtat ctgcgctctg ctgaagccag | 3900 |
| ttaccttcgg aaaaagagtt ggtagctctt gatccggcaa acaaaccacc gctggtagcg | 3960 |
| gtggtttttt tgtttgcaag cagcagatta cgcgcagaaa aaaaggatct caagaagatc | 4020 |
| ctttgatctt ttctacgggg tctgacgctc agtggaacga aaactcacgt taagggattt | 4080 |
| tggtcatgag attatcaaaa aggatcttca cctagatcct tttaaattaa aaatgaagtt | 4140 |
| ttaaatcaat ctaaagtata tatgagtaaa cttggtctga cagttaccaa tgcttaatca | 4200 |
| gtgaggcacc tatctcagcg atctgtctat ttcgttcatc catagttgcc tgactccccg | 4260 |
| tcgtgtagat aactacgata cgggagggct taccatctgg ccccagtgct gcaatgatac | 4320 |
| cgcgagaccc acgctcaccg gctccagatt tatcagcaat aaaccagcca gccgaaggg | 4380 |
| ccgagcgcag aagtggtcct gcaactttat ccgcctccat ccagtctatt aattgttgcc | 4440 |
| gggaagctag agtaagtagt tcgccagtta atagtttgcg caacgttgtt gccattgcta | 4500 |
| caggcatcgt ggtgtcacgc tcgtcgtttg gtatggcttc attcagctcc ggttcccaac | 4560 |
| gatcaaggcg agtacatga tcccccatgt tgtgcaaaaa agcggttagc tccttcggtc | 4620 |
| ctccgatcgt tgtcagaagt aagttggccg cagtgttatc actcatggtt atggcagcac | 4680 |
| tgcataattc tcttactgtc atgccatccg taagatgctt ttctgtgact ggtgagtact | 4740 |
| caaccaagtc attctgagaa tagtgtatgc ggcgaccgag ttgctcttgc ccggcgtcaa | 4800 |
| tacgggataa taccgcgcca catagcagaa ctttaaaagt gctcatcatt ggaaaacgtt | 4860 |
| cttcggggcg aaaactctca aggatcttac cgctgttgag atccagttcg atgtaaccca | 4920 |
| ctcgtgcacc caactgatct tcagcatctt ttactttcac cagcgtttct gggtgagcaa | 4980 |
| aaacaggaag gcaaaatgcc gcaaaaaagg gaataagggc gacacggaaa tgttgaatac | 5040 |
| tcatactctt cctttttcaa tattattgaa gcatttatca gggttattgt ctcatgagcg | 5100 |
| gatacatatt tgaatgtatt tagaaaaata acaaataggg gttccgcgc acatttcccc | 5160 |
| gaaaagtgcc acctgaacga agcatctgtg cttcattttg tagaacaaaa atgcaacgcg | 5220 |
| agagcgctaa ttttttcaaac aaagaatctg agctgcattt ttacagaaca gaatgcaac | 5280 |
| gcgaaagcgc tattttacca acgaagaatc tgtgcttcat ttttgtaaaa caaaaatgca | 5340 |
| acgcgagagc gctaattttt caaacaaaga atctgagctg catttttaca gaacagaaat | 5400 |
| gcaacgcgag agcgctattt taccaacaaa gaatctatac ttcttttttg ttctacaaaa | 5460 |
| atgcatcccg agagcgctat ttttctaaca aagcatctta gattactttt ttctcctttt | 5520 |
| gtgcgctcta taatgcagtc tcttgataac ttttgcact gtaggtccgt taaggttaga | 5580 |
| agaaggctac tttggtgtct attttctctt ccataaaaaa agcctgactc cacttcccgc | 5640 |
| gtttactgat tactagcgaa gctgcgggtg catttttca agataaaggc atccccgatt | 5700 |
| atattctata ccgatgtgga ttgcgcatac tttgtgaaca gaaagtgata gcgttgatga | 5760 |
| ttcttcattg gtcagaaaat tatgaacggt ttcttctatt ttgtctctat atactacgta | 5820 |
| taggaaatgt ttacattttc gtattgtttt cgattcactc tatgaatagt tcttactaca | 5880 |
| attttttgt ctaaagagta atactagaga taaacataaa aaatgtagag gtcgagttta | 5940 |
| gatgcaagtt caaggagcga aaggtggatg ggtaggttat atagggatat agcacagaga | 6000 |
| tatatagcaa agagatactt ttgagcaatg tttgtggaag cggtattcgc aatattttag | 6060 |
| tagctcgtta cagtccggtg cgttttggt ttttgaaag tgcgtcttca gagcgctttt | 6120 |
| ggttttcaaa agcgctctga agttcctata ctttctagag aataggaact tcggaatagg | 6180 |

```
aacttcaaag cgtttccgaa aacgagcgct tccgaaaatg caacgcgagc tgcgcacata     6240
cagctcactg ttcacgtcgc acctatatct gcgtgttgcc tgtatatata tatacatgag     6300
aagaacggca tagtgcgtgt ttatgcttaa atgcgtactt atatgcgtct atttatgtag     6360
gatgaaaggt agtctagtac ctcctgtgat attatcccat tccatgcggg gtatcgtatg     6420
cttccttcag cactacccct tagctgttct atatgctgcc actcctcaat tggattagtc     6480
tcatccttca atgctatcat ttcctttgat attggatcat actaagaaac cattattatc     6540
atgacattaa cctataaaaa taggcgtatc acgaggccct ttcgtc                    6586
```

<210> SEQ ID NO 83
<211> LENGTH: 5918
<212> TYPE: DNA
<213> ORGANISM: Artificial Sequence
<220> FEATURE:
<221> NAME/KEY: source
<222> LOCATION: 1..5918
<223> OTHER INFORMATION: /mol_type="DNA"
      /note="plasmid"
      /organism="Artificial Sequence"

<400> SEQUENCE: 83

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcgggctgg cttaactatg cggcatcaga gcagattgta ctgagagtgc       180
accataaatt cccgttttaa gagcttggtg agcgctagga gtcactgcca ggtatcgttt      240
gaacacggca ttagtcaggg aagtcataac acagtccttt cccgcaattt tcttttttcta    300 ttactcttgg cctcctctag tacactctat attttttat gcctcggtaa tgattttcat       360
tttttttttt cccctagcgg atgactcttt tttttcttta gcgattggca ttatcacata     420
atgaattata cattatataa agtaatgtga tttcttcgaa gaatatacta aaaaatgagc      480
aggcaagata acgaaggca aagatgacag agcagaaagc cctagtaaag cgtattacaa       540
atgaaaccaa gattcagatt gcgatctctt taaagggtgg tccctagcg atagagcact       600 cgatcttccc agaaaagag gcagaagcag tagcagaaca ggccacacaa tcgcaagtga      660
ttaacgtcca cacaggtata gggtttctgg accatatgat acatgctctg ccaagcatt       720 ccggctggtc gctaatcgtt gagtgcattg gtgacttaca catagacgac catcacacca     780
ctgaagactg cgggattgct ctcggtcaag cttttaaaga ggccctactg gcgcgtggag      840
taaaaaggtt tggatcagga tttgcgcctt tggatgaggc actttccaga gcggtggtag     900
atctttcgaa caggccgtac gcagttgtcg aacttggttt gcaaagggag aaagtaggag     960
atctctcttg cgagatgatc ccgcattttc ttgaaagctt gcagaggct agcagaatta     1020 ccctccacgt tgattgtctg cgaggcaaga atgatcatca ccgtagtgag agtgcgttca   1080
aggctcttgc ggttgccata agagaagcca cctcgcccaa tggtaccaac gatgttccct    1140
ccaccaaagg tgttcttatg tagtgacacc gattatttaa agctgcagca tacgatatat    1200
atacatgtgt atatatgtat acctatgaat gtcagtaagt atgtatacga acagtatgat    1260
actgaagatg acaaggtaat gcatcattct atacgtgtca ttctgaacga ggcgcgcttt    1320 cctttttttct ttttgctttt tcttttttttt tctccttgaac tcgacggatc tatgcggtgt   1380
gaaataccgc acagatgcgt aaggagaaaa taccgcatca ggaaattgta acgttaata     1440 ttttgttaaa attcgcgtta aattttttgtt aaatcagctc attttttaac caataggccg   1500
```

```
aaatcggcaa aatcccttat aaatcaaaag aatagaccga gatagggttg agtgttgttc    1560
cagtttggaa caagagtcca ctattaaaga acgtggactc caacgtcaaa gggcgaaaaa    1620
ccgtctatca gggcgatggc ccactacgtg aaccatcacc ctaatcaagt tttttggggt    1680
cgaggtgccg taaagcacta aatcggaacc ctaaagggag ccccgattt agagcttgac     1740 ggggaaagcc ggcgaacgtg gcgagaaagg aagggaagaa agcgaaagga gcgggcgcta    1800
gggcgctggc aagtgtagcg gtcacgctgc gcgtaaccac cacacccgcc gcgcttaatg    1860
cgccgctaca gggcgcgtcg cgccattcgc cattcaggct gcgcaactgt tgggaagggc    1920
gatcggtgcg ggcctcttcg ctattacgcc agctgaattg gagcgacctc atgctatacc    1980
tgagaaagca acctgaccta caggaaagag ttactcaaga ataagaattt tcgttttaaa    2040
acctaagagt cactttaaaa tttgtataca cttattttt ttataactta tttaataata     2100
aaaatcataa atcataagaa attcgcttat ttagaagtgt caacaacgta tctaccaacg    2160 atttgacccct tttccatctt ttcgtaaatt tctggcaagg tagacaagcc gacaaccttg   2220
attggagact tgaccaaacc tctggcgaag aattgttaat taagagctcg aatgcgtgcg    2280
atcgcgtgca ttcctcgagt aagcttggta ccgcggctag ctaagatccg ctctaaccga    2340
aaaggaagga gttagacaac ctgaagtcta ggtccctatt tatttttta tagttatgtt     2400 agtattaaga acgttattta tatttcaaat ttttctttt tttctgtaca gacgcgtgta     2460
cgcatgtaac attatactga aaaccttgct tgagaaggtt ttgggacgct cgaagatcca    2520
gctgcattaa tgaatcggcc aacgcgcggg gagaggcggt ttgcgtattg ggcgctcttc    2580
cgcttcctcg ctcactgact cgctgcgctc ggtcgttcgg ctgcggcgag cggtatcagc    2640
tcactcaaag gcggtaatac ggttatccac agaatcaggg gataacgcag gaaagaacat    2700
gtgagcaaaa ggccagcaaa aggccaggaa ccgtaaaaag gccgcgttgc tggcgttttt    2760
ccataggctc cgccccctg acgagcatca caaaaatcga cgctcaagtc agaggtggcg     2820
aaacccgaca ggactataaa gataccaggc gtttccccct ggaagctccc tcgtgcgctc    2880
tcctgttccg accctgccgc ttaccggata cctgtccgcc tttctccctt cgggaagcgt    2940
ggcgctttct catagctcac gctgtaggta tctcagttcg gtgtaggtcg ttcgctccaa    3000
gctgggctgt gtgcacgaac cccccgttca gcccgaccgc tgcgccttat ccggtaacta    3060
tcgtcttgag tccaacccgg taagacacga cttatcgcca ctggcagcag ccactggtaa    3120
caggattagc agagcgaggt atgtaggcgg tgctacagag ttcttgaagt ggtggcctaa    3180
ctacggctac actagaagga cagtatttgg tatctgcgct ctgctgaagc cagttacctt    3240
cggaaaaaga gttggtagct cttgatccgg caaacaaacc accgctggta gcggtggttt    3300
ttttgtttgc aagcagcaga ttacgcgcag aaaaaaagga tctcaagaag atcctttgat    3360
cttttctacg gggtctgacg ctcagtggaa cgaaaactca cgttaaggga ttttggtcat    3420
gagattatca aaaaggatct tcacctagat ccttttaaat taaaaatgaa gttttaaatc    3480
aatctaaagt atatatgagt aaacttggtc tgacagttac caatgcttaa tcagtgaggc    3540
acctatctca gcgatctgtc tatttcgttc atccatagtt gcctgactcc ccgtcgtgta    3600
gataactacg atacgggagg gcttaccatc tggccccagt gctgcaatga taccgcgaga    3660
cccacgctca ccggctccag atttatcagc aataaaccag ccagccggaa gggccgagcg    3720
cagaagtggt cctgcaactt tatccgcctc catccagtct attaattgtt gccgggaagc    3780
tagagtaagt agttcgccag ttaatagttt gcgcaacgtt gttgccattg ctacaggcat    3840
cgtggtgtca cgctcgtcgt ttggtatggc ttcattcagc tccggttccc aacgatcaag    3900
```

```
gcgagttaca tgatcccca tgttgtgcaa aaaagcggtt agctccttcg gtcctccgat    3960
cgttgtcaga agtaagttgg ccgcagtgtt atcactcatg gttatggcag cactgcataa    4020
ttctcttact gtcatgccat ccgtaagatg ctttctgtg actggtgagt actcaaccaa     4080
gtcattctga gaatagtgta tgcggcgacc gagttgctct tgcccggcgt caatacggga    4140
taataccgcg ccacatagca gaactttaaa agtgctcatc attggaaaac gttcttcggg    4200
gcgaaaactc tcaaggatct taccgctgtt gagatccagt tcgatgtaac ccactcgtgc    4260
acccaactga tcttcagcat cttttacttt caccagcgtt tctgggtgag caaaaacagg    4320
aaggcaaaat gccgcaaaaa agggaataag ggcgacacgg aaatgttgaa tactcatact    4380
cttcctttt caatattatt gaagcattta tcagggttat tgtctcatga gcggatacat     4440
atttgaatgt atttagaaaa ataaacaaat aggggttccg cgcacatttc cccgaaaagt    4500
gccacctgaa cgaagcatct gtgcttcatt ttgtagaaca aaatgcaac gcgagagcgc     4560
taatttttca aacaaagaat ctgagctgca tttttacaga acagaaatgc aacgcgaaag    4620
cgctatttta ccaacgaaga atctgtgctt catttttgta aacaaaaat gcaacgcgag     4680
agcgctaatt tttcaaacaa agaatctgag ctgcattttt acagaacaga atgcaacgc    4740
gagagcgcta ttttaccaac aaagaatcta tacttctttt ttgttctaca aaaatgcatc    4800
ccgagagcgc tattttttcta acaaagcatc ttagattact tttttctcc tttgtgcgct   4860
ctataatgca gtctcttgat aacttttgc actgtaggtc cgttaaggtt agaagaaggc    4920
tactttggtg tctattttct cttccataaa aaaagcctga ctccacttcc cgcgtttact    4980
gattactagc gaagctgcgg gtgcatttt tcaagataaa ggcatccccg attatattct     5040
ataccgatgt ggattgcgca ctttgtga acagaaagtg atagcgttga tgattcttca     5100
ttggtcagaa aattatgaac ggtttcttct attttgtctc tatatactac gtataggaaa    5160
tgtttacatt ttcgtattgt tttcgattca ctctatgaat agttcttact acaattttt    5220
tgtctaaaga gtaatactag agataaacat aaaaaatgta gaggtcgagt ttagatgcaa    5280
gttcaaggag cgaaaggtgg atgggtaggt tatataggga tatagcacag agatatatag    5340
caaagagata cttttgagca atgttttgtgg aagcggtatt cgcaatattt tagtagctcg    5400
ttacagtccg gtgcgttttt ggttttttga aagtgcgtct tcagagcgct tttggtttc    5460
aaaagcgctc tgaagttcct atactttcta gagaatagga acttcggaat aggaacttca    5520
aagcgtttcc gaaaacgagc gcttccgaaa atgcaacgcg agctgcgcac atacagctca    5580
ctgttcacgt cgcacctata tctgcgtgtt gcctgtatat atatacat gagaagaacg       5640
gcatagtgcg tgtttatgct taaatgcgta cttatatgcg tctatttatg taggatgaaa    5700
ggtagtctag tacctcctgt gatattatcc cattccatgc ggggtatcgt atgcttcctt    5760
cagcactacc ctttagctgt tctatatgct gccactcctc aattggatta gtctcatcct    5820
tcaatgctat catttccttt gatattggat catctaagaa accattatta tcatgacatt    5880
aacctataaa aataggcgta tcacgaggcc ctttcgtc                            5918
```

<210> SEQ ID NO 84
<211> LENGTH: 6970
<212> TYPE: DNA
<213> ORGANISM: Artificial Sequence
<220> FEATURE:
<221> NAME/KEY: source
<222> LOCATION: 1..6970
<223> OTHER INFORMATION: /mol_type="DNA"
      /note="plasmid"

/organism="Artificial Sequence"

<400> SEQUENCE: 84

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accatatcga ctacgtcgta aggccgtttc tgacagagta aaattcttga gggaactttc   240
accattatgg gaaatgcttc aagaaggtat tgacttaaac tccatcaaat ggtcaggtca   300
ttgagtgttt tttatttgtt gtattttttt tttttagag aaaatcctcc aatatcaaat   360
taggaatcgt agtttcatga ttttctgtta cacctaactt tttgtgtggt gccctcctcc   420
ttgtcaatat taatgttaaa gtgcaattct ttttccttat cacgttgagc cattagtatc   480
aatttgctta cctgtattcc tttactatcc tccttttttct ccttcttgat aaatgtatgt   540
agattgcgta tatagtttcg tctaccctat gaacatattc cattttgtaa tttcgtgtcg   600
tttctattat gaatttcatt tataaagttt atgtacaaat atcataaaaa aagagaatct   660
ttttaagcaa ggattttctt aacttcttcg gcgacagcat caccgacttc ggtggtactg   720
ttggaaccac ctaaatcacc agttctgata cctgcatcca aaaccttttt aactgcatct   780
tcaatggcct taccttcttc aggcaagttc aatgacaatt tcaacatcat tgcagcagac   840
aagatagtgg cgatagggtc aaccttattc tttggcaaat ctggagcaga accgtggcat   900
ggttcgtaca aaccaaatgc ggtgttcttg tctggcaaag aggccaagga cgcagatggc   960
aacaaaccca aggaacctgg gataacggag gcttcatcgg agatgatatc accaaacatg  1020
ttgctggtga ttataatacc atttaggtgg gttgggttct taactaggat catggcggca  1080
gaatcaatca attgatgttg aaccttcaat gtagggaatt cgttcttgat ggtttcctcc  1140
acagttttctc tccataatct tgaagaggcc aaaagattag ctttatccaa ggaccaaata  1200
ggcaatggtg gctcatgttg tagggccatg aaagcggcca ttcttgtgat tctttgcact  1260
tctggaacgg tgtattgttc actatcccaa gcgacaccat caccatcgtc ttcctttctc  1320
ttaccaaagt aaatacctcc cactaattct ctgacaacaa cgaagtcagt acctttagca  1380
aattgtggct tgattggaga taagtctaaa agagagtcgg atgcaaagtt acatggtctt  1440
aagttggcgt acaattgaag ttcttttacgg attttttagta aaccttgttc aggtctaaca  1500
ctaccggtac cccatttagg accagccaca gcacctaaca aaacggcatc aaccttcttg  1560
gaggcttcca gcgcctcatc tggaagtggg acacctgtag catcgatagc agcaccacca  1620
attaaatgat tttcgaaatc gaacttgaca ttggaacgaa catcagaaat agctttaaga  1680
accttaatgg cttcggctgt gatttcttga ccaacgtggt cacctggcaa aacgacgatc  1740
ttcttagggg cagacatagg ggcagacatt agaatggtat atccttgaaa tatatatata  1800
tattgctgaa atgtaaaagg taagaaaagt tagaaagtaa gacgattgct aaccacctat  1860
tggaaaaaac aataggtcct taaataatat tgtcaacttc aagtattgtg atgcaagcat  1920
ttagtcatga acgcttctct attctatatg aaaagccggt tccggcctct cacctttcct  1980
ttttctccca attttttcagt tgaaaaaggt atatgcgtca ggcgacctct gaaattaaca  2040
aaaaatttcc agtcatcgaa tttgattctg tgcgatagcg cccctgtgtg ttctcgttat  2100
gttgaggaaa aaaataatgg ttgctaagag attcgaactc ttgcatctta cgatacctga  2160
gtattcccac agtaactgc ggtcaagata tttcttgaat caggcgcctt agaccgctcg  2220
gccaaacaac caattacttg ttgagaaata gagtataatt atcctataaa tataacgttt  2280
```

```
ttgaacacac atgaacaagg aagtacagga caattgattt tgaagagaat gtggattttg    2340
atgtaattgt tgggattcca tttttaataa ggcaataata ttaggtatgt ggatatacta    2400
gaagttctcc tcgaccgtcg atatgcggtg tgaaataccg cacagatgcg taaggagaaa    2460
ataccgcatc aggaaattgt aaacgttaat attttgttaa aattcgcgtt aaattttgt     2520 taaatcagct cattttttaa ccaataggcc gaaatcggca aaatccctta taaatcaaaa    2580
gaatagaccg ataggggtt gagtgttgtt ccagtttgga acaagagtcc actattaaag     2640
aacgtggact ccaacgtcaa agggcgaaaa accgtctatc agggcgatgg cccactacgt    2700
gaaccatcac cctaatcaag tttttggggg tcgaggtgcc gtaaagcact aaatcggaac    2760
cctaaaggga gcccccgatt tagagcttga cggggaaagc cggcgaacgt ggcgagaaag    2820
gaagggaaga aagcgaaagg agcgggcgct agggcgctgg caagtgtagc ggtcacgctg    2880
cgcgtaacca ccacacccgc cgcgcttaat gcgccgctac agggcgcgtc gcgccattcg    2940
ccattcaggc tgcgcaactg ttgggaaggg cgatcggtgc gggcctcttc gctattacgc    3000
cagctgaatt ggagcgacct catgctatac ctgagaaagc aacctgacct acaggaaaga    3060
gttactcaag aataagaatt ttcgttttaa aacctaagag tcactttaaa atttgtatac    3120 acttatttt tttataactt atttaataat aaaaatcata aatcataaga aattcgctta     3180
tttagaagtg tcaacaacgt atctaccaac gatttgaccc ttttccatct tttcgtaaat    3240
ttctggcaag gtagacaagc cgacaacctt gattggagac ttgaccaaac ctctggcgaa    3300
gaattgttaa ttaagagctc gaatgcgtgc gatcgcgtgc attcctcgag taagcttggt    3360
accgcggcta gctaagatcc gctctaaccg aaaaggaagg agttagacaa cctgaagtct    3420
aggtccctat ttattttttt atagttatgt tagtattaag aacgttattt atatttcaaa    3480
tttttctttt ttttctgtac agacgcgtgt acgcatgtaa cattatactg aaaaccttgc    3540
ttgagaaggt tttgggacgc tcgaagatcc agctgcatta atgaatcggc caacgcgcgg    3600
ggagaggcgg tttgcgtatt gggcgctctt ccgcttcctc gctcactgac tcgctgcgct    3660
cggtcgttcg gctgcggcga gcggtatcag ctcactcaaa ggcggtaata cggttatcca    3720
cagaatcagg ggataacgca ggaaagaaca tgtgagcaaa aggccagcaa aaggccagga    3780
accgtaaaaa ggccgcgttg ctggcgtttt tccataggct ccgcccccct gacgagcatc    3840
acaaaaatcg acgctcaagt cagaggtggc gaaacccgac aggactataa agataccagg    3900
cgtttccccc tggaagctcc ctcgtgcgct ctcctgttcc gaccctgccg cttaccggat    3960
acctgtccgc ctttctccct tcgggaagcg tggcgctttc tcatagctca cgctgtaggt    4020
atctcagttc ggtgtaggtc gttcgctcca agctgggctg tgtgcacgaa ccccccgttc    4080
agcccgaccg ctgcgcctta tccggtaact atcgtcttga gtccaacccg gtaagacacg    4140
acttatcgcc actggcagca gccactggta acaggattag cagagcgagg tatgtaggcg    4200
gtgctacaga gttcttgaag tggtggccta actacggcta cactagaagg acagtatttg    4260
gtatctgcgc tctgctgaag ccagttacct tcggaaaaag agttggtagc tcttgatccg    4320
gcaaacaaac caccgctggt agcggtggtt tttttgtttg caagcagcag attacgcgca    4380
gaaaaaaagg atctcaagaa gatcctttga tcttttctac ggggtctgac gctcagtgga    4440
acgaaaactc acgttaaggg attttggtca tgagattatc aaaaaggatc ttcacctaga    4500
tccttttaaa ttaaaaatga agttttaaat caatctaaag tatatatgag taaacttggt    4560
ctgacagtta ccaatgctta atcagtgagg cacctatctc agcgatctgt ctatttcgtt    4620
```

```
catccatagt tgcctgactc cccgtcgtgt agataactac gatacgggag ggcttaccat    4680
ctggccccag tgctgcaatg ataccgcgag acccacgctc accggctcca gatttatcag    4740
caataaacca gccagccgga agggccgagc gcagaagtgg tcctgcaact ttatccgcct    4800
ccatccagtc tattaattgt tgccgggaag ctagagtaag tagttcgcca gttaatagtt    4860
tgcgcaacgt tgttgccatt gctacaggca tcgtggtgtc acgctcgtcg tttggtatgg    4920
cttcattcag ctccggttcc caacgatcaa ggcgagttac atgatccccc atgttgtgca    4980
aaaaagcggt tagctccttc ggtcctccga tcgttgtcag aagtaagttg gccgcagtgt    5040
tatcactcat ggttatggca gcactgcata attctcttac tgtcatgcca tccgtaagat    5100
gcttttctgt gactggtgag tactcaacca agtcattctg agaatagtgt atgcggcgac    5160
cgagttgctc ttgcccggcg tcaatacggg ataataccgc gccacatagc agaactttaa    5220
aagtgctcat cattggaaaa cgttcttcgg ggcgaaaact ctcaaggatc ttaccgctgt    5280
tgagatccag ttcgatgtaa cccactcgtg cacccaactg atcttcagca tcttttactt    5340
tcaccagcgt ttctgggtga gcaaaaacag gaaggcaaaa tgccgcaaaa aagggaataa    5400
gggcgacacg gaaatgttga atactcatac tcttcctttt tcaatattat tgaagcattt    5460
atcagggtta ttgtctcatg agcggataca tatttgaatg tatttagaaa aataaacaaa    5520
taggggttcc gcgcacattt ccccgaaaag tgccacctga acgaagcatc tgtgcttcat    5580
tttgtagaac aaaaatgcaa cgcgagagcg ctaattttc aaacaaagaa tctgagctgc     5640 attttttacag aacagaaatg caacgcgaaa gcgctatttt accaacgaag aatctgtgct    5700 tcattttttgt aaaacaaaaa tgcaacgcga gagcgctaat ttttcaaaca agaatctga    5760 gctgcatttt tacagaacag aaatgcaacg cgagagcgct attttaccaa caaagaatct    5820
atacttcttt tttgttctac aaaaatgcat cccgagagcg ctatttttct aacaaagcat    5880
cttagattac tttttttctc ctttgtgcgc tctataatgc agtctcttga taacttttttg    5940 cactgtaggt ccgttaaggt tagaagaagg ctactttggt gtctattttc tcttccataa    6000
aaaaagcctg actccacttc ccgcgtttac tgattactag cgaagctgcg ggtgcatttt    6060
ttcaagataa aggcatcccc gattatattc tataccgatg tggattgcgc atactttgtg    6120
aacagaaagt gatagcgttg atgattcttc attggtcaga aaattatgaa cggtttcttc    6180
tattttgtct ctatatacta cgtataggaa atgtttacat tttcgtattg ttttcgattc    6240
actctatgaa tagttcttac tacaattttt ttgtctaaag agtaatacta gagataaaca    6300
taaaaaatgt agaggtcgag tttagatgca agttcaagga gcgaaaggtg gatgggtagg    6360
ttatataggg atatagcaca gagatatata gcaaagagat acttttgagc aatgtttgtg    6420
gaagcggtat tcgcaatatt ttagtagctc gttacagtcc ggtgcgtttt tggttttttg    6480
aaagtgcgtc ttcagagcgc ttttggtttt caaaagcgct ctgaagttcc tatactttct    6540
agagaatagg aacttcggaa taggaacttc aaagcgtttc cgaaaacgag cgcttccgaa    6600
aatgcaacgc gagctgcgca catacagctc actgttcacg tcgcacctat atctgcgtgt    6660
tgcctgtata tatatataca tgagaagaac ggcatagtgc gtgtttatgc ttaaatgcgt    6720
acttatatgc gtctatttat gtaggatgaa aggtagtcta gtacctcctg tgatattatc    6780
ccattccatg cggggtatcg tatgcttcct tcagcactac cctttagctg ttctatatgc    6840
tgccactcct caattggatt agtctcatcc ttcaatgcta tcatttcctt tgatattgga    6900
tcatactaag aaaccattat tatcatgaca ttaacctata aaaataggcg tatcacgagg    6960
ccctttcgtc                                                          6970
```

<210> SEQ ID NO 85
<211> LENGTH: 5843
<212> TYPE: DNA
<213> ORGANISM: Artificial Sequence
<220> FEATURE:
<221> NAME/KEY: source
<222> LOCATION: 1..5843
<223> OTHER INFORMATION: /mol_type="DNA"
      /note="plasmid"
      /organism="Artificial Sequence"

<400> SEQUENCE: 85

```
cgcgtgcatt cctcgagtaa gcttggtacc gcggctagct aagatccgct ctaaccgaaa      60
aggaaggagt tagacaacct gaagtctagg tccctattta tttttttata gttatgttag     120
tattaagaac gttatttata tttcaaattt ttcttttttt tctgtacaga cgcgtgtacg     180
catgtaacat tatactgaaa accttgcttg agaaggtttt gggacgctcg aagatccagc     240
tgcattaatg aatcggccaa cgcgcgggga gaggcggttt gcgtattggg cgctcttccg     300
cttcctcgct cactgactcg ctgcgctcgg tcgttcggct gcggcgagcg gtatcagctc     360
actcaaaggc ggtaatacgg ttatccacag aatcagggga taacgcagga aagaacatgt     420
gagcaaaagg ccagcaaaag gccaggaacc gtaaaaaggc cgcgttgctg gcgttttttcc    480 ataggctccg ccccccctgac gagcatcaca aaaatcgacg ctcaagtcag aggtggcgaa    540
acccgacagg actataaaga taccaggcgt ttccccctgg aagctccctc gtgcgctctc     600
ctgttccgac cctgccgctt accggatacc tgtccgcctt ctcccttcg ggaagcgtgg      660 cgctttctca tagctcacgc tgtaggtatc tcagttcggt gtaggtcgtt cgctccaagc     720
tgggctgtgt gcacgaaccc cccgttcagc ccgaccgctg cgccttatcc ggtaactatc     780
gtcttgagtc aacccggta agacacgact tatcgccact ggcagcagcc actggtaaca     840
ggattagcag agcgaggtat gtaggcggtg ctacagagtt cttgaagtgg tggcctaact     900
acggctacac tagaaggaca gtatttggta tctgcgctct gctgaagcca gttaccttcg     960
gaaaaagagt tggtagctct tgatccggca aacaaaccac cgctggtagc ggtggttttt    1020
ttgtttgcaa gcagcagatt acgcgcagaa aaaaaggatc tcaagaagat cctttgatct    1080
tttctacggg gtctgacgct cagtggaacg aaaactcacg ttaagggatt ttggtcatga    1140
gattatcaaa aaggatcttc acctagatcc ttttaaatta aaaatgaagt tttaaatcaa    1200
tctaaagtat atatgagtaa acttggtctg acagttacca atgcttaatc agtgaggcac    1260
ctatctcagc gatctgtcta tttcgttcat ccatagttgc ctgactcccc gtcgtgtaga    1320
taactacgat acgggagggc ttaccatctg gccccagtgc tgcaatgata ccgcgagacc    1380
cacgctcacc ggctccagat ttatcagcaa taaaccagcc agccggaagg gccgagcgca    1440
gaagtggtcc tgcaacttta tccgcctcca tccagtctat taattgttgc cgggaagcta    1500
gagtaagtag ttcgccagtt aatagtttgc gcaacgttgt tgccattgct acaggcatcg    1560
tggtgtcacg ctcgtcgttt ggtatggctt cattcagctc cggttcccaa cgatcaaggc    1620
gagttacatg atccccatg ttgtgcaaaa aagcggttag ctccttcggt cctccgatcg     1680
ttgtcagaag taagttggcc gcagtgttat cactcatggt tatggcagca ctgcataatt    1740
ctcttactgt catgccatcc gtaagatgct tttctgtgac tggtgagtac tcaaccaagt    1800
cattctgaga atagtgtatg cggcgaccga gttgctcttg cccggcgtca atacgggata    1860
ataccgcgcc acatagcaga actttaaaag tgctcatcat tggaaaacgt tcttcggggc    1920
```

```
gaaaactctc aaggatctta ccgctgttga gatccagttc gatgtaaccc actcgtgcac    1980
ccaactgatc ttcagcatct tttactttca ccagcgtttc tgggtgagca aaaacaggaa    2040
ggcaaaatgc cgcaaaaaag ggaataaggg cgacacggaa atgttgaata ctcatactct    2100 tccttttttca atattattga agcatttatc agggttattg tctcatgagc ggatacatat   2160
ttgaatgtat ttagaaaaat aaacaaatag gggttccgcg cacatttccc cgaaaagtgc    2220
cacctgaacg aagcatctgt gcttcatttt gtagaacaaa aatgcaacgc gagagcgcta    2280 attttttcaaa caaagaatct gagctgcatt tttacagaac agaaatgcaa cgcgaaagcg   2340
ctattttacc aacgaagaat ctgtgcttca tttttgtaaa acaaaaatgc aacgcgagag    2400
cgctaatttt tcaaacaaag aatctgagct gcattttttac agaacagaaa tgcaacgcga   2460
gagcgctatt ttaccaacaa agaatctata cttcttttttt gttctacaaa aatgcatccc   2520
gagagcgcta tttttctaac aaagcatctt agattacttt ttttctcctt tgtgcgctct    2580
ataatgcagt ctcttgataa cttttttgcac tgtaggtccg ttaaggttag aagaaggcta   2640
ctttggtgtc tatttttctct tccataaaaa aagcctgact ccacttcccg cgtttactga   2700
ttactagcga agctgcgggt gcattttttc aagataaagg catccccgat tatattctat    2760
accgatgtgg attgcgcata ctttgtgaac agaaagtgat agcgttgatg attcttcatt    2820
ggtcagaaaa ttatgaacgg tttcttctat tttgtctcta tatactacgt ataggaaatg    2880
tttacatttt cgtattgttt tcgattcact ctatgaatag ttcttactac aattttttttg   2940 tctaaagagt aatactagag ataaacataa aaaatgtaga ggtcgagttt agatgcaagt    3000
tcaaggagcg aaaggtggat gggtaggtta tagggata tagcacagag atatatagca     3060
aagagatact tttgagcaat gtttgtggaa gcggtattcg caatatttta gtagctcgtt    3120
acagtccggt gcgtttttgg ttttttgaaa gtgcgtcttc agagcgcttt tggttttcaa    3180
aagcgctctg aagttcctat actttctaga gaataggaac ttcggaatag gaacttcaaa    3240
gcgtttccga aaacgagcgc ttccgaaaat gcaacgcgag ctgcgcacat acagctcact    3300
gttcacgtcg cacctatatc tgcgtgttgc ctgtatatat atatacatga gaagaacggc    3360
atagtgcgtg tttatgctta aatgcgtact tatatgcgtc tatttatgta ggatgaaagg    3420
tagtctagta cctcctgtga tattatccca ttccatgcgg ggtatcgtat gcttccttca    3480
gcactaccct ttagctgttc tatatgctgc cactcctcaa ttggattagt ctcatccttc    3540
aatgctatca tttcctttga tattggatca tactaagaaa ccattattat catgacatta    3600
acctataaaa ataggcgtat cacgaggccc tttcgtctcg cgcgtttcgg tgatgacggt    3660
gaaaacctct gacacatgca gctcccggag acggtcacag cttgtctgta agcggatgcc    3720
gggagcagac aagcccgtca gggcgcgtca gcgggtgttg gcgggtgtcg gggctggctt    3780
aactatgcgg catcagagca gattgtactg agagtgcacc ataccacagc ttttcaattc    3840
aattcatcat ttttttttta ttcttttttt tgatttcggt ttctttgaaa ttttttttgat   3900 tcggtaatct ccgaacagaa ggaagaacga aggaaggagc acagacttag attggtatat    3960
atacgcatat gtagtgttga agaaacatga aattgcccag tattcttaac ccaactgcac    4020
agaacaaaaa cctgcaggaa acgaagataa atcatgtcga aagctacata taggaacgt     4080 gctgctactc atcctagtcc tgttgctgcc aagctattta atatcatgca cgaaaagcaa    4140
acaaacttgt gtgcttcatt ggatgttcgt accaccaagg aattactgga gttagttgaa    4200
gcattaggtc ccaaaatttg tttactaaaa acacatgtgg atatcttgac tgatttttcc    4260
atggagggca cagttaagcc gctaaaggca ttatccgcca agtacaattt tttactcttc    4320
```

| | |
|---|---:|
| gaagacagaa aatttgctga cattggtaat acagtcaaat tgcagtactc tgcgggtgta | 4380 |
| tacagaatag cagaatgggc agacattacg aatgcacacg gtgtggtggg cccaggtatt | 4440 |
| gttagcggtt tgaagcaggc ggcagaagaa gtaacaaagg aacctagagg ccttttgatg | 4500 |
| ttagcagaat tgtcatgcaa gggctcccta tctactggag aatatactaa gggtactgtt | 4560 |
| gacattgcga agagcgacaa agattttgtt atcggcttta ttgctcaaag agacatgggt | 4620 |
| ggaagagatg aaggttacga ttggttgatt atgacacccg gtgtgggttt agatgacaag | 4680 |
| ggagacgcat tgggtcaaca gtatagaacc gtggatgatg tggtctctac aggatctgac | 4740 |
| attattattg ttggaagagg actatttgca aagggaaggg atgctaaggt agagggtgaa | 4800 |
| cgttacagaa aagcaggctg ggaagcatat ttgagaagat gcggccagca aaactaaaaa | 4860 |
| actgtattat aagtaaatgc atgtatacta aactcacaaa ttagagcttc aatttaatta | 4920 |
| tatcagttat taccctatgc ggtgtgaaat accgcacaga tgcgtaagga gaaaataccg | 4980 |
| catcaggaaa ttgtaaacgt taatattttg ttaaaattcg cgttaaattt ttgttaaatc | 5040 |
| agctcatttt ttaaccaata ggccgaaatc ggcaaaatcc cttataaatc aaaagaatag | 5100 |
| accgagatag ggttgagtgt tgttccagtt tggaacaaga gtccactatt aaagaacgtg | 5160 |
| gactccaacg tcaaagggcg aaaaaccgtc tatcagggcg atggcccact acgtgaacca | 5220 |
| tcaccctaat caagttttt ggggtcgagg tgccgtaaag cactaaatcg aaccctaaa | 5280 |
| gggagccccc gatttagagc ttgacgggga agccggcga acgtggcgag aaaggaaggg | 5340 |
| aagaaagcga aaggagcggg cgctagggcg ctggcaagtg tagcggtcac gctgcgcgta | 5400 |
| accaccacac ccgccgcgct taatgcgccg ctacagggcg cgtccattcg ccattcaggc | 5460 |
| tgcgcaactg ttgggaaggg cgatcggtgc gggcctcttc gctattacgc cagctgaatt | 5520 |
| ggagcgacct catgctatac ctgagaaagc aacctgacct acaggaaaga gttactcaag | 5580 |
| aataagaatt ttcgttttaa aacctaagag tcactttaaa atttgtatac acttattttt | 5640 |
| tttataactt atttaataat aaaaatcata aatcataaga aattcgctta tttagaagtg | 5700 |
| tcaacaacgt atctaccaac gatttgaccc ttttccatct tttcgtaaat ttctggcaag | 5760 |
| gtagacaagc cgacaaccct tgattggaga cttgaccaaac ctctggcgaa gaattgttaa | 5820 |
| ttaagagctc gaatgcgtgc gat | 5843 |

<210> SEQ ID NO 86
<211> LENGTH: 6050
<212> TYPE: DNA
<213> ORGANISM: Artificial Sequence
<220> FEATURE:
<221> NAME/KEY: source
<222> LOCATION: 1..6050
<223> OTHER INFORMATION: /mol_type="DNA"
    /note="plasmid"
    /organism="Artificial Sequence"

<400> SEQUENCE: 86

| | |
|---|---:|
| accaatgctt aatcagtgag gcacctatct cagcgatctg tctatttcgt tcatccatag | 60 |
| ttgcctgact ccccgtcgtg tagataacta cgatacggga gggcttacca tctggcccca | 120 |
| gcgctgcgat gataccgcga gaaccacgct caccggctcc ggatttatca gcaataaacc | 180 |
| agccagccgg aagggccgag cgcagaagtg gtcctgcaac tttatccgcc tccatccagt | 240 |
| ctattaattg ttgccgggaa gctagagtaa gtagttcgcc agttaatagt ttgcgcaacg | 300 |
| ttgttgccat cgctacaggc atcgtggtgt cacgctcgtc gtttggtatg gcttcattca | 360 |

| | |
|---|---|
| gctccggttc ccaacgatca aggcgagtta catgatcccc catgttgtgc aaaaaagcgg | 420 |
| ttagctcctt cggtcctccg atcgttgtca gaagtaagtt ggccgcagtg ttatcactca | 480 |
| tggttatggc agcactgcat aattctctta ctgtcatgcc atccgtaaga tgcttttctg | 540 |
| tgactggtga gtactcaacc aagtcattct gagaatagtg tatgcggcga ccgagttgct | 600 |
| cttgcccggc gtcaatacgg gataataccg cgccacatag cagaacttta aaagtgctca | 660 |
| tcattggaaa acgttcttcg gggcgaaaac tctcaaggat cttaccgctg ttgagatcca | 720 |
| gttcgatgta acccactcgt gcacccaact gatcttcagc atcttttact ttcaccagcg | 780 |
| tttctgggtg agcaaaaaca ggaaggcaaa atgccgcaaa aaagggaata agggcgacac | 840 |
| ggaaatgttg aatactcata ttcttccttt ttcaatatta ttgaagcatt tatcagggtt | 900 |
| attgtctcat gagcggatac atatttgaat gtatttagaa aaataaacaa ataggggtca | 960 |
| gtgttacaac caattaacca attctgaaca ttatcgcgag cccatttata cctgaatatg | 1020 |
| gctcataaca cccccttgttt gcctggcggc agtagcgcgg tggtcccacc tgacccatg | 1080 |
| ccgaactcag aagtgaaacg ccgtagcgcc gatggtagtg tggggactcc ccatgcgaga | 1140 |
| gtagggaact gccaggcatc aaataaaacg aaaggctcag tcgaaagact gggcctttcg | 1200 |
| cccgggctaa ttatggggtg tcgcccttat tcgactctat agtgaagttc ctattctcta | 1260 |
| gaaagtatag gaacttctga agtggggatt taaatgcggc cgcgctgagg gtttaatcgt | 1320 |
| ctatgaggag actgttagtt ggatatcagt aatgagacga aaaagctcga atgaatgga | 1380 |
| tatattcttt ttgctactgg caactgttga atatttaatg ttaaaacaaa ctaactgagg | 1440 |
| tatattcgta tctgtatgta cacatatact atatacagga aaagataagc aagagagagg | 1500 |
| atatcaacta cgagagcgat cgattatata tcaaaagctg tccgctttgc cacccataat | 1560 |
| cggcgcttag tttcggagtt caatcataat tctaccacct tacactcaac ttactcttta | 1620 |
| actcctatag tataatatcg ccactgaccc catattaaaa aatttttttg ctcgatcttc | 1680 |
| tatcctcttt aggttaattg tcgctgttat tgtctagatt ttttctcgga gatgcgcat | 1740 |
| ctatttgccg tcaaaagatc ctctcatacc atattaagta aattgcctcc atttctttt | 1800 |
| cctcgggcag agaaactcgc aggcaacttg ctctcgaagt ggtcacgtat taagtcctca | 1860 |
| gcgagctcgc atggaatgcg tgcgatgagc gacctcatgc tatacctgag aaagcaacct | 1920 |
| gacctacagg aaagagttac tcaagaataa gaattttcgt tttaaaacct aagagtcact | 1980 |
| ttaaaatttg tatacactta tttttttttat aacttattta ataataaaaa tcataaatca | 2040 |
| taagaaattc gcttatttag aagtgtcaac aacgtatcta ccaacggaat gcgtgcgatc | 2100 |
| gcgtgcattc atccgctcta accgaaaagg aaggagttag acaacctgaa gtctaggtcc | 2160 |
| ctatttattt ttttatagtt atgttagtat taagaacgtt atttatattt caaattttc | 2220 |
| ttttttttct gtacagacgc gtgtacgcat gtaacattat actgaaaacc ttgcttgaga | 2280 |
| aggttttggg acgctcgaag atcgcgtcag ctgaagcttc gtacgctgca ggtcgacaac | 2340 |
| ccttaatata acttcgtata atgtatgcta tacgaagtta ttaggtctag atcccaat | 2400 |
| acaacagatc acgtgatctt ttgtaagatg aagttgaagt gagtgttgca ccgtgccaat | 2460 |
| gcaggtggct attagattaa atatgtgatt tgttctatta agtttcctgt ataattaatg | 2520 |
| gggagcgctg attctctttt ggtacgcttc ccatccagca tttctgtatc tttcaccttc | 2580 |
| aaccttagga tctctaccct tggcgaaaag tcctctgcca acaatgatga tatctgatcc | 2640 |
| accacttaca acttcgtcga cggttctgta ctgctgaccc aatgcatcgc ctttgtcgtc | 2700 |
| taaacctaca cctgggggtca tgattagcca atcaaaccct tcttctcttc ctcccatatc | 2760 |

```
gttctgagca atgaacccaa taacgaaatc tttatcactc tttgcaatat caacggtacc   2820
cttagtatat tcaccgtgtg ctagagaacc cttggaagac aattcagcaa gcatcaataa   2880
tccccttggt tctttggtga cctcttgcgc accttgtttc aagccagcaa caataccagc   2940
accagtaacc ccgtgggcgt tggtgatatc agaccattct gcgatacggt aaacgcccga   3000
tgtatattgt aatttgactg tgttaccgat atcggcgaat tttctgtcct caaatatcaa   3060
gaacttgtat ttctctgcca atgctttcaa tggaacgaca gtaccctcat aactgaaatc   3120
atccaagata tcaacgtgtg ttttcaaaag gcaaatgtat ggacccaacg tttcaacaag   3180
tttcaatagc tcatcagtcg aacgaacgtc aagagaagca cacaaattgg tcttcttttc   3240
atccattaaa cgtaaaagtt tcgatgcaac cggacttgca tgagtctcag ctctactggt   3300
atatgatttt gtggacatgg tgcaactaat tgacgggagt gtattgacgc tggcgtactg   3360
gctttcacaa aatgggccaa tcacaaccac atcttagata gttgaaatga ctttagataa   3420
catcaattga tgagctta atcatgtcaa agctaaaagt gtcaccatga acgacaattc   3480
ttaagcaaat cacgtgatat agatccacga ataaccacca tttgatgctc gaggcaagta   3540
atgtgtgtaa aaaaatgcgt taccaccatc caatgcagac cgatcttcta cccagaatca   3600
catatattta tgtaccgagt accttttttc tatcttccaa ttgcttctcc catatgattg   3660
tctccgtaag ctcgaaattt ctaagttgga ttttaatctt cacgcaggat gacagttcga   3720
tgagcttctg aggagtgttt agaacataat cagtttatcc atggtctatc tcttcttgtc   3780
gctttttctc ctcgatagaa cctaaataaa acgagctctc gagaacccttt aatataactt   3840
cgtataatgt atgctatacg aagttattag gtgatatcag atccactagt ggcctatgca   3900
cccaattcgc cctatagtga gtcgtattac gcgcgctcac tggccgtcgt tttacaacgt   3960
cgtgactggg aaaaccctgg cgttacccct gcaggactag tgctgaggca ttaatcctgc   4020
ataatcggcc tcacagaggg atcccgttac ccatctatgc tgaagattta tcatactatt   4080
cctccgctcg tttcttttttt cagtgaggtg tgtcgtgaaa gaaaacccac aattaaactt   4140
tcaacaaccg ggcgactagg aagagagtag tgggcgcgga tgacgaaggc taaggtcact   4200
tcttcgtttc ctttattggg gtttccgtgt agccttcccc tgaatagtgt gggacgtttt   4260
atgagaagcc gtaagaaata ggcaaattga gttatgacaa gtagacatga tgccgcagcc   4320
ttgcctgact ttacgtctcc ttcatgaata agttttttcta tcgagttctt ttcctttttt   4380
cgccttaatt agctcaatta agcctgtcct cactactttt ctttttctta tcggctttgt   4440
gccacaccta accttcgaat gctgttttat tccgttctta catgggatgg taatgccttg   4500
gcgagattaa gacctcagcg cggccgcaaa tttaaataaa atgaagtgaa gttcctatac   4560
tttctagaga ataggaactt ctatagtgag tcgaataagg gcgacacaaa atttattcta   4620
aatgcataat aaatactgat aacatcttat agtttgtatt atattttgta ttatcgttga   4680
catgtataat tttgatatca aaaactgatt ttccctttat tattttcgag atttattttc   4740
ttaattctct ttaacaaact agaaatattg tatatacaaa aaatcataaa taatagatga   4800
atagtttaat tataggtgtt catcaatcga aaaagcaacg tatcttattt aaagtgcgtt   4860
gcttttttct catttataag gttaaataat tctcatatat caagcaaagt gacaggcgcc   4920
cttaaatatt ctgacaaatg ctctttccct aaactccccc cataaaaaaa cccgccgaag   4980
cgggttttta cgttatttgc ggattaacga ttactcgtta tcagaaccgc ccagggggcc   5040
cgagcttaag actggccgtc gttttacaac acagaaagag tttgtagaaa cgcaaaaagg   5100
```

-continued

| | | | | |
|---|---|---|---|---|
| ccatccgtca | ggggccttct | gcttagtttg | atgcctggca | gttccctact | ctcgccttcc | 5160 |
| gcttcctcgc | tcactgactc | gctgcgctcg | gtcgttcggc | tgcggcgagc | ggtatcagct | 5220 |
| cactcaaagg | cggtaatacg | gttatccaca | gaatcagggg | ataacgcagg | aaagaacatg | 5280 |
| tgagcaaaag | gccagcaaaa | ggccaggaac | cgtaaaaagg | ccgcgttgct | ggcgtttttc | 5340 |
| cataggctcc | gcccccctga | cgagcatcac | aaaaatcgac | gctcaagtca | gaggtggcga | 5400 |
| aacccgacag | gactataaag | ataccaggcg | tttccccctg | gaagctccct | cgtgcgctct | 5460 |
| cctgttccga | ccctgccgct | taccggatac | ctgtccgcct | ttctcccttc | gggaagcgtg | 5520 |
| gcgctttctc | atagctcacg | ctgtaggtat | ctcagttcgg | tgtaggtcgt | tcgctccaag | 5580 |
| ctgggctgtg | tgcacgaacc | ccccgttcag | cccgaccgct | gcgccttatc | cggtaactat | 5640 |
| cgtcttgagt | ccaacccggt | aagacacgac | ttatcgccac | tggcagcagc | cactggtaac | 5700 |
| aggattagca | gagcgaggta | tgtaggcggt | gctacagagt | tcttgaagtg | gtgggctaac | 5760 |
| tacggctaca | ctagaagaac | agtatttggt | atctgcgctc | tgctgaagcc | agttaccttc | 5820 |
| ggaaaaagag | ttggtagctc | ttgatccggc | aaacaaacca | ccgctggtag | cggtggtttt | 5880 |
| tttgtttgca | agcagcagat | tacgcgcaga | aaaaaggat | ctcaagaaga | tcctttgatc | 5940 |
| ttttctacgg | ggtctgacgc | tcagtggaac | gacgcgcgcg | taactcacgt | taagggattt | 6000 |
| tggtcatgag | cttgcgccgt | cccgtcaagt | cagcgtaatg | ctctgctttt | | 6050 |

<210> SEQ ID NO 87
<211> LENGTH: 6964
<212> TYPE: DNA
<213> ORGANISM: Artificial Sequence
<220> FEATURE:
<221> NAME/KEY: source
<222> LOCATION: 1..6964
<223> OTHER INFORMATION: /mol_type="DNA"
     /note="plasmid"
     /organism="Artificial Sequence"

<400> SEQUENCE: 87

| | | | | | |
|---|---|---|---|---|---|
| accaatgctt | aatcagtgag | gcacctatct | cagcgatctg | tctatttcgt | tcatccatag | 60 |
| ttgcctgact | ccccgtcgtg | tagataacta | cgatacggga | gggcttacca | tctggcccca | 120 |
| gcgctgcgat | gataccgcga | gaaccacgct | caccggctcc | ggatttatca | gcaataaacc | 180 |
| agccagccgg | aagggccgag | cgcagaagtg | gtcctgcaac | tttatccgcc | tccatccagt | 240 |
| ctattaattg | ttgccgggaa | gctagagtaa | gtagttcgcc | agttaatagt | ttgcgcaacg | 300 |
| ttgttgccat | cgctacaggc | atcgtggtgt | cacgctcgtc | gtttggtatg | gcttcattca | 360 |
| gctccggttc | ccaacgatca | aggcgagtta | catgatcccc | catgttgtgc | aaaaaagcgg | 420 |
| ttagctcctt | cggtcctccg | atcgttgtca | gaagtaagtt | ggccgcagtg | ttatcactca | 480 |
| tggttatggc | agcactgcat | aattctctta | ctgtcatgcc | atccgtaaga | tgcttttctg | 540 |
| tgactggtga | gtactcaacc | aagtcattct | gagaatagtg | tatgcggcga | ccgagttgct | 600 |
| cttgcccggc | gtcaatacgg | gataataccg | cgccacatag | cagaacttta | aaagtgctca | 660 |
| tcattggaaa | acgttcttcg | gggcgaaaac | tctcaaggat | cttaccgctg | ttgagatcca | 720 |
| gttcgatgta | acccactcgt | gcacccaact | gatcttcagc | atcttttact | ttcaccagcg | 780 |
| tttctgggtg | agcaaaaaca | ggaaggcaaa | atgccgcaaa | aaagggaata | agggcgacac | 840 |
| ggaaatgttg | aatactcata | ttcttccttt | ttcaatatta | ttgaagcatt | tatcagggtt | 900 |
| attgtctcat | gagcggatac | atatttgaat | gtatttagaa | aaataaacaa | ataggggtca | 960 |
| gtgttacaac | caattaacca | attctgaaca | ttatcgcgag | cccatttata | cctgaatatg | 1020 |

```
gctcataaca cccctttgttt gcctggcggc agtagcgcgg tggtcccacc tgacccatg    1080 ccgaactcag aagtgaaacg ccgtagcgcc gatggtagtg tggggactcc ccatgcgaga    1140
gtagggaact gccaggcatc aaataaaacg aaaggctcag tcgaaagact gggcctttcg    1200
cccgggctaa ttatggggtg tcgcccttat tcgactctat agtgaagttc ctattctcta    1260
gaaagtatag gaacttctga agtggggatt taaatgcggc cgcgctgagg gtttaatgga    1320
atagtgacgt tgtgatgcgg tgagttcggc ggttagggga atggtatatg ataaaaaacg    1380
gaaacgtgct tctttaattt aattgtttaa tattgttgca gatatataaa aaggggggaaa   1440 gaaccaaaga tgtaattatt tctttattgc ctcaacctaa agcaagcaat aaggtataga    1500
gatcaggacg tctcgagagc tgatatcaaa tttgaagcca cgcaagtaac tacgtaggtc    1560
agagggcaca aggaataaca cgtgacattt ttctttttc tttttttttt tttttttttt     1620
ttttgttagt cttggcttct gtgccgtagt ctgtatacgg ttttagatgc ggtatgttta    1680
tcatcgccca gaaatttgcg gggtgcaaag aaataaaatc cgtgctgaaa cccgtgctga    1740
aatccgtgca ccgcatcaaa ttttctcgga ggattctttg cagccggatt aagtcctcag    1800
cgagctcgca tggaatgcgt gcgatgagcg acctcatgct atacctgaga aagcaacctg    1860
acctacagga aagagttact caagaataag aattttcgtt ttaaaaccta agagtcactt    1920
taaaatttgt atacacttat ttttttttata acttatttaa taataaaaat cataaatcat   1980
aagaaattcg cttatttaga agtgtcaaca acgtatctac caacggaatg cgtgcgatcg    2040
cgtgcattca tccgctctaa ccgaaaagga aggagttaga caacctgaag tctaggtccc    2100
tatttatttt tttatagtta tgttagtatt aagaacgtta tttatatttc aaatttttct    2160 ttttttttctg tacagacgcg tgtacgcatg taacattata ctgaaaacct tgcttgagaa   2220
ggttttggga cgctcgaaga tcgcgtcagc tgaagcttcg tacgctgcag gtcgacaacc    2280
cttaatataa cttcgtataa tgtatgctat acgaagttat taggtctaga gatccgcagg    2340
ctaaccggaa cctgtattat ttagtttatg ctacgttaaa taaagacctt tcgttcacat    2400
aactgaatgt gtaatggcct tgagatttca agcataccaa gttggtggag acggggtcgt    2460
tacaaaagac tctttaagcc aagatttcct tgacagcctt ggcgatagca tcgccaacct    2520
cagtggtaga gttagaacca ccaaggtcac cggttctgac acctgcatcc aagacatttc    2580
taacagcttc ttcaagagcc ctaccttctt caaccaaatc caaggataac ttcaacatca    2640
tagctgcaga taagatggta gcaattgggt taaccttgtt tgctggtaaa tctggggcag    2700
aaccatgaca tggttcgtac aaaccgaatg ccttgttagt gtcaggtagg gaagctagag    2760
atgcagaagg taataaaccc aaagaacctg gaataacaga ggcttcatcg gagataatat    2820
caccaaacat gttgttggta ataacaacac cgtttagctt agttggtgat ttaaccaaaa    2880
tcatagcagc agagtcgatc aattggtgct gaacagttaa ttgtgggaac tcagtcttga    2940
tggtttcttc aacagtcttt ctccacaatc tggaagaggc aagcacgtta gccttgtcaa    3000
gagaccagat tggtaatggt gggttttgtt gcaatgccaa gaaagcagcc attcttgtaa    3060
ttctttgaac ttcaggaaca ctgtatttct cagagtccca agcaactccg tcaccttcat    3120
cttcttttct ttcaccaaag tagataccac caaccaattc tctaacgacg acgaaatcgg    3180 tacccttttgc atattcaggc ttcaaaggag aaagatctag taaagaatca gaagcaaagt    3240
tacatggtct caagttggcg tatagaccca attccttttct gatcttcaat agaccttgtt   3300
ctggtctaac tgcgcccgta ccccattttg gaccaccaac agcacctagt aagacagcat    3360
```

```
cggctttctt agaggcttct agagcttcat ctggtaaagg agtgccagtg gcatcgatgg    3420 cagcacccee gatcaagtga tgttggaaat tgaacttaat ttctggacgg acttcagcaa    3480
tggcattcaa gaccttaata gcttcgtcag taacttcttt accgacgtga tcacccggta    3540
ggacaacgat attcttagac atggtataat ctgtgtagtg tgggatactt tttacttctt    3600
caaataggta tcaacaataa aaataaatcg aagcaaatgt aggaatgcgt taaagcagat    3660
gtacttactt agagtacata gatatattta tataattcaa tatataaaag tatatgaagc    3720
atctgatgtt gaacctgtca tgactctaaa ctggaatggg tagttatgct tctgaaggtt    3780
ttccgttaga aaatgagtgc agggatcagg cccggaaccg ttttagcct  gaaaggaaaa    3840 gaaaaaaatg cggtgattac tagcacgtga ctgcgctgaa ttggaatcca ccacaagtac    3900
agcgaatggc aagagggaag gggaatatat tgtgcctggc ggtagtctgc tatatcaaat    3960
gttaaacata actaaatgca gtagtgaata gagtaatgta tttctacata tgtgggtagg    4020
gccaatggga gcccgatgtc tattgtacag atattttcct tttatagtta atcaattcaa    4080
cttggaaatc attgagtcga tatctacttg gataactgga gccgtggcag cgtttgaaat    4140
ttgacgagtc ttcttgtttt gttcgcgcat tttcagttta ttcaaacggg agatggcacc    4200
gaatccactg acttctctgt tcaatttgaa tggtaatagg aagaaagtac atttcgagaa    4260
attttcgccc aacgtcgaaa tctcatggat gatatcctcg atacaaatga caccttcatc    4320
acctaatttc tcttcaacga tattgttgtc attcaagatt atctcttttg gttctttatc    4380
ttctggcctt tgccacatta ttctagatct cttttggatt aaagaacgga tagatgcaag    4440
tgaaggttgt ccgataacaa tatatggtga tacaagtttc aacaatgggt acacgtcctt    4500
ggtaagtttg atgaaaacac cagtgttcaa ctcaacaagt ctcaaaagag ataacacttt    4560
gtaagccttt gctgggatct tcacagcgag ctctcgagaa cccttaatat aacttcgtat    4620
aatgtatgct atacgaagtt attaggtagg tgatatcaga tccactagtg gcctatgcac    4680
ccaattcgcc ctatagtgag tcgtattacg cgcgctcact ggccgtcgtt ttacaacgtc    4740
gtgactggga aaccctggcg ttacccctg  caggactagt gctgaggcat taatcttcca    4800
cggaatacca agcccattgc atcgcgatgt tagtttagcg gagtttcttg gcattggcaa    4860
atctctgcta aatgctgcgt acagacggaa actcacaccg ccgcgaagac tggtcagtgg    4920
caaaaaaaaa ataaaatat  agaaaataac tattacgtat gttactgttt ctggtagttg    4980
atatgaagtt ggagttgtat attgtacgct ttaggaacag ggaagtgaat attatttact    5040
ctgctgcaca ttctggctag gtcgaagccg aacttgaga  agacgccgcg ctagaactat    5100
ggaccaagct gttgacaatg ttcagatggt gatgcaccta ccctgtgcgg ggagtggcca    5160
cggacgcgag cggaaggtgc ggaaggtgcg gaaggtgcgg gagttgcggg aggttcttcg    5220
ctaagcgtga gggttgctag ctggggcggc ggggtttccc taagtgtaaa taaggcctcg    5280
gctggcacat gagtcgccgg aggaggcggc ggaggcgacg acgctaaaac cgtgccgtt    5340 ggggaaggat gggcggctat atctaccatt gacctgatgg ggactcggtt cttaaggaat    5400
gggtttgagg tgggtgtgga ttaagacctc agcgcggccg caaatttaaa taaaatgaag    5460
tgaagttcct atactttcta gagaatagga acttctatag tgagtcgaat aagggcgaca    5520
caaaatttat tctaaatgca taataaatac tgataacatc ttatagtttg tattatattt    5580
tgtattatcg ttgacatgta taattttgat atcaaaaact gattttccct ttattatttt    5640
cgagatttat ttcttaatt  ctctttaaca aactagaaat attgtatata caaaaaatca    5700
taaataatag atgaatagtt taattatagg tgttcatcaa tcgaaaaagc aacgtatctt    5760
```

```
atttaaagtg cgttgctttt ttctcattta taaggttaaa taattctcat atatcaagca      5820
aagtgacagg cgcccttaaa tattctgaca aatgctcttt ccctaaactc cccccataaa      5880
aaaacccgcc gaagcgggtt tttacgttat ttgcggatta acgattactc gttatcagaa      5940
ccgcccaggg ggcccgagct taagactggc cgtcgtttta caacacagaa agagtttgta      6000
gaaacgcaaa aaggccatcc gtcagggggcc ttctgcttag tttgatgcct ggcagttccc     6060
tactctcgcc ttccgcttcc tcgctcactg actcgctgcg ctcggtcgtt cggctgcggc      6120
gagcggtatc agctcactca aaggcggtaa tacggttatc cacagaatca ggggataacg      6180
caggaaagaa catgtgagca aaaggccagc aaaaggccag gaaccgtaaa aaggccgcgt      6240
tgctggcgtt tttccatagg ctccgccccc ctgacgagca tcacaaaaat cgacgctcaa      6300
gtcagaggtg gcgaaacccg acaggactat aaagatacca ggcgtttccc cctggaagct      6360
ccctcgtgcg ctctcctgtt ccgaccctgc cgcttaccgg atacctgtcc gcctttctcc      6420
cttcgggaag cgtggcgctt tctcatagct cacgctgtag gtatctcagt tcggtgtagg      6480
tcgttcgctc caagctgggc tgtgtgcacg aaccccccgt tcagcccgac cgctgcgcct      6540
tatccggtaa ctatcgtctt gagtccaacc cggtaagaca cgacttatcg ccactggcag      6600
cagccactgg taacaggatt agcagagcga ggtatgtagg cggtgctaca gagttcttga      6660
agtggtgggc taactacggc tacactagaa gaacagtatt tggtatctgc gctctgctga      6720
agccagttac cttcggaaaa agagttggta gctcttgatc cggcaaacaa accaccgctg      6780
gtagcggtgg tttttttgtt tgcaagcagc agattacgcg cagaaaaaaa ggatctcaag      6840
aagatccttt gatcttttct acggggtctg acgctcagtg gaacgacgcg cgcgtaactc      6900
acgttaaggg attttggtca tgagcttgcg ccgtcccgtc aagtcagcgt aatgctctgc      6960
tttt                                                                  6964
```

<210> SEQ ID NO 88
<211> LENGTH: 6972
<212> TYPE: DNA
<213> ORGANISM: Artificial Sequence
<220> FEATURE:
<221> NAME/KEY: source
<222> LOCATION: 1..6972
<223> OTHER INFORMATION: /mol_type="DNA"
      /note="plasmid"
      /organism="Artificial Sequence"

<400> SEQUENCE: 88

```
accaatgctt aatcagtgag gcacctatct cagcgatctg tctatttcgt tcatccatag       60
ttgcctgact ccccgtcgtg tagataacta cgatacggga gggcttacca tctggcccca      120
gcgctgcgat gataccgcga gaaccacgct caccggctcc ggatttatca gcaataaacc      180
agccagccgg aagggccgag cgcagaagtg gtcctgcaac tttatccgcc tccatccagt      240
ctattaattg ttgccgggaa gctagagtaa gtagttcgcc agttaatagt ttgcgcaacg      300
ttgttgccat cgctacaggc atcgtggtgt cacgctcgtc gtttggtatg gcttcattca      360
gctccggttc ccaacgatca aggcgagtta catgatcccc catgttgtgc aaaaaagcgg      420
ttagctcctt cggtcctccg atcgttgtca gaagtaagtt ggccgcagtg ttatcactca      480
tggttatggc agcactgcat aattctctta ctgtcatgcc atccgtaaga tgcttttctg      540
tgactggtga gtactcaacc aagtcattct gagaatagtg tatgcggcga ccgagttgct      600
cttgcccggc gtcaatacgg gataataccg cgccacatag cagaacttta aaagtgctca      660
```

```
tcattggaaa acgttcttcg gggcgaaaac tctcaaggat cttaccgctg ttgagatcca    720
gttcgatgta acccactcgt gcacccaact gatcttcagc atcttttact ttcaccagcg    780
tttctgggtg agcaaaaaca ggaaggcaaa atgccgcaaa aagggaata agggcgacac    840
ggaaatgttg aatactcata ttcttccttt ttcaatatta ttgaagcatt tatcagggtt    900
attgtctcat gagcggatac atatttgaat gtatttagaa aaataaacaa ataggggtca    960
gtgttacaac caattaacca attctgaaca ttatcgcgag cccatttata cctgaatatg   1020
gctcataaca ccccttgttt gcctggcggc agtagcgcgg tggtcccacc tgaccccatg   1080
ccgaactcag aagtgaaacg ccgtagcgcc gatggtagtg tggggactcc ccatgcgaga   1140
gtagggaact gccaggcatc aaataaaacg aaaggctcag tcgaaagact gggcctttcg   1200
cccgggctaa ttatggggtg tcgcccttat tcgactctat agtgaagttc ctattctcta   1260
gaaagtatag gaacttctga agtggggatt taaatgcggc cgcgctgagg gtttaatgtt   1320
gagctctgtc cttcatggac tttttggacc acttcttctt ggacttctta ccaccagcaa   1380
gagcggcagc ggctttggca gctttagaca attgttgctt tggaggcatg ttatattatg   1440
ttctgagacg taagaaaggg tgaaaattga tgttagtgtc aaaaattata ttacaaaata   1500
cgcagagata ttctagttcc tttgatgaat gaatctttca gaaaaaaaag tcaaagcaaa   1560
agcaaaatgg cctgcagact aaactgtatg gtggtcttgg aatgataaag atctgtttaa   1620
tagatttagt agatacaata gcacatctca ttacccagtt atgattgacg tcattctgag   1680
ttacaatgat cttagcgacc tgtgctcatt atttgctcca ctaattctaa ttttcctcgc   1740
ctttcatatt tcgtatcttt attctatatc ctaaaatttt tttggcaaat cccagatttg   1800
gctttgattt tggcatcggt tcggttcttt cattaagtcc tcagcgagct cgcatggaat   1860
gcgtgcgatg agcgacctca tgctatacct gagaaagcaa cctgacctac aggaaagagt   1920
tactcaagaa taagaatttt cgttttaaaa cctaagagtc actttaaaat ttgtatacac   1980
ttatttttt tataacttat ttaataataa aaatcataaa tcataagaaa ttcgcttatt   2040
tagaagtgtc aacaacgtat ctaccaacgg aatgcgtgcg atcgcgtgca ttcatccgct   2100
ctaaccgaaa aggaaggagt tagacaacct gaagtctagg tccctattta ttttttttata   2160
gttatgttag tattaagaac gttatttata tttcaaattt ttctttttttt tctgtacaga   2220
cgcgtgtacg catgtaacat tatactgaaa accttgcttg agaaggtttt gggacgctcg   2280
aagatcgcgt cagctgaagc ttcgtacgct gcaggtcgac aacccttaat ataacttcgt   2340
ataatgtatg ctatacgaag ttattaggtc tagagatccg caggctaacc ggaacctgta   2400
ttatttagtt tatgctacgt taaataaaga cctttcgttc acataactga atgtgtaatg   2460
gccttgagat ttcaagcata ccaagttggt ggagacgggg tcgttacaaa agactcttta   2520
agccaagatt tccttgacag ccttggcgat agcatcgcca acctcagtgg tagagttaga   2580
accaccaagg tcaccggttc tgacacctgc atccaagaca tttctaacag cttcttcaag   2640
agccctacct tcttcaacca aatccaagga taacttcaac atcatagctg cagataagat   2700
ggtagcaatt gggttaacct tgtttgctgg taaatctggg gcagaaccat gacatggttc   2760
gtacaaaccg aatgccttgt tagtgtcagg tagggaagct agagatgcag aaggtaataa   2820
acccaaagaa cctggaataa cagaggcttc atcggagata atatcaccaa acatgttgtt   2880
ggtaataaca acaccgttta gcttagttgg tgatttaacc aaaatcatag cagcagagtc   2940
gatcaattgg tgctgaacag ttaattgtgg gaactcagtc ttgatggttt cttcaacagt   3000
cttttctccac aatctggaag aggcaagcac gttagccttg tcaagagacc agattggtaa   3060
```

```
tggtgggttt tgttgcaatg ccaagaaagc agccattctt gtaattcttt gaacttcagg    3120
aacactgtat ttctcagagt cccaagcaac tccgtcacct tcatcttctt ttctttcacc    3180
aaagtagata ccaccaacca attctctaac gacgacgaaa tcggtaccct ttgcatattc    3240
aggcttcaaa ggagaaagat ctagtaaaga atcagaagca aagttacatg gtctcaagtt    3300
ggcgtataga cccaattcct ttctgatctt caatagacct tgttctggtc taactgcgcc    3360
cgtaccccat tttggaccac caacagcacc tagtaagaca gcatcggctt tcttagaggc    3420
ttctagagct tcatctggta aaggagtgcc agtggcatcg atggcagcac ccccgatcaa    3480
gtgatgttgg aaattgaact taatttctgg acggacttca gcaatggcat tcaagacctt    3540
aatagcttcg tcagtaactt ctttaccgac gtgatcaccc ggtaggacaa cgatattctt    3600
agacatggta taatctgtgt agtgtgggat acttttttact tcttcaaata ggtatcaaca    3660
ataaaaataa atcgaagcaa atgtaggaat gcgttaaagc agatgtactt acttagagta    3720
catagatata tttatataat tcaatatata aaagtatatg aagcatctga tgttgaacct    3780
gtcatgactc taaactggaa tgggtagtta tgcttctgaa ggttttccgt tagaaaatga    3840
gtgcagggat caggcccgga accggtttta gcctgaaagg aaaagaaaaa aatgcggtga    3900
ttactagcac gtgactgcgc tgaattggaa tccaccacaa gtacagcgaa tggcaagagg    3960 gaagggggaat atattgtgcc tggcggtagt ctgctatatc aaatgttaaa cataactaaa    4020
tgcagtagtg aatagagtaa tgtatttcta catatgtggg tagggccaat gggagcccga    4080
tgtctattgt acagatattt tcctttttata gttaatcaat tcaacttgga aatcattgag    4140
tcgatatcta cttggataac tggagccgtg gcagcgtttg aaatttgacg agtcttcttg    4200
ttttgttcgc gcattttcag tttattcaaa cgggagatgg caccgaatcc actgacttct    4260
ctgttcaatt tgaatggtaa taggaagaaa gtacatttcg agaaattttc gcccaacgtc    4320
gaaatctcat ggatgatatc ctcgatacaa atgacacctt catcacctaa tttctcttca    4380
acgatattgt tgtcattcaa gattatctct tttggttctt tatcttctgg cctttgccac    4440
attattctag atctctttttg gattaaaaga cggatagatg caagtgaagg ttgtccgata    4500
acaatatatg gtgatacaag tttcaacaat gggtacacgt ccttggtaag tttgatgaaa    4560
acaccagtgt tcaactcaac aagtctcaaa agagataaca cttttgtaagc ctttgctggg    4620 atcttcacag cgagctctcg agaacccctta atataacttc gtataatgta tgctatacga    4680
agttattagg taggtgatat cagatccact agtggcctat gcacccaatt cgccctatag    4740
tgagtcgtat tacgcgcgct cactggccgt cgttttacaa cgtcgtgact gggaaaaccc    4800
tggcgttacc cctgcaggac tagtgctgag gcattaatct tcccgtgaat caactgcaca    4860
taccttaata actagttcag tttagtgctc tgtctgagtg actgtaataa taaattttac    4920
aagccacttc tcatgacata tattggtaag taacttcatc aatactaatt agtctttgcc    4980
ggttacccat ctggccctg acttgcgatg cttaggaagt tccatactcg cggctcttcc    5040
caacagtagc acatccgtga aacttctggc gctattcatt atgcagtacc aggacaagaa    5100
gttaaaaaaa aagctctgtt acaagttcaa tggtggtgca aggattgaag ttattatcca    5160
ggaggcacgg atgcaaaaga tagaagacaa attaatttcc ttaaaattca aaatgctcat    5220
tattgtcacg ctgtatgagc atttggtgaa gatttcactg ggaaatgttg caataatttg    5280
ataatcgttc gtattggatg aaactgtaac atcatctgtt tattaagtat ccgtgttatt    5340
agtatatcat cacatacggt gtaagaagat aacataaaga ttgagaaaca gtcatcaaat    5400
```

```
ataatggaag ctgaaatgcg aggattgatt aagacctcag cgcggccgca aatttaaata    5460
aaatgaagtg aagttcctat actttctaga gaataggaac ttctatagtg agtcgaataa    5520
gggcgacaca aaatttattc taaatgcata ataaatactg ataacatctt atagtttgta    5580
ttatattttg tattatcgtt gacatgtata attttgatat caaaaactga ttttcccttt    5640
attattttcg agatttattt tcttaattct ctttaacaaa ctagaaatat tgtatataca    5700
aaaaatcata ataatagat gaatagttta attataggtg ttcatcaatc gaaaaagcaa     5760
cgtatcttat ttaaagtgcg ttgcttttt ctcatttata aggttaaata attctcatat     5820
atcaagcaaa gtgacaggcg cccttaaata ttctgacaaa tgctctttcc ctaaactccc    5880
cccataaaaa aacccgccga agcgggtttt tacgttattt gcggattaac gattactcgt    5940
tatcagaacc gcccagggg cccgagctta agactggccg tcgttttaca acacagaaag     6000
agtttgtaga aacgcaaaaa ggccatccgt cagggggcctt ctgcttagtt tgatgcctgg   6060
cagttcccta ctctcgcctt ccgcttcctc gctcactgac tcgctgcgct cggtcgttcg    6120
gctgcggcga gcggtatcag ctcactcaaa ggcggtaata cggttatcca cagaatcagg    6180
ggataacgca ggaaagaaca tgtgagcaaa aggccagcaa aaggccagga accgtaaaaa    6240
ggccgcgttg ctggcgtttt tccataggct ccgcccccct gacgagcatc acaaaaatcg    6300
acgctcaagt cagaggtggc gaaacccgac aggactataa agataccagg cgtttccccc    6360
tggaagctcc ctcgtgcgct ctcctgttcc gaccctgccg cttaccggat acctgtccgc    6420
ctttctccct tcgggaagcg tggcgctttc tcatagctca cgctgtaggt atctcagttc    6480
ggtgtaggtc gttcgctcca agctgggctg tgtgcacgaa ccccccgttc agcccgaccg    6540
ctgcgcctta tccggtaact atcgtcttga gtccaacccg gtaagacacg acttatcgcc    6600
actggcagca gccactggta acaggattag cagagcgagg tatgtaggcg gtgctacaga    6660
gttcttgaag tggtgggcta actacggcta cactagaaga acagtatttg gtatctgcgc    6720
tctgctgaag ccagttacct tcggaaaaag agttggtagc tcttgatccg gcaaacaaac    6780
caccgctggt agcggtggtt ttttgtttg caagcagcag attacgcgca gaaaaaagg     6840 atctcaagaa gatcctttga tctttcctac ggggtctgac gctcagtgga acgacgcgcg    6900
cgtaactcac gttaagggat tttggtcatg agcttgcgcc gtcccgtcaa gtcagcgtaa    6960
tgctctgctt tt                                                         6972
```

<210> SEQ ID NO 89
<211> LENGTH: 5864
<212> TYPE: DNA
<213> ORGANISM: Artificial Sequence
<220> FEATURE:
<221> NAME/KEY: source
<222> LOCATION: 1..5864
<223> OTHER INFORMATION: /mol_type="DNA"
    /note="plasmid"
    /organism="Artificial Sequence"

<400> SEQUENCE: 89

```
accaatgctt aatcagtgag gcacctatct cagcgatctg tctatttcgt tcatccatag      60
ttgcctgact ccccgtcgtg tagataacta cgatacggga gggcttacca tctggcccca    120
gcgctgcgat gataccgcga gaaccacgct caccggctcc ggatttatca gcaataaacc    180
agccagccgg aagggccgag cgcagaagtg gtcctgcaac tttatccgcc tccatccagt    240
ctattaattg ttgccgggaa gctagagtaa gtagttcgcc agttaatagt ttgcgcaacg    300
ttgttgccat cgctacaggc atcgtggtgt cacgctcgtc gtttggtatg gcttcattca    360
```

```
gctccggttc caacgatca aggcgagtta catgatcccc catgttgtgc aaaaaagcgg      420
ttagctcctt cggtcctccg atcgttgtca gaagtaagtt ggccgcagtg ttatcactca      480
tggttatggc agcactgcat aattctctta ctgtcatgcc atccgtaaga tgcttttctg      540
tgactggtga gtactcaacc aagtcattct gagaatagtg tatgcggcga ccgagttgct      600
cttgcccggc gtcaatacgg gataataccg cgccacatag cagaacttta aaagtgctca      660
tcattggaaa acgttcttcg gggcgaaaac tctcaaggat cttaccgctg ttgagatcca      720
gttcgatgta acccactcgt gcacccaact gatcttcagc atcttttact ttcaccagcg      780
tttctgggtg agcaaaaaca ggaaggcaaa atgccgcaaa aaagggaata agggcgacac      840
ggaaatgttg aatactcata ttcttccttt tcaatatta ttgaagcatt tatcagggtt      900
attgtctcat gagcggatac atatttgaat gtatttagaa aaataaacaa ataggggtca      960
gtgttacaac caattaacca attctgaaca ttatcgcgag cccatttata cctgaatatg     1020
gctcataaca ccccttgttt gcctggcggc agtagcgcgg tggtcccacc tgaccccatg     1080
ccgaactcag aagtgaaacg ccgtagcgcc gatggtagtg tggggactcc ccatgcgaga     1140
gtagggaact gccaggcatc aaataaaacg aaaggctcag tcgaaagact gggcctttcg     1200
cccgggctaa ttatggggtg tcgcccttat tcgactctat agtgaagttc ctattctcta     1260
gaaagtatag gaacttctga agtggggatt taaatgcggc cgcgctgagg gtttaatccc     1320
aaagctaaga gtcccatttt attcttctat atgtatattt tcgatactct aaaccaccct     1380
acaatgtagc cctatactaa atctgctcaa ttttcagctt ctacaagtga ctcgagacca     1440
cgtggaaaga tccaactact ccagcacaac gattcaatat aatcgattgc tccactcata     1500
agaggcaaga acaagcttca acttttggta agccgccgtt tataaacagg gaagatgtcc     1560
tttgtcaagg gaggcacaga gcatggccaa tttggcaaat gcaggttttt ctgagtgaa     1620 aaatgaaaaa gcattgtagt agagtcggct cactgaaaaa ccggggagga cgaaaaggtt     1680
tccagccaca gttgtagtca cgtgcgcgcc atgctgacta atggcagccg tcgttgggca     1740
gaagagaatt agtatggtac aggatacgct aattgcgctc caactaccaa ggttgttgag     1800
ggaacactgg ggcaataggc tgtcgccatt caagagcaga ttaagtcctc agcgagctcg     1860
catggaatgc gtgcgatgag cgacctcatg ctatacctga gaaagcaacc tgacctacag     1920
gaaagagtta ctcaagaata agaattttcg ttttaaaacc taagagtcac tttaaaattt     1980
gtatacactt atttttttta aacttatttt aataataaaa atcataaatc ataagaaatt     2040
cgcttattta gaagtgtcaa caacgtatct accaacggaa tgcgtgcgat cgcgtgcatt     2100
catccgctct aaccgaaaag gaaggagtta gacaacctga agtctaggtc cctatttatt     2160
tttttatagt tatgttagta ttaagaacgt tatttatatt tcaaattttt ctttttttc     2220 tgtacagacg cgtgtacgca tgtaacatta tactgaaaac cttgcttgag aaggttttgg     2280
gacgctcgaa gatcgcgtca gctgaagctt cgtacgctgc aggtcgacaa cccttaatat     2340
aacttcgtat aatgtatgct atacgaagtt attaggtcta gagatctgtt tagcttgcct     2400
cgtccccgcc gggtcacccg gccagcgaca tggaggccca gaataccctc cttgacagtc     2460
ttgacgtgcg cagctcaggg gcatgatgtg actgtcgccc gtacatttag cccatacatc     2520
cccatgtata atcatttgca tccatacatt ttgatggccg cacggcgcga agcaaaaatt     2580
acggctcctc gctgcagacc tgcgagcagg gaaacgctcc cctcacagac gcgttgaatt     2640
gtccccacgc cgcgcccctg tagagaaata taaaaggtta ggatttgcca ctgaggttct     2700
```

```
tctttcatat acttccttt aaaatcttgc taggatacag ttctcacatc acatccgaac    2760
ataaacaacc atgggtagga gggcttttgt agaaagaaat acgaacgaaa cgaaaatcag    2820
cgttgccatc gctttggaca aagctccctt acctgaagag tcgaatttta ttgatgaact    2880
tataacttcc aagcatgcaa accaaaaggg agaacaagta atccaagtag acacgggaat    2940
tggattcttg gatcacatgt atcatgcact ggctaaacat gcaggctgga gcttacgact    3000
ttactcaaga ggtgatttaa tcatcgatga tcatcacact gcagaagata ctgctattgc    3060
acttggtatt gcattcaagc aggctatggg taactttgcc ggcgttaaaa gatttggaca    3120
tgcttattgt ccacttgacg aagctctttc tagaagcgta gttgacttgt cgggacggcc    3180
ctatgctgtt atcgatttgg gattaaagcg tgaaaaggtt ggggaattgt cctgtgaaat    3240
gatccctcac ttactatatt cctttcggt agcagctgga attactttgc atgttacctg    3300
cttatatggt agtaatgacc atcatcgtgc tgaaagcgct tttaaatctc tggctgttgc    3360
catgcgcgcg gctactagtc ttactggaag ttctgaagtc ccaagcacga agggagtgtt    3420
gtaaagagta ctgacaataa aaagattctt gttttcaaga acttgtcatt tgtatagttt    3480
ttttatattg tagttgttct attttaatca aatgttagcg tgatttatat tttttttcgc    3540
ctcgacatca tctgcccaga tgcgaagtta agtgcgcaga aagtaatatc atgcgtcaat    3600
cgtatgtgaa tgctggtcgc tatactgctg tcgattcgat actaacgccg ccatccagtt    3660
taaacgagct ctcgagaacc cttaatataa cttcgtataa tgtatgctat acgaagttat    3720
taggtgatat cagatccact agtggcctat gcacccaatt cgccctatag tgagtcgtat    3780
tacgcgcgct cactggccgt cgttttacaa cgtcgtgact gggaaaaccc tggcgttacc    3840
cctgcaggac tagtgctgag gcattaataa caggcatggg aagattcgct ttttttttt    3900 gaattacaat agtatgtctg atgtctgcaa gaagtaacag gcgtgtgcac aagaatacgt    3960
gtgtgtgcgt aagcgtatgc actggtggca taacttatct aagaagtata tatcactgac    4020
atagaaatgt agatatacag gtattttct cgataatcga taaaaatctc gtcgcgctga    4080
accaaacttg gtggttacgg agagttttc tctcatcatt actgtctttc gcattgattt    4140
cccctttgac cgataaaatc ccttggattc ataagattaa acaagaggt gatcaaagag    4200 aaccctgtga agtttatgt ttataaccgg gcataaagtg aactagacac tttcaagaag    4260
ccaaccaaag catgagtaac gaagcttacc agcatgatca taccgtaaat cctcaccaga    4320
ttaagacctc agcgcggccg caaatttaaa taaaatgaag tgaagttcct atactttcta    4380
gagaatagga acttctatag tgagtcgaat aagggcgaca caaaatttat tctaaatgca    4440
taataaatac tgataacatc ttatagtttg tattatattt tgtattatcg ttgacatgta    4500
taattttgat atcaaaaact gattttccct ttattatttt cgagatttat ttcttaatt    4560 ctctttaaca aactagaaat attgtatata caaaaaatca taataatag atgaatagtt    4620 taattatagg tgttcatcaa tcgaaaaagc aacgtatctt atttaaagtg cgttgctttt    4680
ttctcattta aaggttaaa taattctcat atatcaagca aagtgacagg cgcccttaaa    4740
tattctgaca aatgctcttt ccctaaactc cccccataaa aaacccgcc gaagcgggtt    4800 tttacgttat tgcggatta acgattactc gttatcagaa ccgcccaggg ggcccgagct    4860
taagactggc cgtcgtttta caacacagaa agagtttgta gaaacgcaaa aaggccatcc    4920
gtcaggggcc ttctgcttag tttgatgcct ggcagttccc tactctcgcc ttccgcttcc    4980
tcgctcactg actcgctgcg ctcggtcgtt cggctgcggc gagcggtatc agctcactca    5040
aaggcggtaa tacggttatc cacagaatca ggggataacg caggaaagaa catgtgagca    5100
```

-continued

```
aaaggccagc aaaaggccag gaaccgtaaa aaggccgcgt tgctggcgtt tttccatagg    5160
ctccgccccc ctgacgagca tcacaaaaat cgacgctcaa gtcagaggtg gcgaaacccg    5220
acaggactat aaagatacca ggcgtttccc cctggaagct ccctcgtgcg ctctcctgtt    5280
ccgaccctgc cgcttaccgg atacctgtcc gcctttctcc cttcgggaag cgtggcgctt    5340
tctcatagct cacgctgtag gtatctcagt tcggtgtagg tcgttcgctc caagctgggc    5400
tgtgtgcacg aaccccccgt tcagcccgac cgctgcgcct tatccggtaa ctatcgtctt    5460
gagtccaacc cggtaagaca cgacttatcg ccactggcag cagccactgg taacaggatt    5520
agcagagcga ggtatgtagg cggtgctaca gagttcttga agtggtgggc taactacggc    5580
tacactagaa gaacagtatt tggtatctgc gctctgctga agccagttac cttcggaaaa    5640
agagttggta gctcttgatc cggcaaacaa accaccgctg gtagcggtgg ttttttttgtt   5700 tgcaagcagc agattacgcg cagaaaaaaa ggatctcaag aagatccttt gatcttttct    5760
acggggtctg acgctcagtg gaacgacgcg cgcgtaactc acgttaaggg attttggtca    5820
tgagcttgcg ccgtcccgtc aagtcagcgt aatgctctgc tttt                     5864
```

GENETICALLY ENGINEERED YEAST

CROSS REFERENCE TO RELATED APPLICATIONS

This application is the National Phase entry of PCT/EP2013/071163, which claims priority to European Patent Application No. 12188198.1, filed Oct. 11, 2012. The content of these applications is incorporated herein by reference in their entirety.

The present invention relates to genetically engineered yeasts and their use in methods for production of 3-hydroxypropionic acid (3HP).

3HP is a platform chemical, which can be converted to acrylic acid, 1,3-propandiol, malonic acid, and other valuable products. Acrylic acid-derived products include superabsorbent polymers used in baby diapers and incontinence products, various plastics, coatings, adhesives, elastomers, and paints. Currently acrylic acid is derived from propylene, a by-product of ethylene and gasoline production. Establishment of 3HP production from glucose or other renewable carbon source would provide a biosustainable alternative to acrylic acid production from fossil resources. Several methods for production of 3HP from glucose have been described. The specific teachings however primarily use the bacterium *Escherichia coli* as the host. The present invention uses yeast as the host for 3HP production. This allows executing the process at low pH and thus makes it overall more economical.

US2010/0136638 describes, in general terms, production of 3-HP in micro-organisms including yeast by biocatalysis from beta-alanine. It is said that beta-alanine can be synthesized in cells from alpha-alanine by an enzyme having alanine 2,3-aminomutase activity, and sequences are given for relevant enzymes.

Also disclosed are methods of producing 3-HP from beta-alanine using beta-alanine/pyruvate aminotransferase (BAPAT) sequences. Transformed cells having BAPAT activity, which allows the cell to convert beta-alanine to 3-HP through a malonate semialdehyde intermediate, are disclosed.

Although the possibility of conducting such work in yeast is mentioned, there is no practical demonstration of this. We have found that enzymes in this pathway that are effective in *E. coli* are not effective in *Saccharomyces cerevisiae*. In particular, according to US2010/0136638 enzymes having BAPAT activity can be obtained from *Pseudomonas putida* or *Pseudomonas aeruginosa*. However, we have found that genes encoding these enzymes are not effective in *S. cerevisiae*.

Malonate semialdehyde (or malonic semialdehyde or 3-oxopropanoic acid) is a key intermediate in one pathway leading to 3HP, but many different routes to its production are possible.

US2012135481 describes a 3HP producing pathway in yeast including genes encoding gabT, 3-HPDH and HIBADH and others. However, other and better 3HP producing yeasts are needed.

We have now found that 3HP production from beta-alanine was obtained in yeast *S. cerevisiae* when an uncharacterized aminotransferase yhxA from *Bacillus cereus* AH1272 was heterologously expressed. The amino acid sequence of the said yhxA encoded aminotransferase is set out in SEQ ID NO1 and the DNA sequence is set out in SEQ ID NO2. SEQ ID NO2 is codon-optimized for *S. cerevisiae*.

It is our belief that the said aminotransferase YhxA from *Bacillus cereus* AH1272 catalyzes a transamination reaction between beta-alanine and pyruvate leading to L-alanine and malonic semialdehyde, in which case the enzyme would be beta-alanine-pyruvate aminotransferase E.C. 2.6.1.18 (BAPAT) rather than a gabT (E.C. 2.6.1.19).

US2012/0135481 discloses genetically modified yeast cells comprising an active 3-HP fermentation pathway including the BAAT gene (beta alanine amino transferase—EC 2.6.1.19) which catalyzes the conversion of [beta]-alanine to malonate semialdehyde. BAAT here is therefore synonymous with naturally occurring or genetically modified gabT. However, successful production of 3-HP by this method is not shown.

WO2005/118719 discloses, but does not demonstrate the effectiveness of, methods of producing 3-HP from beta-alanine using beta-alanine/pyruvate aminotransferase (BAPAT) sequences from any organism in a yeast cell. Identified sources for BAPAT here include *Pseudomonas, Arabidopsis*, rat and *Xenopus*. As mentioned above, we have established that a BAPAT genes from *Pseudomonas* is not effective in *S. cerevisiae*.

The Uniprot entry for yhxA provides a sequence but does not identify the enzyme as being a BAPAT.

Accordingly, the present invention now provides a genetically modified yeast cell comprising an active fermentation pathway producing 3-HP, wherein the cell comprises and expresses an exogenous gene coding for the production of an enzyme having at least 80% identity with SEQ ID NO: 1 and catalysing a transamination reaction between beta-alanine and pyruvate to produce malonate semialdehyde.

Preferably, said yeast also expresses 3-hydroxyisobutyrate dehydrogenase (HIBADH), suitably from *Pseudomonas aeruginosa, P. putida, Bacillus cereus*, or *Candida albicans* and/or 3-hydroxypropanoate dehydrogenase (3-HPDH), optionally from *Metallosphaera sedula, Sulfolobus tokadaii* or *E. coli*.

To enable the synthesis of 3-hydroxypropionic acid directly from glucose is it preferred in addition to reconstructing pathway from beta-alanine to 3-hydroxypropionic acid to express heterologous aspartate 1-decarboxylase, preferably from insect, preferably red flour beetle (*Tribolium castaneum*). To further increase the flux towards 3-hydroxypropinic acid it is preferred to overexpress pyruvate carboxylase and or PEP carboxylase and aspartate aminotransferase. Additionally deletion of pyruvate decarboxylase activity (PDC1, PDC5, PDC6) or alcohol dehydrogenase (ADH) activity would allow anaerobic fermentation without formation of ethanol as a by-product.

Strains according to the invention can be evolved using adaptive laboratory evolution methods to improve glucose tolerance, remove acetate dependence and increase 3HP production.

The yeast is preferably *S. cerevisiae* but may be *Saccharomyces kluyveri, Yarrowia lipolytica, Schizosaccharomyces pombe, Debaryomyces hansenii, Cyberlindnera jadinii, Rhodotula minuta, Rhodotula glutinis, Torulaspora delbrueckii, Pichia stipitis, Pichia pastoris, Kluyveromyces lactis, Kluyveromyces marxianus*, or other yeast.

Yeast strains suitable for modification according to the invention can be selected for their tolerance to growth in the presence of 3HP.

The amino acid sequence of the native yhxA expression product of *B. cereus* AH1272 and the DNA sequence coding for it can be modified for use in this invention in various ways. First, the DNA sequence can be codon optimised for expression in the appropriate yeast. Secondly, the amino acid sequence may be modified by deletion, addition, or substitution of amino acids whilst not interfering with, or indeed whilst increasing, the enzyme activity. Such a modified enzyme may have at least 80%, more preferably at least 85%, or 90% or 95% homology with the native amino acid sequence.

The invention includes a method for the production of 3HP comprising culturing a yeast cell of the invention, and optionally recovering 3HP from the culture. The culture may be conducted in a culture medium including beta-alanine or a source thereof other than said yeast. Said source may be another micro-organism. However, the yeast of the invention may be engineered to produce beta-alanine, e.g. from L-aspartate, suitably by incorporating exogenous genes producing aspartate-1-decarboxylase (EC 4.1.1.11) or glutamate decarboxylase (EC 4.1.1.15) or from L-alanine by 2,3-alanine aminomutase. Due to its role in the synthesis of pantothenate, aspartate 1-decarboxylase is also known as PanD. A gene for this enzyme is not present in the genome of wild-type S. cerevisiae.

We have found that superior results are obtained using certain exogenous PanD genes encoding aspartate-1-decarboxylase compared to others. In particular, we have found that PanD genes from insects, especially flour beetles, more especially red flour beetle (*Tribolium castaneum*), provides better production titres and better yields of 3-HP compared to bacterial PanD genes.

Preferably, the production of 3HP by said yeast is such that at least 100 mg of 3HP per liter of culture medium is produced or is recovered from said culture medium, more preferably at least 200, or 300, or 400 or 500 or 1000 or 2000 or 14000 mg/l.

The invention will be further described and illustrated in the following non-limiting examples, in which reference will be made to the following Tables.

TABLE 1

Primers

| Primer name | Primer sequence, 5' → 3' | |
|---|---|---|
| pE1_fw | AGTGCAGGU GGTACCAAAACAATG | SEQ ID NO 26 |
| pE1_rv | CGTGCGAU GTCGACTCA | SEQ ID NO 27 |
| EcRutE_U1_fw | AGTGCAGGU AAAACAATGAACGAAGCCGTTAG | SEQ ID NO 28 |
| EcRutE_U1_rv | CGTGCGAU TTACAACAGCCCGCAG | SEQ ID NO 29 |
| EcYdfG_U1_fw | AGTGCAGGU AAAACAATGATCGTTTTAGTAACTGG | SEQ ID NO 30 |
| EcYdfG_U1_rv | CGTGCGAU TTACTGACGGTGGACATTC | SEQ ID NO 31 |
| scGabT_U1_fw | AGTGCAGGU AAAACAATGTCTATTTGTGAACAATACTAC | SEQ ID NO 32 |
| ScGabT_U1_rv | CGTGCGAU TCATAATTCATTAACTGATTTGG | SEQ ID NO 33 |
| GeneArt_1U_fw | AGTGCAGGU GCATGGTACCAAAACAATG | SEQ ID NO 34 |
| GeneArt_1U_rv | CGTGCGAU ATGAGGCCCAGGTCGAC | SEQ ID NO 35 |
| PTEF1_fw | ACCTGCACU TTGTAATTAAAACTTAG | SEQ ID NO 36 |
| PTEF1_rv | CACGCGAU GCACACACCATAGCTTC | SEQ ID NO 37 |
| ydfG_KpnI_express_fw | AAAA GGTACC ATGATCGTTTTAGTAACTGG | SEQ ID NO 38 |
| ydfG_PacI_express_rv | AAAA TTAATT AATTACTGACGGTGGACATTC | SEQ ID NO 39 |
| EcPAND_U1_fw | AGTGCAGGU AAAACAATGATCAGAACCATG | SEQ ID NO 40 |
| EcPAND_U1_rv | CGTGCGAU TCAAGCAACTTGAACTGG | SEQ ID NO 41 |
| CgPAND_U1_fw | AGTGCAGGU AAAACAATGTTGAGAACC | SEQ ID NO 42 |
| CgPAND_U1_rv | CGTGCGAU TCAAATGGATCTAGAAGTC | SEQ ID NO 43 |
| RnGAD1_U1_fw | AGTGCAGGU AAAACAATGGCTTCTTCTACTC | SEQ ID NO 44 |
| RnGAD1_U1_rv | CGTGCGAU TCACAAATCTTGACCCAATC | SEQ ID NO 45 |
| ScGAD1_U1_fw | AGTGCAGGU AAAACAATGTTACACAGGCACGGTTC | SEQ ID NO 46 |
| ScGAD1_U1_rv | CGTGCGAU TCAACATGTTCCTCTATAGTTTCTC | SEQ ID NO 47 |
| EcGAD1_U1_fw | AGTGCAGGU AAAACAATGGACCAGAAGCTGTTAAC | SEQ ID NO 48 |
| EcGAD1_U1_rv | CGTGCGAU TCAGGTGTGTTTAAAGCTG | SEQ ID NO 49 |
| pE2_fw | ATCTGTCAU GGTACCAAAACAATG | SEQ ID NO 60 |
| pE2_rv | CACGCGAU GTCGACTCA | SEQ ID NO 61 |

TABLE 1-continued

Primers

| Primer name | Primer sequence, 5' → 3' | |
|---|---|---|
| EcYdfg_U2_fw | ATCTGTCAU AAAACAATGATCGTTTTAGTAACTGGAG | SEQ ID NO 62 |
| EcYdfg_U2_rv | CACGCGAU TTACTGACGGTGGACATTC | SEQ ID NO 63 |
| PTEF1_fw | ACCTGCACU TTGTAATTAAAACTTAG | SEQ ID NO 64 |
| PPGK1_rv | ATGACAGAU TTGTTTTATATTTGTTG | SEQ ID NO 65 |
| TcPAND_U1_fw | AGTGCAGGU AAAACAATGCCAGCTACTGGTG | SEQ ID NO 70 |
| TcPAND_U1_rv | CGTGCGAU TCACAAATCGGAACCCAATC | SEQ ID NO 71 |
| ScPYC1_U1_fw | AGTGCAGGU AAAACA ATGTCGCAAAGAAAATTCG | SEQ ID NO 72 |
| ScPYC1_U1_rv | CGTGCGAU TCATGCCTTAGTTTCAACAG | SEQ ID NO 73 |
| ScPYC2_U2_fw | ATCTGTCAU AAAACA ATGAGCAGTAGCAAGAAATTG | SEQ ID NO 74 |
| ScPYC2_U2_rv | CACGCGAUTTACTTTTTTGGGATGGG | SEQ ID NO 75 |
| ScAAT2_U1_fw | AGTGCAGGU AAAACA ATGTCTGCCACTCTGTTCA | SEQ ID NO 76 |
| ScAAT2_U1_rv | CGTGCGAU TTACAATTTAGCTTCAATAGTATAG | SEQ ID NO 77 |

TABLE 2

Intermediate plasmids

| Plasmid name | Parent plasmid | Synthetic gene sequence cloned |
|---|---|---|
| pE1-PpBAPAT | pE1 | SEQ ID NO 4 |
| pE1-PaHIBADH | pE1 | SEQ ID NO 6 |
| pE1-CaHIBADH | pE1 | SEQ ID NO 8 |
| pE1-PpHIBADH | pE1 | SEQ ID NO 10 |
| pE1-BcHIBADH | pE1 | SEQ ID NO 12 |
| pE1-MsHPDH | pE1 | SEQ ID NO 14 |
| pE1-StMSR | pE1 | SEQ ID NO 16 |
| pE1-CaGabT | pE1 | SEQ ID NO 18 |
| pE2-MsHPDH | pE2 | SEQ ID NO 14 |

TABLE 3

Primers and templates used to generate gene fragments for USER cloning by PCR

| Fragment name | Gene | Fw_primer | Rv_primer | Template DNA |
|---|---|---|---|---|
| PaHIBADH<- | 3-hydroxyisobutyrate dehydrogenase from Pseudomonas aeruginosa | pE1_fw | pE1_rv | pE1-PaHIBADH |
| CaHIBADH<- | 3-hydroxyisobutyrate dehydrogenase from Candida albicans | pE1_fw | pE1_rv | pE1-CaHIBADH |
| BcHIBADH<- | 3-hydroxyisobutyrate dehydrogenase from Bacillus cereus | pE1_fw | pE1_rv | pE1-BcHIBADH |
| PpHIBADH<- | 3-hydroxyisobutyrate dehydrogenase from Pseudomonas putida | pE1_fw | pE1_rv | pE1-PpHIBADH |
| MsHPDH<- | 3-hydroxypropanoate dehydrogenase from Metallosphaera sedula | pE1_fw | pE1_rv | pE1-MsHPDH |
| StMSR<- | 3-hydroxypropanoate dehydrogenase from Sulfolobus tokadaii | pE1_fw | pE1_rv | pE1-StMSR |
| EcRutE<- | 3-hydroxypropanoate dehydrogenase from Escherichia coli | EcRutE_U1_fw | EcRutE_U1_rv | gDNA of E. coli SEQ ID NO 20 |
| EcYdfG<- | 3-hydroxypropanoate dehydrogenase from Escherichia coli | EcYdfG_U1_fw | EcYdfG_U1_rv | gDNA of E. coli SEQ ID NO 22 |
| PpBAPAT<- | Beta-alanine-pyruvate aminotransferase from Pseudomonas putida KT2440 | pE1_fw | pE1_rv | pE1-PpBAPAT |

TABLE 3-continued

Primers and templates used to generate gene fragments for USER cloning by PCR

| Fragment name | Gene | Fw_primer | Rv_primer | Template DNA |
| --- | --- | --- | --- | --- |
| BcBAPAT<- | Uncharacterized aminotransferase yhxA from *Bacillus cereus* AH1272 | GeneArt_1U_fw | GeneArt_1U_rv | GeneArt plasmid with synthetic gene sequence SEQ ID NO 2. |
| ScGabT<- | Gamma-aminobutyrate transaminase uga1 from *S. cerevisiae* | ScGabT_U1_fw | ScGabT_U1_rv | gDNA of *S. cerevisiae* CEN.PK113-7D SEQ ID NO 24 |
| CaGabT<- | Gamma-aminobutyrate transaminase from *Clostridium acetobutylicum* ATCC 824 (as control) | pE1_fw | pE1_rv | pE1-CaGabT |
| ScPTEF1<- | Promoter of tef1 gene from *S. cerevisiae* | PTEF1_fw | PTEF1_rv | gDNA of *S. cerevisiae* CEN.PK113-7D SEQ ID NO 25 |
| EcPanD<- | Aspartate 1-decarboxylase panD from *E. coli* | EcPAND_U1_fw | EcPAND_U1_rv | gBLOCK from Integrated DNA Technologies SEQ ID NO 50 |
| CgPanD<- | Aspartate 1-decarboxylase panD from *C. glutamicum* | CgPAND_U1_fw | CgPAND_U1_rv | gBLOCK from Integrated DNA Technologies SEQ ID NO 51 |
| ScGAD1<- | Glutamate decarboxylase gad1 from *S. cerevisiae* | ScGAD1_U1_fw | ScGAD1_U1_rv | gDNA of *S. cerevisiae* CEN.PK113-7D SEQ ID NO 52 |
| EcGAD1<- | Glutamate decarboxylase gad1 from *E. coli* | EcGAD1_U1_fw | EcGAD1_U1_rv | gDNA of *E. coli* SEQ ID NO 53 |
| RnGAD1<- | Glutamate decarboxylase gad1 from *R. norvegicus* | RnGAD1_U1_fw | RnGAD1_U1_rv | GeneArt plasmid with synthetic gene sequence SEQ ID NO 54 |
| MsHPDH-> | 3-hydroxypropanoate dehydrogenase from *Metallosphaera sedula* | pE2_fw | pE2_rv | pE2-MsHPDH |
| EcYdfG-> | 3-hydroxypropanoate dehydrogenase from *Escherichia coli* | EcYdfG_U2_fw | EcYdfG_U2_rv | gDNA of *E. coli* SEQ ID NO 22 |
| <-ScPTEF1-ScPPGK1-> | Fused promoters of tef1 and pgk1 genes from *S. cerevisiae* | PTEF1_fw | PPGK1_rv | plasmid pSP-GM1 SEQ ID NO 66 |
| TcPanD<- | Aspartate 1-decarboxylase from *T. castaneum* | TcPAND_U1_fw | TcPAND_U1_rv | GeneArt plasmid with synthetic gene sequence SEQ ID 69 |
| ScPYC1<- | Pyruvate carboxylase PYC1 from *S. cerevisiae* | ScPYC1_U1_fw | ScPYC1_U1_rv | gDNA of *S. cerevisiae* CEN.PK113-7D SEQ ID 78 |
| ScPYC2-> | Pyruvate carboxylase PYC2 from *S. cerevisiae* | ScPYC2_U2_fw | ScPYC2_U2_rv | gDNA of *S. cerevisiae* CEN.PK113-7D SEQ ID 79 |
| ScAAT2<- | Aspartate aminotransferase AAT2 from *S. cerevisiae* | ScAAT2_U1_fw | ScAAT2_U1_rv | gDNA of *S. cerevisiae* CEN.PK113-7D SEQ ID 80 |

TABLE 4

Expression plasmids

| Plasmid name | Parent plasmid | Selection marker | Cloned fragment(-s) | Promoter | Terminator |
|---|---|---|---|---|---|
| pPaHIBADH | pESC-HIS-USER | SpHIS5 | PaHIBADH<- | ScPTEF1<- | ScTADH1 |
| pCaHIBADH | pESC-HIS-USER | SpHIS5 | CaHIBADH<- | ScPTEF1<- | ScTADH1 |
| pBcHIBADH | pESC-HIS-USER | SpHIS5 | BcHIBADH<- | ScPTEF1<- | ScTADH1 |
| pPpHIBADH | pESC-HIS-USER | SpHIS5 | PpHIBADH<- | ScPTEF1<- | ScTADH1 |
| pMsHPDH | pESC-HIS-USER | SpHIS5 | MsHPDH<- | ScPTEF1<- | ScTADH1 |
| pStMSR | pESC-HIS-USER | SpHIS5 | StMSR<- | ScPTEF1<- | ScTADH1 |
| pEcRutE | pESC-HIS-USER | SpHIS5 | EcRutE<- | ScPTEF1<- | ScTADH1 |
| pEcYdfG | pESC-HIS-USER | SpHIS5 | EcYdfG<- | ScPTEF1<- | ScTADH1 |
| pPpBAPAT | pESC-URA-USER | KlURA3 | PpBAPAT<- | ScPTEF1<- | ScTADH1 |
| pBcBAPAT | pESC-URA-USER | KlURA3 | BcBAPAT<- | ScPTEF1<- | ScTADH1 |
| pScGabT | pESC-LEU-USER | KlURA2 | ScGabT<- | ScPTEF1<- | ScTADH1 |
| pCaGabT | pESC-LEU-USER | KlURA2 | CaGabT<- | ScPTEF1<- | ScTADH1 |
| pESC-URA-BcBAPAT-MsHDPH | pEEG-URA-USER | KlURA3 | BcBAPAT<-, MsHPDH-> | <-ScPTEF1-ScPPGK1-> | ScTADH1, ScTCYC1 |
| pESC-URA-BcBAPAT-EcYdfG | pESC-URA-USER | KlURA3 | BcBAPAT<-, EcYdfG-> | <-ScPTEF1-ScPPGK1-> | ScTADH1, ScTCYC1 |
| pESC-HIS-EcPanD | pESC-HIS-USER | SpHIS5 | EcPanD<- | ScPTEF1<- | ScTADH1 |
| pESC-HIS-CgPanD | pESC-HIS-USER | SpHIS5 | CgPanD<- | ScPTEF1<- | ScTADH1 |
| pESC-HIS-TcPanD | pESC-HIS-USER | SpHIS5 | TcPanD<- | ScPTEF1<- | ScTADH1 |
| pESC-HIS-ScGAD1 | pESC-HIS-USER | SpHIS5 | ScGAD1<- | ScPTEF1<- | ScTADH1 |
| pESC-HIS-EcGAD1 | pESC-HIS-USER | SpHIS5 | EcGAD1<- | ScPTEF1<- | ScTADH1 |
| pESC-HIS-RnGAD1 | pESC-HIS-USER | SpHIS5 | RnGAD1<- | ScPTEF1<- | ScTADH1 |
| pXI-1-LoxP-KlLEU2-PYC1<-PTEF1-PPGK1->PYC2 | pXI-1-LoxP-KlLEU2 (SEQ ID NO 87) | KlLEU2 | ScPYC1<-, ScPYC2-> | <-ScPTEF1-ScPPGK1-> | ScTADH1, ScTCYC1 |
| pX-2-LoxP-KlURA3-BcBAPAT<-PTEF1-PPGK1->EcYdfG | pX-2-LoxP-KlURA3 (SEQ ID NO 86) | KlURA3 | BcBAPAT<-, EcYdfG-> | <-ScPTEF1-ScPPGK1-> | ScTADH1, ScTCYC1 |
| pTY-BcBAPAT<-PTEF1-PPGK1->EcYdfG | pTY* | KlURA3-tagged | BcBAPAT<-, EcYdfG-> | <-ScPTEF1-ScPPGK1-> | ScTADH1, ScTCYC1 |
| pTY-TcPanD<-PTEF1 | pTY | KlURA3-tagged | TcPanD<- | ScPTEF1<- | ScTADH1 |
| pX-4-LoxP-SpHIS5-TcPanD<-PTEF1 | pX-4-LoxP-SpHIS5 (SEQ ID NO 89) | SpHIS5 | TcPanD<- | ScPTEF1<- | ScTADH1 |
| pX-4-LoxP-SpHIS5-BcBAPAT<-PTEF1-PPGK1->EcYdfG | pX-4-LoxP-SpHIS5 | SpHIS5 | BcBAPAT<-, EcYdfG-> | <-ScPTEF1-ScPPGK1-> | ScTADH1, ScTCYC1 |
| pXII-1-LoxP-KlLEU2-AAT2<-PTEF1 | pXII-1-LoxP-KlLEU2 (SEQ ID NO 88) | KlLEU2 | ScAAT2<- | ScPTEF1<- | ScTADH1 |

*pTY, a vector designed for multiple chromosomal integration by targeting TY repeat regions.

The vector contains the same USER cloning cassette as the rest of the parent plasmids listed in Table 4.

TABLE 5

Strains and 3HP titers in cultivation with β-alanine addition

| Parent strain | Plasmid with URA3 marker | Plasmid with HIS3 marker | Plasmid with LEU2 marker | 3HP, mg/L |
|---|---|---|---|---|
| CEN.PK113-11C (ura-his-) | pPpBAPAT | pPaHIBADH | — | −10 ± 2 |
| CEN.PK113-11C (ura-his-) | pPpBAPAT | pCaHIBADH | — | −16 ± 3 |
| CEN.PK113-11C (ura-his-) | pPpBAPAT | pBcHIBADH | — | −11 ± 5 |
| CEN.PK113-11C (ura-his-) | pPpBAPAT | pPpHIBADH | — | −10 ± 1 |
| CEN.PK113-11C (ura-his-) | pPpBAPAT | pMsHPDH | — | −12 ± 6 |
| CEN.PK113-11C (ura-his-) | pPpBAPAT | pStMSR | — | −4 ± 4 |
| CEN.PK113-11C (ura-his-) | pPpBAPAT | pEcRutE | — | −6 ± 5 |
| CEN.PK113-11C (ura-his-) | pPpBAPAT | pEcYdfG | — | −14 ± 2 |

TABLE 5-continued

Strains and 3HP titers in cultivation with β-alanine addition

| Parent strain | Plasmid with URA3 marker | Plasmid with HIS3 marker | Plasmid with LEU2 marker | 3HP, mg/L |
|---|---|---|---|---|
| CEN.PK113-11C (ura-his-) | pBcBAPAT | pPaHIBADH | — | 474 ± 15 |
| CEN.PK113-11C (ura-his-) | pBcBAPAT | pCaHIBADH | — | 489 ± 73 |
| CEN.PK113-11C (ura-his-) | pBcBAPAT | pBcHIBADH | — | 434 ± 29 |
| CEN.PK113-11C (ura-his-) | pBcBAPAT | pPpHIBADH | — | 496 ± 14 |
| CEN.PK113-11C (ura-his-) | pBcBAPAT | pMsHPDH | — | 1,852 ± 103 |
| CEN.PK113-11C (ura-his-) | pBcBAPAT | pStMSR | — | 1,445 ± 40 |
| CEN.PK113-11C (ura-his-) | pBcBAPAT | pEcRutE | — | 394 ± 8 |
| CEN.PK113-11C (ura-his-) | pBcBAPAT | pEcYdfG | — | 2,145 ± 89 |
| CEN.PK102-5B.URA3 (his-leu-) | — | pPaHIBADH | pCaGabT | −7 ± 4 |
| CEN.PK102-5B.URA3 (his-leu-) | — | pCaHIBADH | pCaGabT | −1 ± 5 |
| CEN.PK102-5B.URA3 (his-leu-) | — | pBcHIBADH | pCaGabT | 19 ± 20 |
| CEN.PK102-5B.URA3 (his-leu-) | — | pPpHIBADH | pCaGabT | −9 ± 0 |
| CEN.PK102-5B.URA3 (his-leu-) | — | pMsHPDH | pCaGabT | −9 ± 4 |
| CEN.PK102-5B.URA3 (his-leu-) | — | pStMSR | pCaGabT | −5 ± 4 |
| CEN.PK102-5B.URA3 (his-leu-) | — | pEcRutE | pCaGabT | 6 ± 2 |
| CEN.PK102-5B.URA3 (his-leu-) | — | pEcYdfG | pCaGabT | −10 ± 2 |
| CEN.PK102-5B.URA3 (his-leu-) | — | pPaHIBADH | pScGabT | 233 ± 17 |
| CEN.PK102-5B.URA3 (his-leu-) | — | pCaHIBADH | pScGabT | 205 ± 29 |
| CEN.PK102-5B.URA3 (his-leu-) | — | pBcHIBADH | pScGabT | 191 ± 19 |
| CEN.PK102-5B.URA3 (his-leu-) | — | pPpHIBADH | pScGabT | 202 ± 11 |
| CEN.PK102-5B.URA3 (his-leu-) | — | pMsHPDH | pScGabT | 493 ± 23 |
| CEN.PK102-5B.URA3 (his-leu-) | — | pStMSR | pScGabT | 435 ± 23 |
| CEN.PK102-5B.URA3 (his-leu-) | — | pEcRutE | pScGabT | 170 ± 11 |
| CEN.PK102-5B.URA3 (his-leu-) | — | pEcYdfG | pScGabT | 457 ± 18 |

TABLE 6

Strains and 3HP titers in cultivation with L-aspartate addition

| Parent strain | Plasmid with URA3 marker | Plasmid with HIS3 marker | 3HP, mg/L |
|---|---|---|---|
| CEN.PK113-11C (ura-his-) | pESC-URA-BcBAPAT-MsHDPH | pESC-HIS-EcPanD | −1 ± 0 |
| CEN.PK113-11C (ura-his-) | pESC-URA-BcBAPAT-MsHDPH | pESC-HIS-CgPanD | 79 ± 8 |
| CEN.PK113-11C (ura-his-) | pESC-URA-BcBAPAT-MsHDPH | pESC-HIS-ScGAD1 | 0 ± 0 |
| CEN.PK113-11C (ura-his-) | pESC-URA-BcBAPAT-MsHDPH | pESC-HIS-EcGAD1 | 0 ± 0 |
| CEN.PK113-11C (ura-his-) | pESC-URA-BcBAPAT-MsHDPH | pESC-HIS-RnGAD1 | −1 ± 0 |
| CEN.PK113-11C (ura-his-) | pESC-URA-BcBAPAT-EcYdfG | pESC-HIS-EcPanD | −1 ± 0 |
| CEN.PK113-11C (ura-his-) | pESC-URA-BcBAPAT-EcYdfG | pESC-HIS-CgPanD | 269 ± 53 |

TABLE 6-continued

Strains and 3HP titers in cultivation with L-aspartate addition

| Parent strain | Plasmid with URA3 marker | Plasmid with HIS3 marker | 3HP, mg/L |
|---|---|---|---|
| CEN.PK113-11C (ura-his-) | pESC-URA-BcBAPAT-EcYdfG | pESC-HIS-ScGAD1 | 0 ± 0 |
| CEN.PK113-11C (ura-his-) | pESC-URA-BcBAPAT-EcYdfG | pESC-HIS-EcGAD1 | 0 ± 0 |
| CEN.PK113-11C (ura-his-) | pESC-URA-BcBAPAT-EcYdfG | pESC-HIS-RnGAD1 | 0 ± 1 |
| CEN.PK113-5D (ura-) | pESC-URA-BcBAPAT-EcYdfG | — | 1 ± 0 |
| CEN.PK113-7D (WT) | — | — | 0 ± 0 |

TABLE 7

Strains and 3HP titers in cultivation on glucose as the sole carbon source

| Parent strain | Plasmid with URA3 marker | Plasmid with HIS3 marker | 3HP, mg/L on Delft medium | 3HP, mg/L on FIT medium |
|---|---|---|---|---|
| CEN.PK113-11C (ura-his-) | pESC-URA-BcBAPAT-EcYdfG | pESC-HIS-TcPanD | 605 ± 18 | 1638 ± 19 |
| CEN.PK113-11C (ura-his-) | pESC-URA-BcBAPAT-EcYdfG | pESC-HIS-CgPanD | 214 ± 32 | 826 ± 33 |

TABLE 8

Yeast strains with chromosomally integrated genes for 3HP biosynthesis

| Final strain | Parent strain | Plasmid with URA3 marker | Plasmid with HIS3 marker | Plasmid with LEU2 marker |
|---|---|---|---|---|
| SCE-R2-180 | CEN.PK102-5B (ura-his-leu-) | pX-2-LoxP-KlURA3-BcBAPAT<-PTEF1-PPGK1->EcYdfG | pX-4-LoxP-SpHiS5-TcPanD<-PTEF1 | pXII-1-LoxP-KlLEU2-AAT2<-PTEF1 |
| SCE-R2-182 | CEN.PK102-5B (ura-his-leu-) | pTY-BcBAPATC-PTEF1-PPGK1->EcYdfG | pX-4-LoxP-SpHiS5-TcPanD<-PTEF1 | pXII-1-LoxP-KlLEU2-AAT2<-PTEF1 |
| SCE-R2-184 | CEN.PK102-5B (ura-his-leu-) | pTY-TcPanD<-PTEF1 | pX-4-LoxP-SpHiS5-BcBAPAT<-PTEF1-PPGK1->EcYdfG | pXII-1-LoxP-KlLEU2-AAT2<-PTEF1 |
| SCE-R2-188 | CEN.PK113-11C (ura-his-) | pX-2-LoxP-KlURA3-BcBAPATC-PTEF1-PPGK1->EcYdfG | pX-4-LoxP-SpHiS5-TcPanD<-PTEF1 | — |
| SCE-R2-190 | CEN.PK113-11C (ura-his-) | pTY-BcBAPATC-PTEF1-PPGK1->EcYdfG | pX-4-LoxP-SpHiS5-TcPanD<-PTEF1 | — |
| SCE-R2-192 | CEN.PK113-11C (ura-his-) | pTY-TcPanD<-PTEF1 | pX-4-LoxP-SpHiS5-BcBAPAT<-PTEF1-PPGK1->EcYdfG | — |
| SCE-R2-196 | ST738 (PYC1^, PYC2^, ura-his-leu-) | pX-2-LoxP-KlURA3-BcBAPAT<-PTEF1-PPGK1->EcYdfG | pX-4-LoxP-SpHiS5-TcPanD<-PTEF1 | pXII-1-LoxP-KlLEU2-AAT2<-PTEF1 |
| SCE-R2-198 | ST738 (PYC1^, PYC2^, ura-his-leu-) | pTY-BcBAPATC-PTEF1-PPGK1->EcYdfG | pX-4-LoxP-SpHiS5-TcPanD<-PTEF1 | pXII-1-LoxP-KlLEU2-AAT2<-PTEF1 |
| SCE-R2-200 | ST738 (PYC1^, PYC2^, ura-his-leu-) | pTY-TcPanD<-PTEF1 | pX-4-LoxP-SpHiS5-BcBAPAT<-PTEF1-PPGK1->EcYdfG | pXII-1-LoxP-KlLEU2-AAT2<-PTEF1 |
| SCE-R2-204 | ST724 (PYC1^, PYC2^, ura-his-) | pX-2-LoxP-KlURA3-BcBAPAT<-PTEF1-PPGK1->EcYdfG | pX-4-LoxP-SpHiS5-TcPanD<-PTEF1 | — |
| SCE-R2-206 | ST724 (PYC1^, PYC2^, ura-his-) | pTY-BcBAPATC-PTEF1-PPGK1->EcYdfG | pX-4-LoxP-SpHiS5-TcPanD<-PTEF1 | — |

TABLE 8-continued

Yeast strains with chromosomally integrated genes for 3HP biosynthesis

| Final strain | Parent strain | Plasmid with URA3 marker | Plasmid with HIS3 marker | Plasmid with LEU2 marker |
|---|---|---|---|---|
| SCE-R2-208 | ST724 (PYC1^, PYC2^, ura-his-) | pTY-TcPanD<-PTEF1 | pX-4-LoxP-SpHiS5-BcBAPAT<-PTEF1-PPGK1->EcYdfG | — |

Results obtained in the following Examples are in part given in the accompanying drawings, in which:

FIG. 3 shows the influence of integrating multiple copies of genes and of overexpression of precursor supply genes on 3HP titer. The concentration of 3HP in the culture broth was determined by HPLC method and is given in g L$^{-1}$. ↑-single copy of gene is integrated into the genome, ↑↑-multiple copies of gene are integrated into the genome (Example 6).

FIG. 4 shows growth and metabolite concentrations in glucose-limited fed-batch cultivation of SCE-R2-200 at pH5. Representative graph of one cultivation out of three (Example 7).

Figure 1:
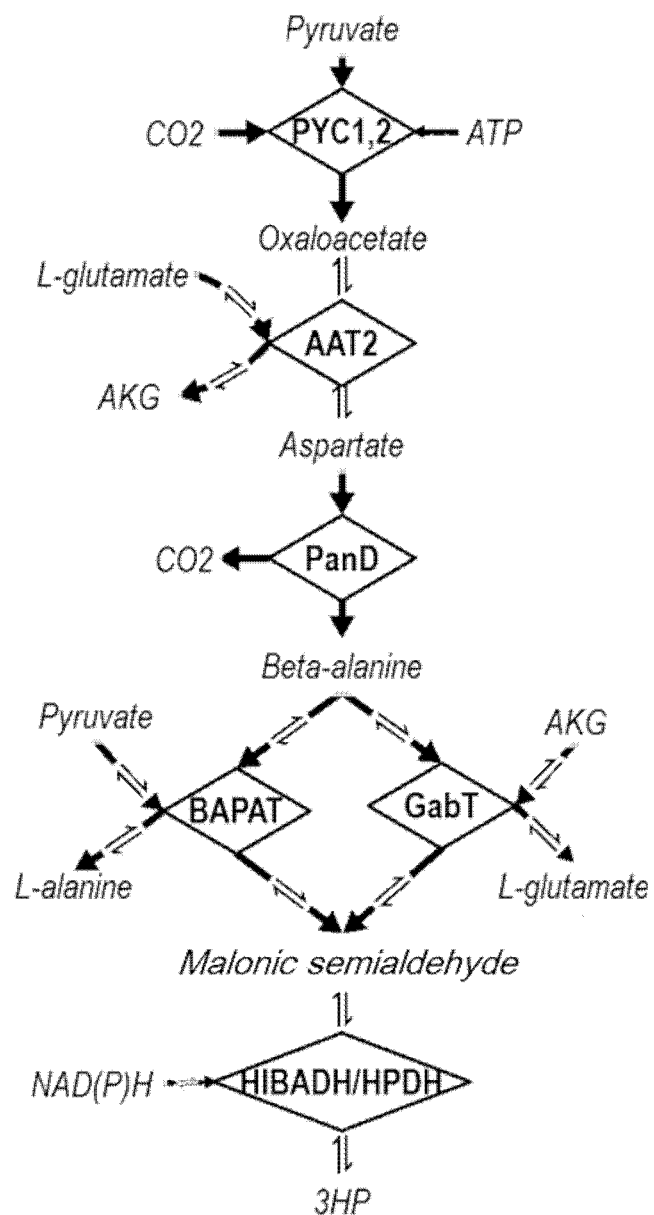
FIG. 1 shows a metabolic pathway leading from pyruvate to 3-HP via aspartate and beta-alanine and malonic semialdehyde.

As illustrated in FIG. 1, apartate can be converted to beta-alanine by the enzyme PanD, aspartate 1-decarboxylase. β-alanine is convertible to malonic semialdehyde by either BAPAT or GabT, and malonic semialdehyde is convertible to 3-HP by HIBADH/HPDH. The present invention uses the route via BAPAT.

EXAMPLE 1. CLONING OF HETEROLOGOUS BETA-ALANINE-PYRUVATE AMINOTRANSFERASE, 3-HYDROXYISOBUTYRATE DEHYDROGENASE, AND 3-HYDROXYPROPANOATE DEHYDROGENASE AND OVEREXPRESSION OF HETEROLOGOUS AND NATIVE GAMMA-AMINOBUTYRATE TRANSAMINASE IN S. CEREVISIAE

Genes encoding a putative *B. cereus* aminotransferase yhxA (SEQ ID NO1), *Pseudomonas putida* beta-alanine-pyruvate aminotransferase (SEQ ID NO3), *P. aeruginosa* 3-hydroxybutyrate dehydrogenase (SEQ ID NO5), *Candida albicans* 3-hydroxybutyrate dehydrogenase (SEQ ID NO7), *P. putida* 3-hydroxybutyrate dehydrogenase (SEQ ID NO9), *Bacillus cereus* 3-hydroxybutyrate dehydrogenase (SEQ ID NO11), *Metallosphaera sedula* 3-hydroxypropanoate dehydrogenase (SEQ ID NO13), *Sulfolobus tokadaii* 3-hydroxypropanoate dehydrogenase (SEQ ID NO15), and *Clostridium acetobutylicum* gamma-aminobutyrate transaminase (SEQ ID NO17) were synthesized by GeneArt (Life Technologies) in versions codon-optimized for yeast *S. cerevisiae* (corresponding SEQ ID NO2, SEQ ID NO4, SEQ ID NO6, SEQ ID NO8, SEQ ID NO10, SEQ ID NO12, SEQ ID NO14, SEQ ID NO16, SEQ ID NO18).

The ordered gene constructs had a general structure: GGTACCAAAACAATGNN . . . NNTGA GTCGAC(SEQIDNO67), where GGTACC is a KpnI restriction site, AAAACA is the Kozak sequence, ATG is the start codon, NN . . . NN represents the protein coding sequence without start and stop codons, TGA is the stop codon, GTCGAC is a SalI restriction site.

The synthetic genes were excised from the plasmids using KpnI and SalI, gel-purified and ligated into plasmid pE1 (SEQ ID 81) or pE2 (SEQ ID82), which were digested with the same enzyme pair. The resulting ligation mix was transformed into chemically competent *E. coli* DH5alpha using heat shock and the cells were selected on Luria-Bertani (LB) agar medium with 100 µg/ml amplicillin.

The clones with correct inserts were identified by colony PCR, inoculated in liquid LB medium with 100 µg/ml ampicillin and the plasmids were isolated (Table 2). The resulting plasmids were confirmed by sequencing.

The gene fragments carrying the genes and correct overhangs for USER-cloning were generated by PCR amplification using primers and templates as indicated in Table 3. The PCR mix contained: 28 µl water, 10 µl high fidelity Phusion® polymerase buffer (5×), 5 µl 2 mM dNTP, 1 µl Phusion® polymerase, 2.5 µl forward primer at 10 µM concentration, 2.5 µl reverse primer at 10 µM concentration, and 1 µl DNA template. The cycling program was: 95° C. for 2 min, 30 cycles of [95° C. for 10 sec, 50° C. for 20 sec, 68° C. for 2 min], 68° C. for 5 min, pause at 10° C. The gene fragments were resolved on 1% agarose gel containing SYBR®-SAFE (Invitrogen) and purified using Nucleo-Spin® Gel and PCR Clean-up kit (Macherey-Nagel). The promoter fragments were also generated by PCR followed by gene purification (Table 3). The terminators were already present on the expression plasmids.

The parent plasmids pESC-Ura-USER (SEQ ID NO 85), pESC-His-USER (SEQ ID NO 83) and pESC-Leu-USER (SEQ ID NO 84) were linearized with FastDigest® AsiSI (Fermentas) for 1 hour at 37° C. and nicked with Nb.BsmI for 1 hour at 37° C. The resulting linearized nicked DNA was purified from the solution and eluted in 5 mM Tris buffer, pH 8.0.

The expression plasmids were created by USER-cloning using the following protocol. 1 µl of linearized and nicked parent plasmid was mixed with 1 µl of promoter fragment, 2 µl of gene fragment, 0.5 µl Taq polymerase buffer, 0.5 µl USER enzyme (NEB). The mix was incubated at 37° C. for 25 min, at 25° C. for 25 min and transformed into chemically competent *E. coli* DH5alpha. The clones with correct inserts were identified by colony PCR and the plasmids were isolated from overnight *E. coli* cultures and confirmed by sequencing. The expression plasmids are listed in Table 4.

The expression plasmids were transformed into *S. cerevisiae* cells using the lithium acetate transformation protocol. The cells were selected on synthetic complete (SC) agar medium without uracil, histidine and leucine. The resulting strains are listed in Table 5.

EXAMPLE 2. PRODUCTION OF 3-HYDROXYPROPIONIC ACID IN *S. CEREVISIAE* CULTIVATED ON β-ALANINE

At least four independent yeast transformants were streak-purified on SC ura-his-leu-agar plates. Four single colonies originating from independent transformants were inoculated in 0.5 ml SC ura-his-leu- in a 96-deep well microtiter plate with air-penetrable lid (EnzyScreen). The plates were incubated at 30° C. with 250 rpm agitation at 5 cm orbit cast overnight. 50 µl of the overnight cultures were used to inoculate 0.5 ml minimal mineral (Delft) medium with 10 g/L β-alanine in a 96-deep well plate.

The composition of the of Delft medium was as following: 7.5 g $(NH_4)_2SO_4$, 14.4 g $KH_2PO_4$, 0.5 g $MgSO_4.7H_2O$, 22 g dextrose, 2 mL trace metals solution, and 1 mL vitamins. pH of the medium was adjusted to 6. The trace metals solution contained per liter: 4.5 g $CaCl_2.2H_2O$, 4.5 g $ZnSO_4.7H_2O$, 3 g $FeSO_4.7H_2O$, 1 g $H_3BO_3$, 1 g $MnCl_2.4H_2O$, 0.4 g $Na_2MoO_4.2H_2O$, 0.3 g $CoCl_2.6H_2O$, 0.1 g $CuSO_4.5H_2O$, 0.1 g KI, 15 g EDTA. The trace metals solution was prepared by dissolving all the components except EDTA in 900 mL ultra-pure water at pH 6 followed by gentle heating and addition of EDTA. Finally the trace metal solution pH was adjusted to 4, and the solution volume was adjusted to 1 L and autoclaved (121° C. in 20 min). Trace metals solution was stored at +4° C. The vitamins solution contained per liter: 50 mg biotin, 200 mg p-aminobenzoic acid, 1 g nicotinic acid, 1 g Ca-pantotenate, 1 g pyridoxine-HCl, 1 g thiamine-HCl, 25 g myo-inositol. Biotin was dissolved in 20 mL 0.1 M NaOH and 900 mL water is added. pH was adjusted to 6.5 with HCl and the rest of the vitamins was added. pH was re-adjusted to 6.5 just before and after adding m-inositol. The final volume of the vitamin solution was adjusted to 1 l and sterile-filtered before storage at +4° C.

Fermentation was carried out for 72 hours at the same conditions as above.

At the end of the cultivation the $OD_{600}$ was measured. 10 µl of the sample was mixed with 190 µl water and absorbance was measured at 600 nm wave length in spectrophotometer (BioTek).

The culture broth was spun down and the supernatant analyzed for 3-hydroxypropionic acid concentration using enzymatic assay (Table 5). No 3HP production was obtained when *P. putida* beta-alanine-pyruvate aminotransferase or *C. acetobutylicum* gamma-aminobutyrate transaminase were used in combination with 3-hydroxybutyrate dehydrogenase or 3-hydroxypropanoate dehydrogenase. However 3HP production from beta-alanine was observed when putative *B. cereus* aminotransferase YhxA or *S. cerevisiae* gamma-aminobutyrate transaminase were combined with 3-hydroxybutyrate dehydrogenase or 3-hydroxypropanoate dehydrogenase (Table 5: strains 133-147). The best enzyme combination under the conditions tested was strain 147 expressing *B. cereus* aminotransferase YhxA and *E. coli* 3-hydroxypropanoate dehydrogenase YdfG, where 2,145±89 mg/L 3HP was obtained.

Enzymatic assay was carried out as follows. 20 µl of standards (3HP at concentrations from 0.03 to 1 g/L in Delft medium) and samples were added to a 96-well flat bottom transparent plate (Greiner). 180 µl of mix (14.8 ml water, 2 ml buffer (1 mM Tris, 25 mM $MgCl_2$, pH 8.8), 1 ml NADP+ solution (50 mg/ml), and 0.2 ml purified YdfG enzyme in PBS buffer (1500 µg/ml)) was added per well using multi-channel pipet. The start absorbance at 340 nm was measured, the plate was sealed and incubated at 30° C. for 1.5 hours. After that the end absorbance at 340 nm was measured again. The difference between the end and the start values corrected for the background were in linear correlation with 3HP concentrations. The concentration of 3HP in the samples was calculated from the standard curve.

Figure 2:
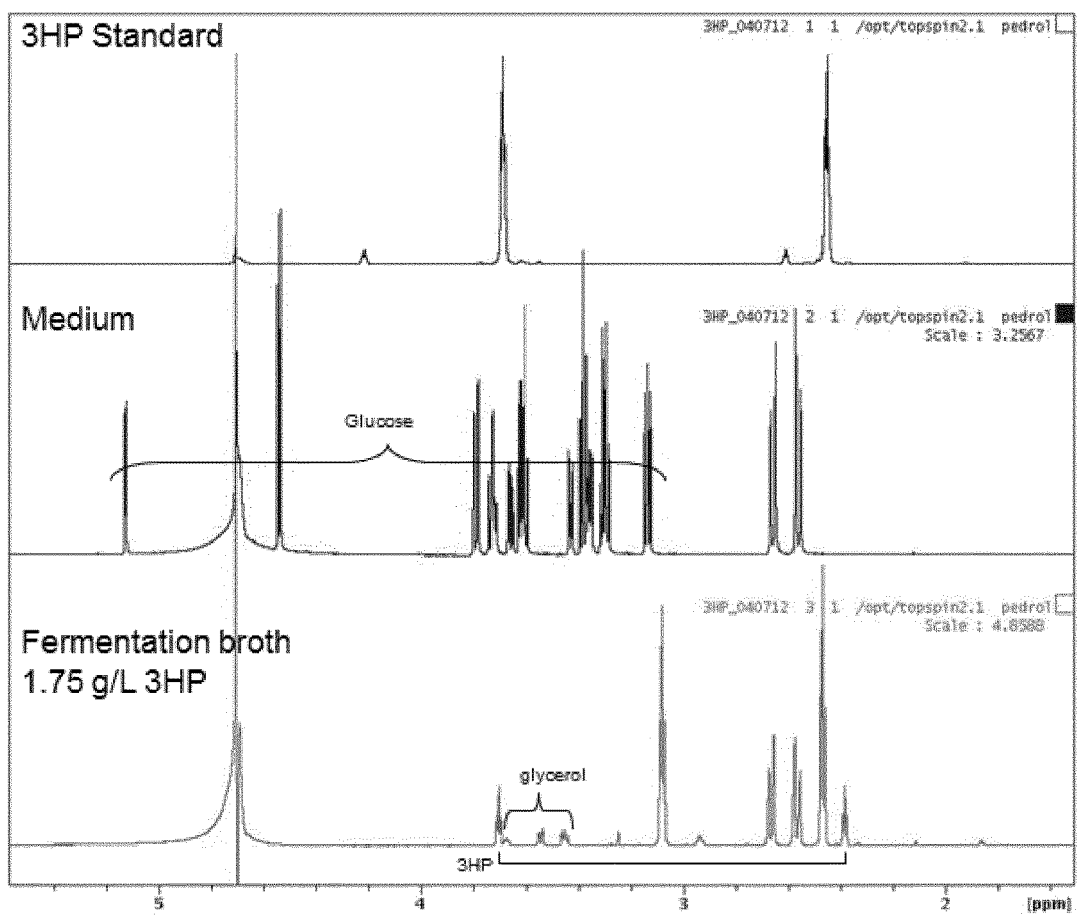
FIG. 2 shows NMR results obtained in Example 2.

The identity of 3-hydroxypropionic acid in the best sample was confirmed by NMR analysis (FIG. 2). The concentration measured by NMR correlated well with the value found by enzymatic assay.

EXAMPLE 3. CLONING OF ASPARTATE-1-DECARBOXYLASE OR GLUTAMATE DECARBOXYLASE IN *S. CEREVISIAE*

Genes encoding *E. coli* aspartate 1-decarboxylase (SEQ ID NO50) and *C. glutamicum* aspartate 1-decarboxylase (SEQ ID NO52) were synthesized as gBLOCKs by Integrated DNA Technologies (in versions codon-optimized for yeast *S. cerevisiae* corresponding SEQ ID NO51 and SEQ ID NO53).

Gene encoding glutamate decarboxylase from *Rattus norvegicus* (SEQ ID NO58) was synthesized by GeneArt (Life Technologies) in version codon-optimized for yeast *S. cerevisiae* (SEQ ID NO59).

The ordered gene constructs had a general structure: GGTACCAAAACAATGNN . . . NNTGA GTCGAC(SEQIDNO67), where GGTACC is a KpnI restriction site, AAAACA is the Kozak sequence, ATG is the start codon, NN . . . NN represents the protein coding sequence without start and stop codons, TGA is the stop codon, GTCGAC is a SalI restriction site.

The gene fragments carrying the genes and correct overhangs for USER-cloning were generated by PCR amplification using primers and templates as indicated in Table 3. The PCR mix contained: 28 µl water, 10 µl high fidelity Phusion® polymerase buffer (5×), 5 µl 2 mM dNTP, 1 µl Phusion® polymerase, 2.5 µl forward primer at 10 µM concentration, 2.5 µl reverse primer at 10 µM concentration, and 1 µl DNA template. The cycling program was: 95° C. for 2 min, 30 cycles of [95° C. for 10 sec, 50° C. for 20 sec, 68° C. for 2 min], 68° C. for 5 min, pause at 10° C. The gene fragments were resolved on 1% agarose gel containing SYBR®-SAFE (Invitrogen) and purified using Nucleo-Spin® Gel and PCR Clean-up kit (Macherey-Nagel). The promoter fragments were also generated by PCR followed by gene purification (Table 3). The terminators were already present on the expression plasmids.

The parent plasmids pESC-Ura-USER, pESC-His-USER and pESC-Leu-USER were linearized with FastDigest® AsiSI (Fermentas) for 1 hour at 37° C. and nicked with Nb.BsmI for 1 hour at 37° C. The resulting linearized nicked DNA was purified from the solution and eluted in 5 mM Tris buffer, pH 8.0.

The expression plasmids were created by USER-cloning using the following protocol. 1 µl of linearized and nicked parent plasmid was mixed with 1 µl of promoter fragment, 2 µl of gene fragment, 0.5 µl Taq polymerase buffer, 0.5 µl USER enzyme (NEB). The mix was incubated at 37° C. for 25 min, at 25° C. for 25 min and transformed into chemically competent *E. coli* DH5alpha. The clones with correct inserts were identified by colony PCR and the plasmids were isolated from overnight *E. coli* cultures and confirmed by sequencing. The expression plasmids are listed in Table 4.

The expression plasmids were transformed into *S. cerevisiae* cells using the lithium acetate transformation protocol.

The cells were selected on synthetic complete (SC) agar medium without uracil, histidine and leucine. The resulting strains are listed in Table 6.

EXAMPLE 4. PRODUCTION OF 3-HYDROXYPROPIONATE IN S. CEREVISIAE CULTIVATED ON L-ASPARTATE

At least four independent yeast transformants were streak-purified on SC ura-his-leu-agar plates. Four single colonies originating from independent transformants were inoculated in 0.5 ml SC ura-his-leu- in a 96-deep well microtiter plate with air-penetrable lid (EnzyScreen). The plates were incubated at 30° C. with 250 rpm agitation at 5 cm orbit cast overnight. 50 µl of the overnight cultures were used to inoculate 0.5 ml Delft medium with 10 g/L L-aspartate in a 96-deep well plate. Fermentation was carried out for 72 hours at the same conditions as above.

The culture broth was spun down and the supernatant analyzed for 3-hydroxypropionic acid concentration using enzymatic assay as described in Example 2 (Table 6).

3HP production from L-aspartate was observed only when aspartate 1-decarboxylase from *C. glutamicum* was expressed in combination with enzymes converting beta-alanine into 3HP (putative *B. cereus* aminoransferase YhxA and *E. coli* 3-hydroxypropanoate dehydrogenase YdfG or *Metallosphaera sedula* 3-hydroxypropanoate dehydrogenase). The best combination was aspartate 1-decarboxylase from *C. glutamicum*, putative *B. cereus* aminoransferase YhxA and *E. coli* 3-hydroxypropanoate dehydrogenase YdfG, which resulted in 269±53 mg/L 3HP.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

EXAMPLE 5. EXPRESSION OF ASPARTATE-1-DECARBOXYLASE FROM RED FLOUR BEETLE IN S. CEREVISIAE AND PRODUCTION OF 3HP FROM GLUCOSE

The gene encoding *Tribolium castaneum* aspartate 1-decarboxylase TcPanD (SEQ ID 68) was synthesized in version codon-optimized for *S. cerevisiae* (SEQ ID 69) by GeneArt (LifeTech Sciences).

The TcPanD gene was amplified using PCR in order to generate USER-cloning compatible overhangs as described in Example 1 using primers TcPanD_U1_fw and Tc_PanD_rv (Table 3). The resulting DNA fragment TcPanD← was cloned into expression plasmid pESC-HIS-USER along with TEF1 promoter to result in plasmid pESC-HIS-TcPanD (Table 4). Correct insertion of TcPanD gene and the promoter was confirmed by sequencing.

The plasmids were transformed into *S. cerevisiae* strain using the lithium acetate transformation protocol; the resulting strains are shown in Table 7.

At least three independent yeast transformants were inoculated in 0.5 ml SC ura-his-leu- in a 96-deep well microtiter plate with air-penetrable lid (EnzyScreen). The plates were incubated at 30° C. with 250 rpm agitation at 5 cm orbit cast overnight. 50 µl of the overnight cultures were used to inoculate 0.5 ml minimal mineral (Delft) medium or 0.5 ml Feed-in-time medium (FIT) for *S. cerevisiae* (M2P Labs, Germany) in 96-deep well plates.

Fermentation was carried out for 72 hours at the same conditions as inoculum preparation. The culture broth was spun down and the supernatant was analyzed for 3-hydroxypropionic acid concentration using HPLC (Table 7).

HPLC analysis was performed on Dionex UltiMate 3000 system (Thermo Fisher Scientific) with Aminex HPX-87H column (Bio-Rad Laboratories, Hercules, Calif.) operating at 60° C. The injection volume was 20 µl. The mobile phase was 1 mM $H_2SO_4$ at a flow rate of 0.6 ml/min. 3HP was detected on DAD-3000 Diode Array Detector (Dionex) using the read at 210 nm. The calibration curve was made using 3-hydroxypropionic acid purchased from TCI. The identity of the 3-hydroxypropionic acid was additionally verified by comparison of the spectrum with the standard.

Aspartate 1-decarboxylase from *T. castaneum* resulted in almost 3-fold higher 3HP titer on Delft and 2-fold higher 3HP titer on FIT medium than aspartate 1-decarboxylase from *C. glutamicum*. Thus we have confirmed that if the strain capable of producing 3HP from β-alanine is supplemented with aspartate 1-decarboxylase enzyme from *C. glutamicum* or better from *T. castaneum* then it can produce 3HP directly from glucose.

EXAMPLE 6. IMPROVEMENT OF 3HP PRODUCTION BY OVEREXPRESSION OF PRECURSOR

Once the biosynthesis of 3HP from glucose via beta-alanine has been established in yeast, the next goal was to improve the expression of the biosynthetic genes and to increase the flux towards L-aspartate. As this would require stable simultaneous overexpression of several genes, we used EasyClone integrative vectors for yeast. We tested the effect of overexpressing native cytoplasmic aspartate aminotransferase Aat2p, pyruvate carboxylases Pyc1p and Pyc2p and of the combination thereof. We also investigated the effect of multiple chromosomal integration of the key biosynthetic genes leading from aspartate to 3HP.

The genes encoding aspartate aminotransferase AAT2 and pyruvate carboxylases PYC1 and PYC2 were amplified from gDNA of *S. cerevisiae* CEN.PK113-7D using primers as in Table 3 and PCR conditions as in Example 1. The resulting DNA fragments were purified and cloned into EasyClone expression vectors as described in Example 1 (see Table 4).

Strain ST724 (PYC1^, PYC2^, ura-his-) was created by transforming *S. cerevisiae* CEN.PK102-5B (ura-his-leu-) with plasmid pXI-1-LoxP-KlLEU2-PYC1←PTEF1-PPGK1→PYC2, selecting the transformants on SC drop-out medium without leucine and confirming the correct integration of the plasmid by PCR on genomic DNA of the transformant. Strain ST724 was used to create strain ST738 (PYC1^, PYC2^, ura-his-leu-) by looping out the KlLEU2 selection marker using LoxP-Cre-mediated recombination.

The yeast strains were transformed with expression plasmids according to Table 8 and transformants were selected on SC drop-out medium without uracil, histidine and leucine. The strains were cultivated and 3HP concentrations were analyzed as described in Example 5. The results are shown in FIG. 3.

Increasing copy number of BcBAPAT/EcYdfG or of TcPanD lead to improvement of 3HP titer for all the four background strains tested (reference, overexpressing AAT2, overexpressing PYC1&PYC2 and overexpressing AAT2&PYC1&PYC2). The effect of multiple integrations of TcPanD was larger than that of multiple copies of BcBAPAT/EcYdfG.

The increased precursor supply (via overexpression of PYC1/PYC2 and/or AAT2) had a positive effect on 3HP production in strains with multiple copies of TcPanD or BcBAPAT/EcYdfG genes, but not in the strains that had only single copies of the latter genes. The positive effect of overexpressing pyruvate carboxylase genes was only observed on feed-in-time medium, which simulates fed-batch conditions. The highest titers were obtained for the strain SCE-R2-200 (AAT2↑PYC1↑PYC2↑BcBAPAT↑EcYdfG↑TcPanD↑↑): 1.27±0.28 g/L and 8.51±1.05 g/L on mineral and feed-in-time media correspondingly.

EXAMPLE 7. PRODUCTION OF 3HP BY YEAST IN FED-BATCH CULTIVATION AT PH5

The best isolate of strain SCE-R2-200 described above was cultivated in aerobic fed-batch cultivation with glucose-limited feed at pH5 in triplicates.
SCE-R2-200 glycerol stock (0.3 ml) was inoculated in 150 ml Delft medium in 500-ml baffled shake flask and propagated at 30° C. with 250 rpm agitation for about 24 hours. The culture was concentrated down to 50 ml by centrifugation at 4,000×g for 2 min and used to inoculate 0.5 L medium in 1L-Sartorius reactor. The final medium in the reactors contained per liter: 15 g $(NH_4)_2SO_4$, 6 g $KH_2PO_4$, 1 g $MgSO_4.7H_2O$, 4 ml trace metals solution, 2 ml vitamins solution, 0.4 ml antifoam A (Sigma-Aldrich), and 44 g dextrose. Dextrose was autoclaved separately, vitamins solution was sterile filtered and added to the medium after autoclavation. The trace metal and vitamins solutions are the same as described in Example 2. The agitation rate was 800 rpm, the temperature was 30° C., aeration was 1 L $min^{-1}$ air and pH was maintained at 5.0 by automatic addition of 2N NaOH. Carbon dioxide concentration in the off-gas was monitored by acoustic gas analyzer (model number 1311, Bruël & Kjær). Once the glucose was exhausted, which was observed from decline in $CO_2$ production and was also confirmed by residual glucose detection using glucose strips Glucose MQuant™ (Merck Millipore), the feed was started at 5 g $h^{-1}$. The feed contained per liter: 45 g $(NH_4)_2SO_4$, 18 g $KH_2PO_4$, 3 g $MgSO_4.7H_2O$, 12 ml trace metals solution, 6 ml vitamins solution, 0.6 ml antifoam A, and 176 g dextrose. Dextrose was autoclaved separately, vitamins solution was sterile filtered and added to the feed after autoclavation.

24 hours after the feed start the feed rate was ramped up to 10 g $h^{-1}$ and 48 hours after the feed start it was further increased to 15 g $h^{-1}$. The reactors were sampled twice a day to measure biomass dry weight and metabolites. For metabolites analysis the sample was immediately centrifuged and the supernatant was stored at −20° C. until HPLC analysis. HPLC analysis of glucose, succinate, acetate, 3HP, glycerol, ethanol, and pyruvate was carried out at described in Example 5. Glucose, glycerol and ethanol were detected using RI-101 Refractive Index Detector (Dionex). 3HP, pyruvate, succinate and acetate were detected with DAD-3000 Diode Array Detector at 210 nm (Dionex).

The strain produced 3-hydroxypropionic acid at 13.7±0.3 g·L-1 titer, 14±0% C-mol·C-mol-1 glucose yield and 0.24±0.0 g·L-1·h-1 productivity. No significant amounts of by-products as acetate, ethanol or glycerol were detected at the end of the fermentation. Results are shown in FIG. 4.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof. The content of the sequence listing filed herewith forms part of the description of the invention.

The invention claimed is:

1. A genetically modified yeast cell comprising an enhanced-fermentation pathway for producing 3-hydroxypropionic acid (3HP), wherein the fermentation pathway includes an enzyme having at least 85% identity with SEQ ID NO: 1, and catalysing a transamination reaction between beta-alanine and pyruvate to produce malonate semialdehyde, and wherein said enzyme is the expression product of an exogenous gene that is expressed by the genetically modified yeast cell.

2. A genetically modified yeast cell as claimed in claim 1, wherein said enzyme is the aminotransferase YhxA from *Bacillus cereus* AH1272.

3. A genetically modified yeast cell as claimed in claim 1, expressing a 3-hydroxyisobutyrate dehydrogenase (HIBADH).

4. A genetically modified yeast cell as claimed in claim 3, wherein said HIBADH is from *Pseudomonas aeruginosa, P. putida, Bacillus cereus*, or *Candida albicans*.

5. A genetically modified yeast cell as claimed in claim 1, wherein the yeast is *S. cerevisiae*.

6. A method for the production of 3HP comprising culturing the modified yeast cell according to claim 1 and recovering 3HP from the culture.

7. A method as claimed in claim 6, comprising supplying said culture with beta-alanine and/or L-aspartate.

8. A method as claimed in claim 6, wherein at least 100 mg of 3HP per liter of culture medium is produced or is recovered from said culture medium.

* * * * *